United States Patent [19]

Gutnick et al.

[11] 4,395,354

[45] Jul. 26, 1983

[54] EMULSANS

[75] Inventors: David L. Gutnick, Ramat Aviv; Eugene Rosenberg, Raanana; Igal Belsky, Ramat Aviv; Zinaida Zosim, Kefar Sava, all of Israel

[73] Assignee: Petroleum Fermentations N.V., Netherlands Antilles

[21] Appl. No.: 166,981

[22] Filed: Jul. 17, 1980

Related U.S. Application Data

[63] Continuation of Ser. No. 12,971, Feb. 22, 1979, abandoned.

[51] Int. Cl.³ .................. B01F 17/30; B01F 17/34; B01F 17/52
[52] U.S. Cl. .................. 252/356; 210/925; 252/8.55 D; 252/312; 252/352; 252/DIG. 6; 435/101
[58] Field of Search .............. 252/352, 356; 435/101; 210/925

[56] References Cited

U.S. PATENT DOCUMENTS 3,941,692  3/1976  Gutnick et al. ............... 210/611
3,997,398  12/1976  Zajic et al. .................. 435/101

OTHER PUBLICATIONS

Towner et al., "RP4 Fertility Variants in Acinetobacter Calcoaceticus", Genet. Res. 28: 301-306, (1976).
Horowitz et al.: Applied Microbiology, 30, 10 (1975).
Gutnick et al.: Annual Reviews of Microbiology, 31, 379 (1977).
Reisfeld et al.: Applied Microbiology, 24, 363 (1972).
Rosenberg et al.: EPA Report 660-3-75-001, pp. 157-68, Dec. 1974.
Englander et al.: Int. Assoc. Microbiol. Soc. Abstracts, vol. II, p. 201.
Zajic et al.: Dev. Ind. Microbiol., 12, 87 (1971).
Zajic et al.: Biotechnol. Bioeng., 14, 331 (1972).
Zajic et al.: Chemosphere, 1, 51 (1972).
Zajic et al.: Critical Rev. Microbiol., 5, 39 (1976).

*Primary Examiner*—Richard D. Lovering
*Attorney, Agent, or Firm*—Pennie & Edmonds

[57] ABSTRACT

Growth of Acinetobacter Sp. ATCC 31012 on various substrates and under varying conditions has been used to produce two classes of extracellular microbiol protein-associated lipopolysaccharides (the "emulsans") which, on a weight-for-weight basis, are probably the most efficient emulsifiers discovered and which possess certain characteristics that permit these unique extracellular microbial lipopolysaccharides to be widely used in cleaning oil-contaminated vessels, oil spill management, and enhanced oil recovery by chemical flooding. These classes have been named α-emulsans and β-emulsans, both of which have substantially the same polymer backbone but differ from each other in certain important structural aspects. Emulsans and apoemulsans, both of which biopolymers are strongly anionic, exhibit a high degree of specificity in the emulsification of hydrocarbon substrates which contain both aliphatic and cyclic components. In addition, these extracellular microbial polysaccharides as well as their O-deacylated and N-deacylated derivatives are adsorbed on and capable of flocculating aluminosilicate ion-exchangers, such as kaolin and bentonite.

28 Claims, 18 Drawing Figures

EMULSANS

This is a continuation of application Ser. No. 012,971, filed Feb. 22, 1979, now abandoned.

TABLE OF CONTENTS

1. Introduction
2. Background of the Invention
3. Summary of the Invention
4. Nomenclature
5. Brief Description of the Drawings 6. Production of Emulsans and Apoemulsans
    6.1 Acinetobacter Sp. ATCC 31012
    6.2 Fermentation Media
        6.2.1. Utilizable Carbon Sources
        6.2.2. Additional Nutrients
        6.2.3. Divalent Cations
    6.3. Fermentation Process Conditions
        6.3.1. Aeration
        6.3.2. Agitation
        6.3.3. Temperature and pH
        6.3.4. Defoaming
    6.4 Extracellular Production of Emulsans
        6.4.1. Standard Assay for Emulsifying Activity
        6.4.2. Extracellular Production of α-Emulsans
        6.4.3. Extracellular Production of β-Emulsans
        6.4.4. Distribution of Emulsifying Activity in Fractions of Growth Culture
    6.5. Deproteinization
    6.6. Isolation and Purification
        6.6.1. Heptane Partitioning
        6.2.2. Ammonium Sulfate Precipitation
        6.6.3. Quaternary Ammonium Salt Precipitation
7. Chemical and Physical Properties of Emulsans and Apoemulsans
    7.1. Preparation of Samples for Analytical Characterization
        7.1.1. Preparation of Emulsan
        7.1.2. Preparation of Apoemulsan Samples
        7.1.3. Ammonium Sulfate Fractionation of Apo-α-Emulsan
        7.1.4. Quaternary Ammonium Salt Precipitation of Apo-α-Emulsan
    7.2. Chemical Characterization
        7.2.1. Chemical Composition of Emulsans and Apoemulsans
        7.2.2. Alkaline Hydrolysis of Emulsans and Apoemulsans
        7.2.3. Acid Hydrolysis of Apoemulsans and of Proemulsan
        7.2.4. Identification of Sugar Components
        7.2.5. Identification of Fatty Acids
    7.3. Physical Characterization
        7.3.1. Intrinsic and Reduced Viscosity
        7.3.2. Sedimentation Velocity Analysis
        7.3.3. Estimation of Molecular Weight
        7.3.4. Spectral Properties
    7.4. Conclusions on Structure
    7.5. Variations in Structure
    7.6 Immunological Characterization
8. Emulsifying Properties
    8.1. Kinetics of Emulsan-Induced Emulsion Formation
    8.2. Effect of pH and Salt Concentration on Emulsion Formation
    8.3. Stability of Emulsan-Induced Emulsions
    8.4. Lowering of Oil/Sea Water Interfacial Tensions
9. Specificity of the Hydrocarbon Substrate
    9.1. Emulsification of Petroleum Fractions
    9.2. Emulsification of Pure Hydrocarbons
    9.3. Emulsification of Mixtures of Pure Hydrocarbons
    9.4. Effect of Addition of Aliphatic and Aromatic Compounds on Emulsification of Petroleum Fractions
10. Summary of Differences Between α-Emulsans and β-Emulsans
    10.1. Differences in Yield
    10.2. Differences in Structure
    10.3. Differences in Emulsifying Activity
11. Sorptive Properties of Emulsans and Their Derivatives on Solid Substrates
    11.1. Non-Adsorption on Sand and Limestone
    11.2. Adsorption on Aluminosilicate Clays
    11.3. Flocculation of Clays
    11.4. Relationship of Flocculation to Breaking Oil/Water Emulsions
12. Environmental and Energy-Related Uses
13. Examples
    13.1. Preparation of α-Emulsan from Ethanol in Fresh Water Media
    13.2. Preparation of α-Emulsan from Ethanol in Sea Water Media
    13.3. Preparation of α-Emulsan from Sodium Palmitate
    13.4. Preparation of α-Emulsan from Dodecane
    13.5. Preparation of β-Emulsan from Hexadecane
    13.6. Preparation of Apo-α-Emulsan
    13.7. Preparation of Apo-β-Emulsan
    13.8. Preparation of ψ-Emulsan
    13.9. Preparation of Proemulsan
    13.10. Purification of α-Emulsan by Precipation with Ammonium Sulfate
    13.11. Purification of α-Emulsan by Precipation with Quaternary Ammonium Salts
    13.12. Purification of β-Emulsan by Heptane Partitioning
    13.13. Ammonium Sulfate Fractionation of Apo-α-Emulsan
    13.14. Emulsification of Petroleum Fractions by α-Emulsans and β-Emulsans
    13.15. Emulsification of Mixtures of Petroleum Fractions and Pure Hydrocarbons by Emulsan
    13.16. Cleaning Oil-Contaminated Vessels
    13.17. Effect of Mobility Control Polysaccharides on Emulsion Formation with Emulsan
    13.18. Adsorption of Emulsans on Clays
    13.19. Flocculation of Clays by Emulsans
    13.20. Flocculation of Clays by Proemulsans
    13.21. Breaking Emulsan-Induced Emulsions
    13.22. Removal of Oil from Sand by Emulsan
    13.23. Removal of Oil from Limestone by Emulsan

INTRODUCTION

This invention relates to extracellular microbial polysaccharides (herein generically called "emulsans") produced by Acinetobacter Sp. ATCC 31012 and, more particularly, to a new class of extracellular microbial protein-associated lipopolysaccharides (herein collectively called "α-emulsans") produced by this organism and its mutants or recombinants. The invention further relates to the deproteinized lipopolysaccharides (herein collectively called "apoemulsans") obtained from such emulsans, as well as to the divalent metal, ammonium and quaternary ammonium salts of such emulsans and apoemulsans. These extracellular microbial polysaccharides, which include both the emulsans and apoemulsans and their respective salts, are among the most efficient oil-in-water emulsifiers ever discovered and possess a high degree of specificity in both fresh water and sea water for emulsifying those hydrocarbon substrates which contain both aliphatic and aromatic or cyclic components, properties which make these unique bioemulsifiers ideal for use in cleaning oil-contaminated vessels, oil spill management, and enhanced oil recovery by chemical flooding.

BACKGROUND OF THE INVENTION

A wide variety of petroleum-degrading microorganisms has been found to bring about the formation of oil-in-water emulsions while growing on hydrocarbons. These emulsions are microbiological in origin and appear to be mediated either by the cells themselves or by the production of extracellular emulsifying agents. For example, the growth of Mycobacterium rhodochrous NCIB 9905 on n-decane yields an emulsifying factor which was reported by R. S. Holdom et al. [J. Appl. Bateriol., 32, 448 (1969)] to be a nonionic detergent. J. Iguchi et al. [Agric Biol. Chem., 33, 1657 (1969)] found that *Candida petrophilium* produced an emulsifying agent composed of peptides and fatty acid moieties, while T. Suzuki et al. [Agric. Biol. Chem., 33, 1619 (1969)] found trehalose lipid in the oil phase of culture broths of various strains of Arthrobacter, Brevibacterium, Corynebacterium and Norcardia.

*Torulopsis gropengiesseri* was found to produce a sophorose lipid, while rhamnolipids are reported by K. Hisatsuka et al. [Agric. Biol. Chem., 35, 686 (1971)] to have been produced by *Pseudomonas aeruginosa* strain S7B1 and by S. Itoh et al. [Agric. Biol. Chem., 36, 2233 (1971)] to have been produced by another *P. aeruginosa* strain, KY4025. The growth of *Corynebacterium hydrocarbolastus* on kerosene was reported by J. E. Zajic and his associated [Dev. Ind. Microbiol., 12, 87 (1971); Biotechnol. Bioeng., 14, 331 (1972); Chemosphere, 1, 51 (1972); Crit. Rev. Microbiol., 5, 39 (1976) U.S. Pat. No. 3,997,398] to produce an extracellular heteropolysaccharide which, among other properties, emulsified kerosene, Bunker C fuel oil and other fuel oils.

In U.S. Pat. No. 3,941,692, we described the use of an Arthrobacter species, RAG-1 (which, upon deposit with the American Type Culture Collection, has been designated as Arthrobacter Sp. ATCC 31012 and is now known to have been an Acinetobacter species and has been redesignated as Acinetobacter Sp. ATCC 31012) to clean oil-contaminated tank compartments by allowing the organism to aerobically grow on the oily wastes in such tanks using sea water containing added nutrients. During that microbially-induced cleaning process, the organism appeared to secrete one or more dispersants during the fermentation, since the cell-free fermentation medium was also effective in cleaning waste oil from such tanks.

Further studies on the microbial degradation of crude oil by this organism [Appl Microbiol., 24, 363 (1972); Appl. Microbiol., 30, 10 (1975)], showed that RAG-1 emulsified the oil during exponential growth, probably by producing an extracellular emulsifying agent which acted to break up the oil droplets into smaller units and thereby produce new surface area, necessary for the increasing cell population. At the 1st International Congress for Bacteriology held September 2-7, 1973 [Int. Assoc. Microbiol. Soc. Abstracts, Vol. II, p. 201], we reported that this extracellular emulsifying agent had been partially purified from stationary phase cultures of RAG-1 growing on 0.4% hexadecane, 0.075 M urea and 5.8 mM dibasic potassium phosphate in sea water. The partially purified extracellular emulsifying agent was obtained by extensively dialyzing and then lyophilizing the cell-free fermentation broth, yielding 0.25 mg per ml of culture fluid of a dry powder which was capable of forming a stable oil-in-water emulsion with 40 times its weight of crude oil.

Notwithstanding the many publications on the subject, however, microbially-induced emulsification of oil is poorly understood from both mechanistic and teleological points of view. Microorganisms can utilize crude oil as a substrate for growth with or without concomitant oil emulsification. Where emulsification has occurred because of the production of extracellular emulsifying agents, in general the preparations have not been purified sufficiently to identify the active components. In sum, none of these extracellular bioemulsifiers has been well characterized and very little is known about their chemical properties, mode of action or biological function.

SUMMARY OF THE INVENTION

The present invention is based upon part of a multitude of discoveries made in connection with further work done on the bioemulsifiers produced by Acinetobacter Sp. ATCC 31012, among the most important of which discoveries were:

Firstly, that the Acinetobacter bioemulsifier previously produced by growing Acinetobacter Sp. ATCC 31012 (also known as strain RAG-1) on crude oil or hexadecane is an extracellular microbial protein-associated lipopolysaccharide (which we have herein called "$\beta$-emulsan" and given the common name "protoemulsans"), in which the lipopolysaccharide is an N- and O-lipoacylated heteropolysaccharide made up of major amounts of D-galactosamine and an aminouronic acid, the O-lipoacyl portion of the lipoheteropolysaccharide containing from 2 to 3 percent by weight of various fatty acid esters in which (a) the fatty acids contain from about 10 to about 18 carbon atoms; and (b) less than 50 percent by weight of such fatty acids are composed of 2-hydroxydodecanoic acid and 3-hydroxydodecanoic acid;

Secondly, that growth of Acinetobacter Sp. ATCC 31012 on certain other hydrocarbons or on certain oxygen-containing carbonaceous compounds as the primary assimilable carbon course yields a significantly different extracellular microbial protein-associated lipopolysaccharide (which we have herein called "$\alpha$-emulsans" and given the common name "neoemulsans"), in which the lipopolysaccharide is also an N- and O-lipoacylated heteropolysaccharide made up of major amounts of D-galactosamine and an aminouronic acid, but in which the O-lipoacyl portion of the lipoheteropolysaccharide contains at least 5 percent by weight (and, more often, between 7 to 14 percent by weight and occasionally as high as 19 percent by weight) of various fatty acid esters in which (a) the fatty acids contain from about 10 to about 18 carbon atoms which are usually distributed in different ratios than those in the low-ester $\beta$-emulsans; and (b) about 50 percent by weight or more of such fatty acids are composed of 2-hydroxydodecanoic acid and 3-hydroxydodecanoic acid;

Thirdly, that α-emulsans are much more effective than β-emulsans in the emulsification of various crude oils and gas-oils and, in some instances (such as the emulsification of Bunker C fuel oil), efficiently form stable emulsions where β-emulsans have no effect;

Fourthly, that both α-emulsans and β-emulsans exhibit specificity in the emulsification of various types of hydrocarbons;

Fifthly, that upon deproteinization of the emulsans all of the emulsifying activity is in the respective N- and O-lipoacyl heteropolysaccharides (which we have herein generically called "apoemulsans", and specifically called "apo-α-emulsan" or "apo-β-emulsan" depending upon the particular emulsan from which such deproteinized derivative was formed);

Sixthly, that base hydrolyses of α-emulsan and β-emulsan under mild conditions yield a common derivative (which we have herein called "Ψ-emulsans" and given the common name "pseudoemulsans") which retains about 50 percent of the emulsifying activity of the α-emulsans, the structure of which ψ-emulsans is the N-acylated poly[D-galactosamine/aminouronic acid]in which (a) the amount of fatty acid esters is between 0 and 1 percent by weight of the polysaccharide; and (b) part of the N-acyl groups are 3-hydroxydodecanoyl groups;

Seventhly, that base hydrolyses of α-emulsan and β-emulsan under strong conditions yield a derivative (which we have herein called "proemulsans") which has no emulsifying activity and which is structurally a partially N-acylated poly[D-galactosamine/aminouronic acid];

Eighthly, that antibodies prepared against β-emulsan cross-react in an identical fashion with α-emulsan, apo-α-emulsan, apo-β-emulsan, ψ-emulsan and proemulsan, indicating that the emulsans and their deproteinized and partially deacylated derivatives have approximately the same polymer backbones, which are poly[D-galactosamine/aminouronic acid] polymers;

Ninthly, that the emulsans and their respective deproteinized derivatives are not affected by high concentrations of sodium chloride but require small amounts (from 1 to 100 mM and preferably from 5 to 40 mM) of at least one divalent cation, such as magnesium, calcium or manganese, to function effectively as emulsifying agents for hydrocarbon substrates, which divalent cations are present in sea water, connate water and most "hard" water but must be added to "soft" water;

Tenthly, that emulsans on a weight-for-weight basis are probably the most efficient oil-in-water emulsifiers discovered and, moreover, possess certain characteristics that permit these unique extracellular microbial polysaccharides to be widely used in cleaning oil-contaminated vessels, oil spill management, and enhanced oil recovery by chemical flooding;

Finally, that the emulsans and their deproteinized and deacylated derivatives are strongly adsorbed onto aluminosilicate ion-exchangers and are unusually efficient bioflocculents which may be used to mediate flocculation of various types of aluminosilicate clays, such as kaolin and bentonite.

Based on some of these discoveries, the invention provides several new classes of extracellular microbial lipopolysaccharides and their derivatives selected from the group consisting of (a) the extracellular microbial protein-associated lipopolysaccharides (herein collectively called "α-emulsans") produced by Acinetobacter Sp. ATCC 31012 and its mutants, in which the lipopolysaccharide components (herein collectively called "apo-α-emulsans") are completely N-acylated and partially O-acylated heteropolysaccharides made up of major amounts of D-galactosamine and an aminouronic acid, such apo-α-emulsans containing at least 5 percent by weight of fatty acid esters in which (1) the fatty acids contain from about 10 to about 18 carbon atoms; and (2) about 50 percent by weight or more of such fatty acids are composed of 2-hydroxydodecanoic acid and 3-hydroxydodecanoic acid;

(b) the deproteinized extracellular microbial lipopolysaccharides (herein collectively called "apo-α-emulsans") obtained from the α-emulsans produced by Acinetobacter Sp. ATCC 31012 and its mutants, the apo-α-emulsans being completely N-acylated and partially O-acylated heteropolysaccharides made up of major amounts of D-galactosamine and an aminouronic acid, the apo-α-emulsans containing at least 5 percent by weight of fatty acid esters in which (1) the fatty acids contain from about 10 to about 18 carbon atoms; and (2) about 50 percent by weight or more of such fatty acids are composed of 2-hydroxydodecanoic acid and 3-hydroxydodecanoic acid;

(c) the deproteinized extracellular microbial polysaccharides (herein collectively called "apo-β-emulsans") obtained from the β-emulsans produced by Acinetobacter Sp. ATCC 31012 and its mutants, the apo-β-emulsans being completely N-acylated and partially O-acylated heteropolysaccharides made up of major amounts of D-galactosamine and an aminouronic acid, the apo-β-emulsans containing not more than 5 percent by weight of fatty acid esters in which (i) the fatty acids contain from about 10 to about 18 carbon atoms; and (2) less than 50 percent by weight of such fatty acids are composed of 2-hydroxydodecanoic acid and 3-hydroxydodecanoic acid;

(d) the O-deacylated extracellular protein-associated microbial polysaccharides (herein collectively called the "ψ-emulsans") obtained from the emulsans produced by Acinetobacter Sp. ATCC 31012 and its mutants, the protein-free components of such ψ-emulsans being completely N-acylated heteropolysaccharides made up of major amounts of D-galactosamine and an aminouronic acid and containing from 0 to 1 percent by weight of fatty acid esters in which, when present, the fatty acids contain from about 10 to about 18 carbon atoms;

(e) the deproteinized O-deacylated extracellular microbial polysaccharides (herein collectively called the "apo-ψ-emulsans") derived from either α-emulsans, β-emulsans, ψ-emulsans, apo-α-emulsans or apo-β-emulsans, the apo-ψ-emulsans being completely N-acylated heteropolysaccharides made up of major amounts of D-galactosamine and an aminouronic acid and containing from 0 to 1 percent by weight of fatty acid esters in which, when present, the fatty acids contain from about 10 to about 18 carbon atoms;

(f) the deproteinized O-deacylated extracellular microbial polysaccharides (herein collectively called the "proemulsans") derived from either α-emulsans, β-emulsans, ψ-emulsans, apo-α-emulsans, apo-β-emulsans or apo-ψ-emulsans, the proemulsans being poly[D-galactosamine/amino uronic acid]biopolymers in which (1) none of the hydroxy group are acylated; and (2) from none to all of the amino groups are acylated; and (g) the divalent metal, ammonium and quaternary ammonium salts of such α-emulsans, apo-α-emulsans, apo-β-emulsans, ψ-emulsans, apo-ψ-emulsans and proemulsans.

The invention further provides emulsifying agents comprising an aqueous solution in sea water or fresh water containing from about 10 mcg/ml to about 20 mg/ml of such α-emulsans, and from about 1 to about 100 mM of at least one divalent cation. Using the data contained herein, the emulsifying agents of the invention may be used, among other things, (1) for cleaning hydrocarbonaceous residues, including residual petroleum, from tankers, barges, storage tanks, tank cars and trucks, pipelines and other containers; (2) for cleaning oil spills which are floating on the sea or which have been washed ashore or which are deposited on land; and (3) for the enhanced recovery of oil by chemical flooding techniques, particularly with respect to those petroleum reservoirs located in sand or sandstone or limestone formations.

The invention also contemplates those polyanionic heteropolysaccharides biopolymers which are produced microbiologically (regardless of the organism used) or by semi-synthetic techniques (such as by anzymatic activity) and in which (a) substantially all of the sugar moieties are N-acylated amino sugars, a portion of which is N-acylated D-galactosamine and another portion of which is an aminouronic acid (such as D-galactosamineuronic acid, D-glucoseamineuronic acid), a part of the N-acyl groups of such heteropolysaccharide being N-(3-hydroxydodecanoid) groups; and (b) at least 0.2, and preferably from about 0.5 to about 0.75 micromoles per milligram of such heteropolysaccharide consists of fatty acid esters in which (1) the fatty acids contain from about 10 to about 18 carbon atoms, and (2) about 50 percent by weight of such fatty acids are composed of 2-hydroxydodecanoic acid and 3-hydroxydodecanoic acid.

NOMENCLATURE

A new lexicon has been used herein to identify and refer to the various types of extracellular microbial polysaccharides and their semi-synthetic derivatives which are derived from Acinetobacter Sp. ATCC 31012 and its mutants. These new words are "emulsans", "α-emulsans", "β-emulsans", "ψ-emulsans", "apoemulsans", "apo-α-emulsans", "apo-β-emulsans", "apo-ψ-emulsans", and "proemulsans", which are defined as follows:

The name "emulsans", which reflects the polysaccharide structure of these compounds and the exceptional emulsifying activity of the biologically produced materials, has been created to identify generically those extracellular microbial protein-associated lipoheteropolysaccharides produced by Acinetobacter Sp. ATCC 31012 and its mutants, which may be subdivided into the α-emulsans and the β-emulsans. The name "apoemulsan", the prefix of which is derived from the Greek word απο meaning "from", has been created to identify generically those deproteinized lipopolysaccharides obtained from the emulsans.

The name "α-emulsans" defines those extracellular microbial protein-associated lipopolysaccharides produced by Acinetobacter Sp. ATCC 31012 and its mutants in which the lipopolysaccharide components (i.e., without the associated protein) are completely N-acylated and partially O-acylated heteropolysaccharides made up of major amounts of D-galactosamine and an aminouronic acid, the lipopolysaccharide components containing at least 5 percent by weight of fatty acid esters in which (1) the fatty acids contain from about 10 to about 18 carbon atoms; and (2) about 50 percent by weight or more of such fatty acids are composed of 2-hydroxydodecanoic acid and 3-hydroxydodecanoic acid. It follows, therefore, that the deproteinized α-emulsan are named "apo-α-emulsans".

The name "β-emulsans" defines those extracellular microbial protein-associated lipopolysaccharides produced by Acinetobacter Sp. ATCC 31012 and its mutants in which the lipopolysaccharide components (i.e., without the associated protein) are completely N-acylated and partially O-acylated heteropolysaccharides made up of major amounts of D-galactosamine and an aminouronic acid, the lipopolysaccharide components containing less than 5 percent by weight of fatty acid esters in which (1) the fatty acids contain from about 10 to about 18 carbon atoms; and (2) less than 50 percent by weight of such fatty acids are composed of 2-hydroxydodecanoic acid. The deproteinized β-emulsans are named "apo-β-emulsans".

The name "ψ-emulsans" defines the O-deacylated extracellular protein-associated microbial polysaccharides obtained from the emulsans, the protein-free components of such ψ-emulsans being completely N-acylated heteropolysaccharides made up of major amounts of D-galactosamine and an aminouronic acid and containing from 0 to 1 percent of fatty acid esters in which, when present, the fatty acids contain from about 10 to about 18 carbon atoms. These protein-free components are named "apo-ψ-emulsans", regardless of how they are prepared.

The name "proemulsans" defines the deproteinized O-deacylated extracellular microbial polysaccharide in which the poly[D-galactosamine/aminouronic acid]biopolymers are characterized by (1) none of the hydroxy groups being acylated; and (2) from none to all of the amino groups being acylated. The proemulsans have no emulsifying activity under the standard assay techniques described below.

From the data described herein, it is now known that the bioemulsifiers which were inherently formed in the experimental work previously published concerning the growth of RAG-1 on crude oil or hexadecane were β-emulsans in which the lipopolysaccharide contained from 2 to 3 percent by weight of fatty acid esters. The β-emulsans, therefore have been given the common name "protoemulsans", the prefix of which is derived from the Greek word προτο meaning "first".

The α-emulsans have been given the common name "neoemulsans", the prefix having derived from the Greek word ηεοζ meaning "new". Because the ψ-emulsans have only about one-half the emulsifying activity of the α-emulsans, the ψ-emulsans have been given the common name "pseudoemulsans".

As used herein, the term "Actinetobacter Sp. ATCC 31012 and its mutants" refers not only to the organism (i.e., strain RAG-1) described below in Section 6.1 and its spontaneous and chemically- and physically-induced mutants and recombinants which produce emulsans, but to all microorganisms (whatever the genus) derived by using recombinant DNA techniques to insert genetic information from strain RAG-1 and such mutants which are responsible for the production of the bioemulsifiers into the DNA-based genetic code of such "recombined" microorganisms such that they are capable of biosynthesizing α-emulsans or β-emulsans (or the apoemulsans), depending upon the primary assimilable carbon source used to grow the organism.

BRIEF DESCRIPTION OF THE DRAWINGS

To more fully comprehend the invention, reference should be made to the accompanying drawings, in which

FIGS. 6A and 6B, is a graphical representation of the kinetics of the emulsan-induced emulsification of gas-oil, showing the relationship between the emulsification of varying concentrations of gas-oil as a function of time for a given concentration of the bioemulsifier;

FIGS. 10A and 10B, is a graphical representation of the relative stabilities of emulsan-induced emulsions of gas-oil, showing the relationship between percentage change in emulsification as a function of standing time of the emulsion for a given concentration of bioemulsifier and varying weight ratios of gas-oil/bioemulsifier;

PRODUCTION OF EMULSANS AND APOEMULSANS

Figure 1:
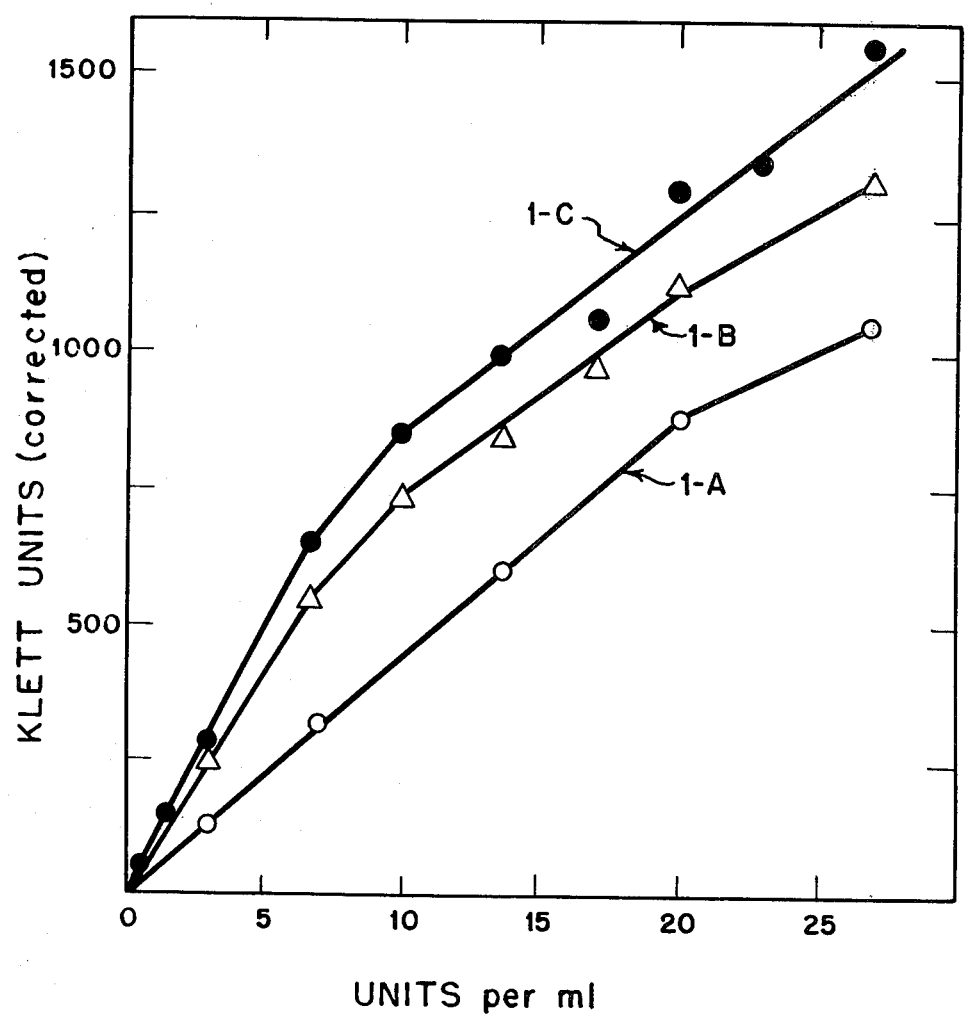
FIG. 1 is a graphical representation of the standard emulsifier assay described below in Section 6.4.1, showing the relationship between the amount of emulsification which is obtained with gas-oil and with a 1:1 (v/v) mixture of hexadecane/2-methylnaphthalene as a function of the emulsan concentration.

Emulsans may be produced by aerobically growing Acinetobacter Sp. ATCC 31012 or its mutants on an aqueous fermentation medium which contains (a) a growth-sustaining amount of a utilizable carbon source on which the organism will not only grow but will also produce the desired emulsan (such as α-emulsan) rather than the low-ester protoemulsan; (b) growth-sustaining amounts of nitrogen- and phosphorous-containing compounds to furnish these essential nutrients to the organism; and (c) from about 1 to about 100 mM of a divalent cation, such as magnesium, calcium or manganese, which must be added to the fermentation medium if not present. Apoemulsans, in turn, are produced by deproteinization of the emulsans in such manner that the lipoheterpolysaccharide does not undergo degradation.

The fermentation process may be conducted with automatic or manual control in batch or continuous fermenters, using either fresh water or sea water media. Selection of suitable fermentation equipment may be made from designs engineered to give the most efficient oxygen transfer to the biomass at lowest operating cost. In addition to the stirred tank fermenters, other types of fermenters may be used, such as thin channel fermenters, tubular loop fermenters, film fermenters, recirculating tower fermenters, deep shaft fermenters, and jet fermenters, the most important criteria being efficiency in the fermentation process, especially with respect to oxygen transfer and power consumption.

Some of the more important process parameters for the production and purification of $\alpha$-emulsans and apo-$\alpha$-emulsans are discussed in more detail below.

ACINETOBACTER SP. ATCC 31012

The microorganism used to produce both neoemulsans and protoemulsans from utilizable carbon sources is Acinetobacter Sp. ATCC 31012 (also known as strain RAG-1), which has been deposited previously with the American Type Culture Collection, Rockville, Md. This organism, which has been described by A. Reisfeld et al., Appl. Microbiol., 24, 363 (1972) as well as by U.S. Pat. No. 3,941,692, has the following characteristics:

During the exponential growth phase the cells appear mostly as irregular short rods, 0.9 to 1.2 by 1.5 to 3.0 mcm (mcm=$10^{-6}$ m). The cells occur often as V-shaped pairs, indicating snapping division. Occasionally, the rods are slightly bent or swollen. Coccoid cells, approximately 1.2 mcm in diameter, are characteristic of stationary phase cultures. The cocci are gram-positive; the rods are gram-negative.

Agar colonies: circular, glistening and smooth, up to 5.0 mm in diameter; gelatin is liquified; starch is not hydrolyzed; indole and hydrogen peroxide are not produced; nitrites are produced from nitrate only when the cells are grown in citrate medium containing potassium nitrate; urease is not produced; catalase-positive; aerobic; hemolysis of rabbit blood agar; citrate can serve as the sole carbon and energy source; no acid from glucose, cellulose, maltose, lactose, rhamnose, sucrose or mannitol; optimum temperature 30° to 35° C.

The amount of inoculum used to initiate the fermentation will be dependent upon the type of fermentation equipment used. For optimum results in batch-type stirred fermenters, growth should be initiated with late exponential cultures grown under similar fermentation conditions, preferably in an amount from about 1% to about 5% (v/v) of the fermentation medium.

6.2. FERMENTATION MEDIA

6.2.1. UTILIZABLE CARBON SOURCES

Even though it has previously been reported by A. Horowitz et al., Appl. Microbiol, 30, 10 (1975), that strain RAG-1 will grow on many different carbon compounds on sea water agar media supplemented with the carbon source, such growth has no relationship with whether or not the organism will produce any type of Acinetobacter bioemulsifier (which, when produced, usually occurs during the exponential growth phase), much less the high-ester $\alpha$-emulsans. Moreover, even in those instances where the organism does produce extracellular lipopolysaccharides, there does not appear to be any correlation between the structure of the utilizable carbon source and what type of extracellular lipopolysaccharide will be biosynthesized from such carbon source, whether the high-ester $\alpha$-emulsans or the low-ester $\beta$-emulsans. For example, growth of Acinetobacter Sp. ATCC 31012 on ethanol, sodium palmitate or dodecane results in the formation of $\alpha$-emulsans with each such carbon source, with ethanol media yielding $\alpha$-emulsans with the highest ester content in the lipoacyl portion of the lipoheteropolysaccharide, while growth of the organism under substantially identical conditions using pentadecane, hexadecane or heptadecane results only in the formation of $\beta$-emulsans. In general, where a utilizable carbon source can be transformed into $\alpha$-emulsans by the organism, the total yield of the extracellular lipopolysaccharide per liter of culture medium will be greater than when the organism produces $\beta$-emulsans from a different carbon source.

$\alpha$-Emulsans produced by aerobically growing Acinetobacter Sp. ATCC 31012 on ethanol media in accordance with the invention are unusually efficient bioemulsifiers, exhibiting a high degree of specificity in emulsifying those hydrocarbon substrates (such as crude oils, gas-oils and Bunker C fuel oils) that contain both aliphatic and aromatic components. For optimum results in batch-type stirred fermenters, the initial media should contain about 1.25% to about 3% (v/v) and preferably about 1.75% to about 2.5% (v/v) of ethanol, with make-up ethanol added during the fermentation at a rate sufficient to sustain maximum growth and $\alpha$-emulsan formation, since the production of $\alpha$-emulsans by the organism has been found to occur during the growth period.

6.2.2. ADDITIONAL NUTRIENTS

Maximum growth of Acinetobacter Sp. ATCC 31012 on a utilizable carbon source to produce $\alpha$-emulsans or $\beta$-emulsans requires more than growth-sustaining amounts of one or more nitrogen-containing compounds to furnish this essential nutrient to the organism and to enable the organism to grow and to produce the biopolymer, which contains major amount of two amino sugars. Additionally, phosphorus-containing compounds are also essential nutrients. Suitable sources of available nitrogen include ammonium salts, such as ammonium sulfate or ammonium chloride; nitrates, such as ammonium nitrate or sodium nitrate; or organic sources of available nitrogen, such as urea or soybean meal. Suitable sources of available phosphorus include dibasic potassium phosphate, monobasic potassium phosphate and the like. In addition, liquid fertilizers, such as 12-6-6 or 8-8-8, may serve as a source of nitrogen and phosphorous nutrients for the growth of Acinetobacter Sp. ATCC 31012.

6.2.3. DIVALENT CATIONS

As shown below in the data set forth in Section 8.4, the emulsifying activity of both types of Acinetobacter bioemulsifiers is dependent above pH 6 upon divalent cations, such as magnesium ions, calcium ions or manganese ions. These divalent cations are present in sea water or "hard" water when fermentation media are prepared from such sources. When "soft" fresh water or distilled water are used to prepare the fermentation media, then small amounts of one or more salts of a divalent cation should be added to the fermentation media, the concentration being such that the resultant culture media will contain from about 1 to about 100 mM (and preferably from about 5 to about 40 mM) of at least one divalent cation.

6.3. FERMENTATION PROCESS CONDITIONS

Maximum growth of Acinetobacter Sp. ATCC 31012 upon utilizable carbon sources to produce α-emulsans requires selection of the best conditions of aeration, agitation, temperature and pH under which the highest possible oxygen transfer can be obtained consistent with the physiology of the organism. Discussed below are the best conditions which have been found for consistently producing 4 to 5 mg/ml of α-emulsans from ethanol media in conventional 60-liter stirred fermenters. These conditions probably will undergo subtle or pronounced changes to obtain higher yields upon large-scale production in fermenters specifically designed or adapted to give more efficient oxygen transfer at the lowest power consumption. Subsequent work on optimizing the process will, of course, focus on (a) consumption of the substrate, which is a function of the physiology of Acinetobacter Sp. ATCC 31012 and its mutants; (b) consumption of oxygen, which is a function of oxygen diffusion to the cells which, in turn, will be influenced (i) by making the surface through which the diffusion occurs as large as possible (i.e., dispersing the gas phase as finely as possible in the liquid phase to create a large gas hold-up), (ii) by increasing the driving force of the diffusion (such as by increasing the pressure in the fermenter or by using oxygen-enriched air), and (iii) by allowing the diffusion constant to be as high as possible (i.e., by minimally decreasing the diffusion constant by the use of chemical antifoam agents); and (c) exothermic heat production, which necessitates a properly designed cooling system on scale-up.

6.3.1. AERATION

Using 60-liter stirred fermenters with the fermentation medium and process conditions described below in Section 13.1, maximum production of α-emulsans occurs when 15 liters of air per minute are passed through the 40 liters of fermentation medium, which corresponds to an oxygen flow rate of 189.6 millimoles per liter per hour. This oxygen flow rate is not limiting but can, if necessary, be increased to as high as 700 millimoles per liter per hour, or even higher, with the more efficiently designed fermenters.

6.3.2. AGITATION

To promote maximum oxygen diffusion to the cell mass, the fermentation media must be agitated either by stirring or circulating the media through the fermenter, depending upon the type of fermentation equipment employed. Using 60-liter stirred fermenters with the fermentation medium and other process conditions described below in Section 13.1, maximum production of α-emulsans occurs when the medium is agitated at a rate of 250 rpm. This value is not limiting but will be varied in the more efficiently designed fermenters to achieve maximum oxygen transfer at the lowest power consumption.

6.3.3. TEMPERATURE AND pH

Although the fermentation process may be conducted over a wide range of temperatures, best results have been obtained in the production of α-emulsans when the fermentation is conducted at 30° C. The pH of the fermentation medium should be maintained between 6 and 7, and preferably between 6.2 and 6.7 during the exponential growth phase, which necessitates the addition of sufficient base (preferably ammonia).

6.3.4. DEFOAMING

Stirred-tank fermentations of Acinetobacter Sp. ATCC 31012 on utilizable carbon sources to produce α-emulsans invariably are accompanied by foaming problems, which diminish the realizable yield of the extracellular lipopolysaccharide. Although many types of chemical defoamers may be used in the fermentation media, great care must be taken when adding chemical defoaming agents to keep the diffusion constant as high as possible. Using the 60-liter stirred fermenters with the fermentation medium and other process conditions described below in Section 13.1, maximum production of α-emulsans occurs when there were automatic pulse additions (whenever foam levels reached a predetermined height) of a silicone defoamant, preferably Dow-Corning 525 (sterilizable), diluted 1:8. Upon scale-up of the fermentation process, it is expected that a combination of chemical and mechanical methods will give optimum results in defoaming the nutrient solutions on which α-emulsans will be produced from Acinetobacter Sp. ATCC 31012 and its mutants.

6.4. EXTRACELLULAR PRODUCTION OF BIOEMULSIFIERS

Data is presented below with respect to both types of extracellular lipopolysaccharides (α-emulsans and β-emulsans) produced by Acinetobacter Sp. ATCC 31012 so that the similarities as well as differences between these biopolymers may be understood. Unless the particular type of extracellular lipopolysaccharide produced by the organism is identified by name, the phrase "Acinetobacter bioemulsifier" refers collectively to both α-emulsans and β-emulsans.

6.4.1. STANDARD ASSAY FOR EMULSIFYING ACTIVITY

In order to study the kinetics of bioemulsifier production by Acinetobacter Sp. ATCC 31012 and to compare the emulsifying activities of α-emulsans and β-emulsans, a series of simple sensitive assays for these bioemulsifiers were developed. These assays were based upon the large increase in turbidity of a mixture of oil and water arising from the emulsion of the hydrocarbon in the aqueous phase.

The first assay involved the emulsification of gas-oil in sea water under standardized conditions and subsequent measurement of turbidity. When it was found that sea water could be replaced in the assay procedure with dilute solutions of magnesium salts (cf/Section 8.4), a second assay was developed involving emulsification of gas-oil in 10 mM of magnesium sulfate at pH 7.2. Finally, after it was found that the bioemulsifiers exhibited a degree of specificity toward different classes of hydrocarbon substrates (cf/Section 9), totally defined conditions were developed using a mixture of hexadecane and 2-methylnaphthalene in place of gas-oil and buffered magnesium sulfate (or magnesium chloride) in place of sea water.

Each assay technique consisted of adding hydrocarbon (0.05 ml of gas-oil or 0.1 ml of 1:1 (v/v) hexadecane/2-methylnaphthalene) to 7.5 ml of filtered sea water or 7.5 ml of Tris-Mg buffer [20 mM tris-(hydroxymethyl)aminomethane hydrochloride, pH 7.2, supplemented with 10 mM magnesium sulfate] containing 1 to 25 units of bioemulsifier per ml (about 3 to 75 mcg/ml of bioemulsifier) in a 125 ml flask. After reciprocal shaking (150 strokes per minute) for one hour at 26° C., contents of the flask were transferred to Klett tubes for measurement of turbidity in a Klett-Summerson colorimeter fitted with a green filter. Appropriate dilutions were made in water so that the final readings were between 30 and 150 Klett units, and values for Klett units reported as final readings times the dilution. Values for controls containing no bioemulsifier (5 to 20 Klett units) were subtracted. One unit of bioemulsifier per ml is defined as that amount of activity which yields 100 Klett units using 0.1 ml of 1:1 (v/v) hexadecane/2-methylnaphthalene and 7.5 ml of Tris-Mg buffer. Specific Emulsification Activity (or specific activity) is units per mg of bioemulsifier, dry weight basis.

FIG. 1 graphically illustrates standard curves obtained when all three assay techniques were applied to an α-emulsan produced by growing Acinetobacter Sp. ATCC 31012 at 30° C. in a reciprocally shaken flask on a medium containing 1.0% (v/v) ethanol, 0.125% urea, 0.125% magnesium sulfate [MgSO$_4$.7H$_2$O], 0.0002% ferrous sulfate [FeSO$_4$.7H$_2$O], 0.001% calcium chloride (anhyd), 0.025% dibasic potassium phosphate, and 0.2 M Tris HCl buffer, pH 7.4. The preparation of α-emulsan used in preparing such curves had a Specific Emulsification Activity of 330 units per mg. Curve 1-A represents the relationship between the amount of emulsification between 0.05 ml Gach-Saran gas-oil and 7.5 ml of filtered sea water; Curve 1-B represents the relationship between the amount of emulsification between 0.05 ml Gach-Saran gas-oil and 7.5 ml Tris-Mg buffer; and Curve 1-C represents the relationship between the amount of emulsification between 0.1 ml 1:1 (v/v) hexadecane/2-methylnaphthalene and 7.5 ml Tris-Mg buffer, all as a function of α-emulsan concentration. Each point in FIG. 1 represents the average of 3 to 4 determinations. These standard curves were then used to determine the emulsifying activity of preparations of crude and purified emulsans (α-emulsans, β-emulsans and the semi-synthetic ψ-emulsans) and apoemulsans (apo-α-emulsans, apo-β-emulsans and apo-ψ-emulsans). Characterization of a particular Acinetobacter bioemulsifier as an α-emulsan or a β-emulsan is based on chemical analysis of the fatty acid esters contained in the lipoacyl portions of the protein-extracted lipopolysaccharides.

6.4.2. EXTRACELLULAR PRODUCTION OF α-EMULSANS

Measurement of extracellular emulsifying activity was determined at different stages of growth of Acinetobacter Sp. ATCC 31012 in an ethanol medium, the fermentation conditions being identical to those used to prepare the α-emulsan used for the standard assay tests. Growth was estimated by turbidity using a Klett-Summerson colorimeter fitted with a green filter or a Gilford Spectrophotometer (Model 240). One hundred Klett units of exponentially growing Acinetobacter Sp. ATCC 31012 correspond to an absorbance at 620 nm (1-cm light path) of 0.816 and a biomass of 0.37 g per liter (dried at 90° C. for 16 hours).

Figure 2:
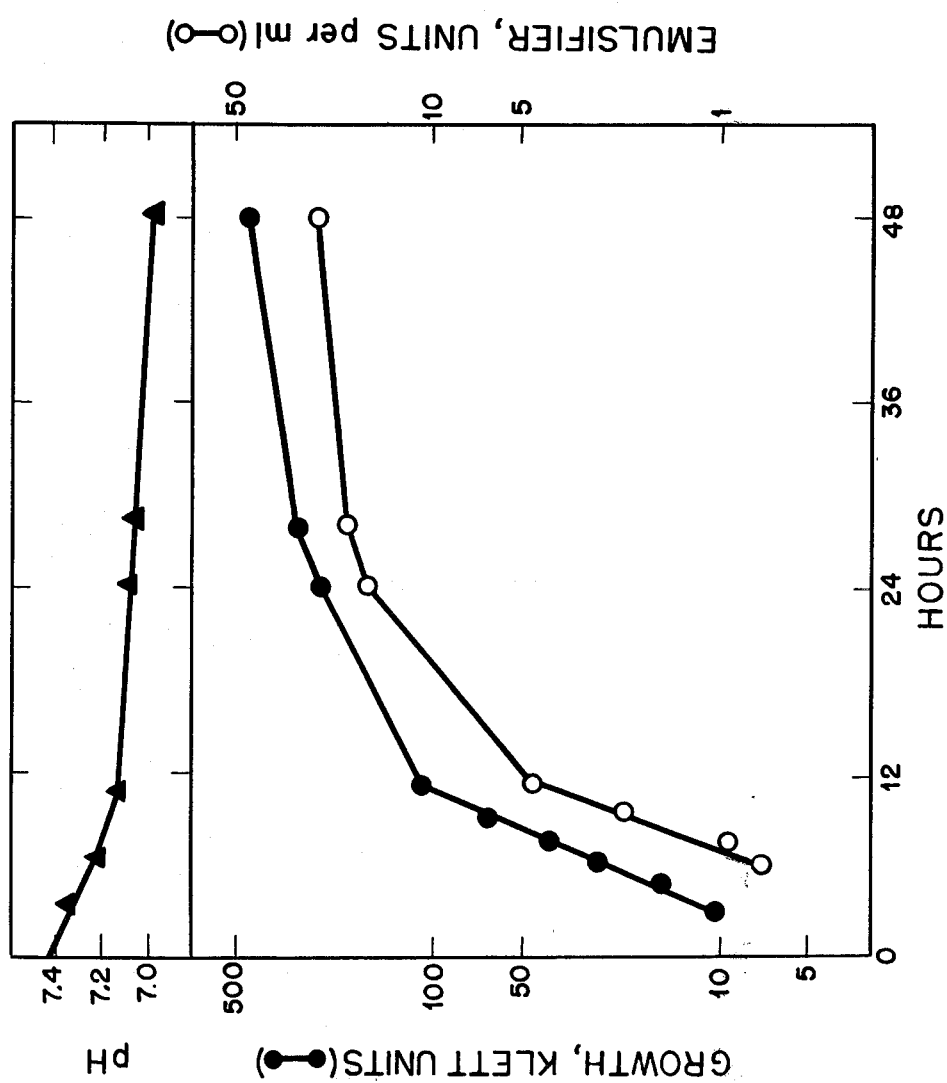
FIG. 2 is a graphical representation of the extracellular production of α-emulsan during growth of Acinetobacter Sp. ATCC 31012 on an ethanol medium, showing the relationship of the growth of the organism in such medium, the production of the bioemulsifier during such growth, and the change of pH during such growth, all as a function of time.

FIG. 2 shows the relationship between the growth of Acinetobacter Sp. ATCC 31012 on the ethanol medium, the production of the bioemulsifier (α-emulsan) during such growth, and the change of pH during such growth, all as a function of time. Although these data are limited to the production of α-emulsan in a shaking flask fermentation with a particular ethanol medium, FIG. 2 illustrates the general rule that the production of α-emulsan occurs during the growth phase.

6.4.3. EXTRACELLULAR PRODUCTION OF β-EMULSANS

Measurement of extracellular emulsifying activity was also determined at different stages of growth of Acinetobacter Sp. ATCC 31012 in a hexadecane medium, the medium and fermentation conditions being identical to those used to prepare the emulsan used for the standard assay tests except that 0.2% (v/v) hexadecane medium was used in place of ethanol as the carbon source. Viable cell number was determined by spreading 0.1 ml of an appropriate dilution on ACYE agar, which contained 0.5% sodium acetate, 0.1% yeast extract (Difco), 0.125% urea, 0.025% dibasic potassium phosphate and 1.5% agar (Difco). Plates were incubated at 32° C. for 3 days.

Figure 3:
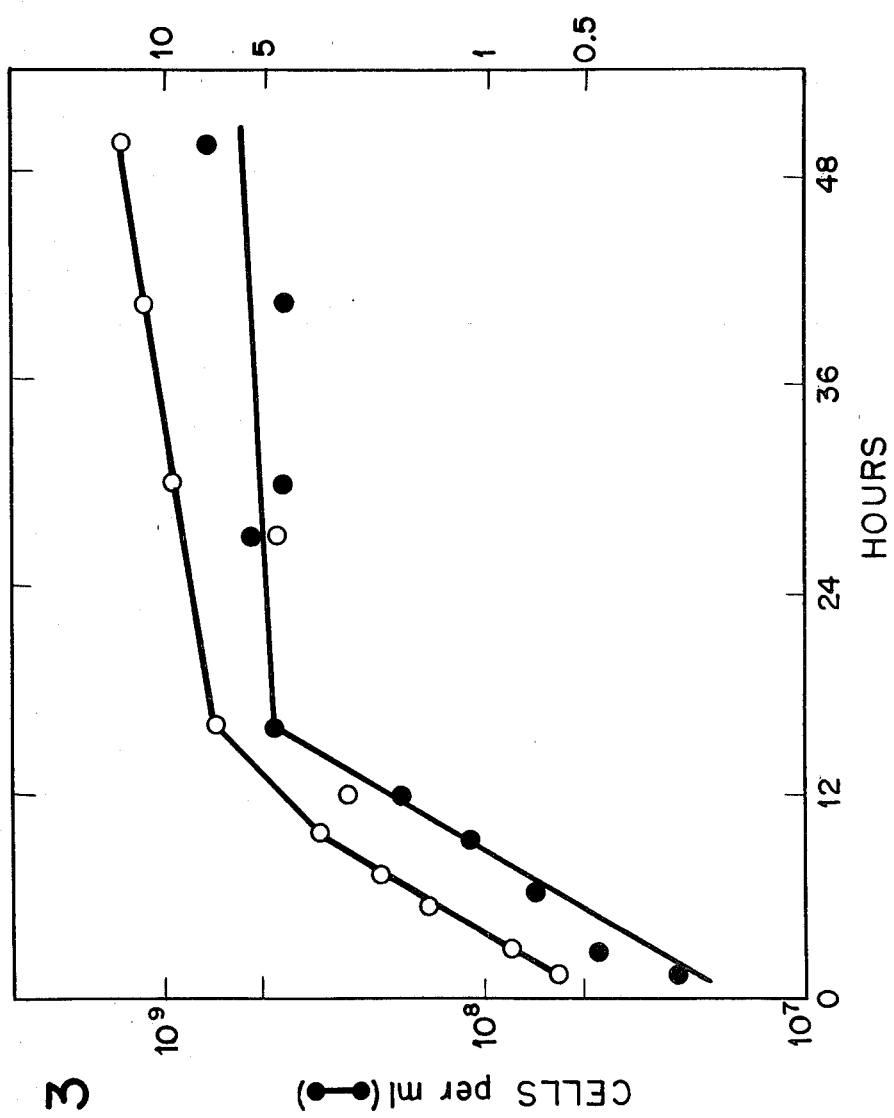
FIG. 3 is a graphical representation of the extracellular production of β-emulsan during growth of Acinetobacter Sp. ATCC 31012 on a hexadecane medium, showing the relationship of the growth of the organism in such medium and the production of the bioemulsifier during such growth, both as a function of time.

FIG. 3 shows the relationship between the growth of Acinetobacter Sp. ATCC 31012 on the hexadecane medium and the production of the bioemulsifier (β-emulsan) during such growth. The data contained in FIG. 3 is similarly limited to the production of β-emulsan in a shaking flask fermentation with a particular hexadecane medium, and shows that the production of β-emulsan also occurs during the growth period.

6.4.4. DISTRIBUTION OF EMULSIFYING ACTIVITY IN FRACTIONS OF GROWTH CULTURE

After 40 hours of incubation of Acinetobacter Sp. ATCC 31012 in the ethanol medium and in the hexadecane medium as described above in Sections 6.3.2 and 6.3.3, respectively, each culture was centrifuged as 10,000 x g for 15 minutes and the pellets washed once with Tris-Mg buffer. The pellicle formed during centrifugation of the hexadecane culture was removed, washed twice with growth medium before assaying for activity. Emulsifying activity in each fraction for the ethanol and hexadecane growth cultures was assayed by the standard assay technique described above in Section 6.4.1 and illustrated in FIG. 1. The results of such assays are summarized in Table I.

TABLE I

Distribution of Emulsifying Activity in Fractions of Growth Cultures

| Fraction | Emulsifier (units/ml) | |
|---|---|---|
| | Ethanol Substrate | Hexadecane Substrate |
| Pellet | 7 | 0 |
| Supernatant fluid | 23 | 14 |
| Pellicle | — | 0 |

The data contained in Table I show that over 75% of the activity was extracellular when ethanol was the substrate, while all of the measurable activity was extracellular when Acinetobacter Sp. ATCC 31012 was grown on hexadecane medium. The small amount of activity associated with the pellet fraction was variable; in certain cases no measurable cell-bound activity could be found. Disruption of the pellet fractions by sonic oscillation did not release additional emulsifying activity.

6.5. DEPROTEINIZATION

Apoemulsans may be prepared by deproteinization of the particular emulsans, which technique was used to isolate and purify samples of the chemical characterization of both Acinetobacter bioemulsifiers described below. The associated protein may be separated from both bioemulsifiers by the hot phenol extraction technique described by O. Westphal et al. in the monograph edited by R. L. Whistler, entitled "Carbohydrate Chemistry", Academic Press, Inc., New York, pp. 83-91. Alternatively, the protein fraction may be removed enzymatically by proteolytic digestion.

6.6. ISOLATION AND PURIFICATION

The extracellular protein-associated lipopolysaccharides produced by Acinetobacter Sp. ATCC 31012 and their respective deproteinized derivatives may be isolated and purified by various procedures, including selective precipitation, selective solvent extraction or partitioning or selective adsorption onto a solid adsorbant followed by subsequent elution or extraction. For many industrial uses, isolation and purification of the Acinetobacter bioemulsifiers is not necessary, since the cell-free growth media may be used directly. For the purposes of determining their respective structures as well as their chemical and physical properties, particularly with respect to emulsifying activity, the $\alpha$-emulsans and $\beta$-emulsans produced by Acinetobacter Sp. ATCC 31012 have been isolated and purified. Three different procedures have been followed, including (a) heptane partitioning of the crude extracellular lipopolysaccharide from the fermentation medium, followed by extraction of impurities from the heptane-partitioned biopolymer and subsequent work-up; (b) precipitation of the extracellular lipopolysaccharide by ammonium sulfate, followed by work-up of the precipitate; and (c) precipitation of the extracellular lipopolysaccharide by a detergent quaternary ammonium cation followed by work-up of the precipitate. Each of these techniques is equally applicable to the isolation and purification of the respective apoemulsans.

6.6.1. HEPTANE PARTITIONING

Because the Acinetobacter bioemulsifiers exhibit specificity with respect to the structurally different types of hydrocarbon substrates which may be emulsified (cf/Section 9), certain water-immiscible hydrocarbons may be used to selectively extract the extracellular lipopolysaccharide from the fermentation media without creating a stable emulsion. By way of illustration, heptane extraction of the cell-free culture medium from which etherextractibles had been removed suspended over 90% of extracellular lipopolysaccharide at the heptane/water interface. After evaporation of the heptane, and preferably further solvent extraction with ether, the resultant product is a viscous syrup which can be dissolved in 50% aqueous methanol, the impurities removed by dialysis and the remaining material recovered by lyophilization. In a typical example using this heptane partitioning technique, a purified $\beta$-emulsan was prepared which was characterized by a specific activity of 205 units per mg.

6.6.2. AMMONIUM SULFATE PRECIPITATION

The addition of ammonium sulfate to the fermentation broth has been used to fractionally precipitate the extracellular lipopolysaccharides from the culture medium, from which the concentrate may be recovered and further treated to remove impurities. By way of illustration, addition of ammonium sulfate to cell-free supernatant fluids has resulted in the precipitation of substantially all of the extracellular lipopolysaccharides when the concentration of ammonium sulfate is increased from 30% saturation to a final concentration of 40% saturation. The resulting precipitate, which may be collected by centrifugation, has been extracted by ether to remove impurities, dialyzed against water and lyophilized, yielding the purified extracellular lipopolysaccharide. In a typical example using this ammonium sulfate precipitation technique, a purified $\alpha$-emulsan was prepared which was characterized by a specific activity of 330 units per mg.

6.6.3. QUATERNARY AMMONIUM PRECIPITATION

Because the extracellular lipopolysaccharides produced by Acinetobacter Sp. ATCC 31012 were found to be anionic biopolymers, a procedure was developed to precipitate the anionic biopolymer with a cationic detergent, such as cetyltrimethyl ammonium bromide, from which precipitate the detergent cation could be separated while leaving the purified extracellular lipopolysaccharide. For example, the addition of cetyltrimethyl ammonium bromide to an aqueous solution of $\alpha$-emulsan immediately forms a precipitate which is recoverable by centrifugation or filtration. This precipitate is soluble in 0.1 M sodium sulfate, from which solution cetyltrimethyl ammonium iodide precipitates upon addition of potassium iodide, leaving the $\alpha$-emulsan in the supernatant fluid. Dialysis of this supernatant fluid against distilled water, followed by lyophilization, has yielded highly purified samples of $\alpha$-emulsan as a white solid, with a specific activity of 350 units per mg.

7. CHEMICAL AND PHYSICAL PROPERTIES OF EMULSANS AND APOEMULSANS

Chemical and physical characterization of emulsans and apoemulsans were measured on samples which had been purified to apparent homogeneity, from which characterization conclusions were reached on the structure of these unique extracellular lipopolysaccharides. Such information is necessary to give a better understanding of the relationship between the molecular structure of this class of bioemulsifiers and their specificity in emulsifying various hydrocarbon substrates.

7.1. PREPARATION OF SAMPLES FOR ANALYTICAL CHARACTERIZATION

7.1.1. PREPARATION OF EMULSAN SAMPLES

The emulsan samples used for chemical and physical characterization were prepared by aerobically growing Acinetobacter Sp. ATCC 31012 on an ethanol medium ($\alpha$-emulsan) or a hexadecane medium ($\beta$-emulsan) and were purified by precipitation between 30-40% ammonium sulfate saturation, followed by extraction with ether, dialysis against distilled water and lyophilization, as described more fully in the example set forth below in Section 13.7. Some samples of $\alpha$-emulsan were further purified by employing the cetyltrimethyl ammonium bromide precipitation technique, as described more fully in the example set forth below in Section 13.11.

7.1.2. PREPARATION OF APOEMULSAN SAMPLES

The apoemulsan samples used for chemical and physical characterization were prepared by hot phenol extraction of the associated protein moiety from the emulsan samples. The deproteinization procedure, which is described more fully in the examples set forth below in Sections 13.6 and 13.7, involved adding a dilute solution (5 mg/ml) of emulsan preheated to 65°–68° C. to an equal volume of 90% phenol at 65° C., stirring the mixture for 15 minutes while maintaining the temperature at 65° C., and then cooling the mixture to 10° C. in an ice bath. The resulting emulsion was then centrifuged to separate the denatured protein in the phenol phase from the apoemulsan in the aqueous phase. After transferring the viscous aqueous phase to a flask, the phenol layer and phenol/water interface were extracted three more times with water, following which the combined water extracts were dialyzed extensively against several changes of distilled water and then freeze-dried, yielding 85% by weight of apoemulsan based on the weight of the emulsan. All of the emulsifying activity was in the recovered emulsan. None of the emulsifying activity was in the denatured protein fraction.

7.1.3. AMMONIUM SULFATE FRACTIONATION OF APO-α-EMULSAN

To assure homogeneity of the apo-α-emulsan, the deproteinization procedure was repeated on another sample of α-emulsan which had been prepared by aerobically growing Acinetobacter Sp. ATCC 31012 on an ethanol medium and which had been purified by precipitation between 30–40% ammonium sulfate fractionation, followed by extraction with ether, dialysis against distilled water and lyophilization. After three phenol extractions, the combined water extracts were extracted four times with an equal volume of ether to remove residual phenol. Following evaporation of any retained ether, the viscous aqueous phase was cooled to 5° C. and brought to 32.5% ammonium sulfate saturation. After standing for one hour at 5° C., the clear translucent precipitate was collected at centrifugation at 5,000×g for 30 minutes at 5° C. The procedure was repeated to obtain a slightly turbid second precipitate between 32.5% and 35% ammonium sulfate saturation and another small precipitate between 35% and 40% ammonium sulfate saturation. No additional precipitate formed between 40% and 60% saturation.

Each of the precipitates was dissolved in water and was then dialyzed at 2°–5° C. successively against distilled water, 0.05 N hydrochloric acid for 24 hours and double distilled water, following which each of the resulting solutions were freeze-dried. Over 99% of the emulsifying activity of the apo-α-emulsan was found in the two fractions which precipitated between 30% and 35% ammonium sulfate saturation. These two fractions contained similar specific activities and exhibited substantially the same chemical composition. In addition, both fractions were homogeneous when examined by immunodiffusion against antibodies prepared against β-emulsan, each giving a single identical band upon Ouchterlony two-dimensional diffusion. Accordingly, the two fractions were combined for certain of the chemical and physical characterizations, the combined fractions when used being identified herein as "apo-α-emulsan-WA".

7.1.4. QUATERNARY AMMONIUM SALT PRECIPITATION OF APO-α-EMULSAN

To cross-check the analytical data on apo-α-emulsan-WA, another highly purified sample of apo-α-emulsan was prepared using (1) the identical hot phenol extraction of another sample of α-emulsan which had been prepared by aerobically growing Acinetobacter Sp. ATCC 31012 on an ethanol medium, followed by (2) cetyltrimethyl ammonium bromide precipitation of the resultant apo-α-emulsan, dissolving the precipitate in 0.1 M sodium sulfate, and addition of potassium iodide to the solution to precipitate cetyltrimethyl ammonium iodide. The supernatant fluid contained the apo-α-emulsan. Extensive dialysis of this supernatant fluid against distilled water followed by lyophilization yielded a highly purified apo-α-emulsan which was designated as "apo-α-emulsan-CTAB".

7.2. CHEMICAL CHARACTERIZATION

7.2.1. CHEMICAL COMPOSITION OF EMULSANS AND APOEMULSANS

Elemental analyses of α-emulsan and apo-α-emulsan, which were performed on samples of α-emulsan and apo-α-emulsan-WA that had been dried to constant weight at 55° C. in vacuo (the apo-α-emulsan-WA sample having released 12.7% water on such drying), are shown in Table II.

TABLE II

| Sample | Elemental Composition of Emulsan | | | | |
|---|---|---|---|---|---|
| | % C | % H | % N | % S | % Ash |
| α-Emulsan | 41.72 | 6.95 | 7.74 | 0.7 | 13.8 |
| Apo-α-emulsan-WA | 46.70 | 7.01 | 6.06 | 0.0 | 3.5 |

The deproteinized sample (apo-α-emulsan-WA) contained significantly less N, S and ash than emulsan. The C:N:R ratio of apo-α-emulsan-WA was calculated to be 9.0:1.0:16.1. No significant quantities (<0.5%) of phosphorous or halides were found in either sample. Functional group tests were positive for carboxyl and ester groups and negative for methoxy and ethoxy groups. The polymer contained less than 0.02 micromoles reducing sugar per mg, which was the sensitivity of the test employed. The nonreducing polymer was resistant to high temperatures in neutral and alkaline conditions. No emulsifying activity was lost at 100° C. for 2 hours in distilled water; 50% of the activity remained even after treatment in 1 N sodium hydroxide at 100° C. for 1 hour. Apo-α-emulsan-WA was considerably more sensitive to acid, losing 50% of its emulsifying activity in 2 minutes at 100° C. in 1 N hydrochloride acid.

Titration of apo-α-emulsan-WA (40 mg/4 ml) between pH 2.5–10.5 showed a single inflection point, corresponding to pK=3.05 (identical to a standard sample of glucuronic acid). Apo-α-emulsan-WA consumed 0.24 micromoles periodate per mg, (which would suggest the presence of a small amount of glucose in the polymer), which was subsequently determined to be due to a small amount of glucose present in an ammonium sulfate co-precipitated extracellular polysaccharide which possessed no emulsifying activity. Periodate uptake ceased after two hours at 30° C., pH 4.5. The periodate treated material did not lose any emulsifying activity, further indicating that no glucose was present in the apo-α-emulsan.

7.2.2. ALKALINE HYDROLYSIS OF APOEMULSAN

Two hundred milligrams of apo-α-emulsan-WA were refluxed in 40 ml of 1 N sodium hydroxide for 4 hours, cooled, extracted three times with 40 ml ether, acidified to pH 1–2 with concentrated hydrochloric acid, and extracted again three times with 40 ml ether. The acid-ether extracts were combined and dried in a tared flask, yielding 30 mg (15%) fatty acids; extraction with ether prior to acidification yielded less than 2 mg dry material. Combining the weight recovery of fatty acid from the polymer (150 mcg/mg) and the O-ester content (0.65 micromoles/mg) yields an average equivalent weight of 231 for the fatty acids.

7.2.3. ACID HYDROLYSIS OF APOEMULSAN

Preliminary hydrolysis studies were performed on apo-α-emulsan at 80° C. and 100° C. in sealed tubes with concentrations of hydrochloric acid varying from 0.01–6.0 M. After removal of hydrogen chloride in vacuo, the products were examined for reducing power, amino sugars and by paper chromatography in n-butanol/pyridine/water (6:4:3, v/v) [Solvent A] and in n-propanol/ethyl acetate/water (7:1:2, v/v) [Solvent B].

Figure 4:
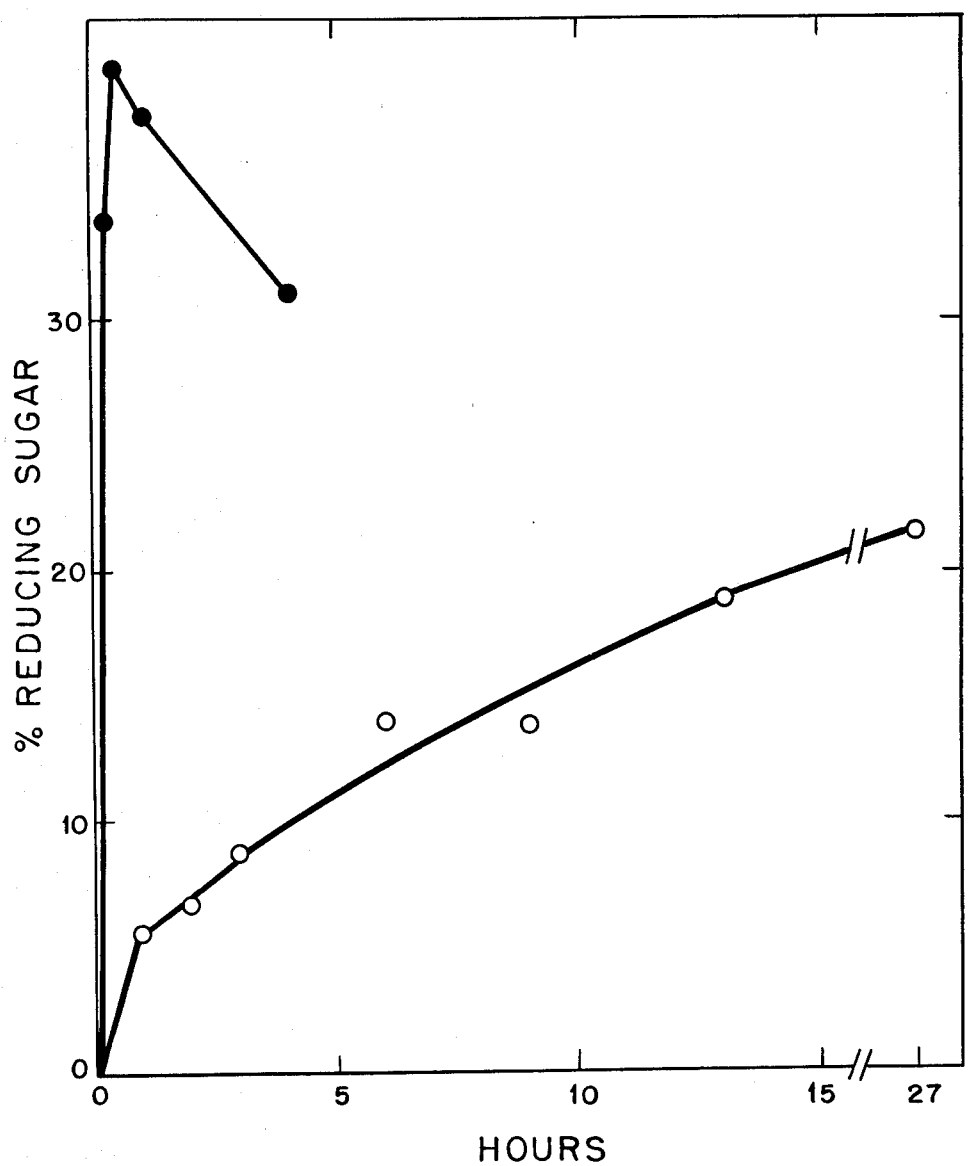
FIG. 4 is a graphical representation of the changes which occur on acid hydrolysis of apo-α-emulsan, showing the relationship between the weight percent of reducing power of the acid-hydrolyzed deproteinized O-lipoacylated heteropolysaccharide as a function of the duration of hydrolysis.

FIG. 4 is a graphical representation of the changes which occur on acid hydrolysis of apo-α-emulsan. The weight percent of reducing power is plotted against the duration of hydrolysis at 100° C. at 0.05 M HCl (shown in the lower curve) at 5 M HCl (shown in the upper curve). Hydrolyses were performed in sealed tubes under nitrogen on 1 mg/ml samples of apo-α-emulsan. As shown in FIG. 4, at 0.05 M hydrochloric acid at 100° C. there was a release of around 6% reducing sugar during the first hour, followed by a slower release of about 1% reducing sugar per hour for the next 20 hours.

After 27-hour hydrolysis in 0.05 M HCl at 100° C., chromatography revealed the presence of two major reducing spots (subsequently identified as galactosamine and an aminouronic acid) and one minor component (subsequently identified as glucose). [N.B.-Analytical work done much later on CTAB-fractionated material indicates that the presence of glucose was due to an impurity which was co-precipitated during the ammonium sulfate fractionation of apo-α-emulsan.] In addition, there were considerable amounts of incompletely hydrolyzed material (remaining near the origin). After 5-hour hydrolysis in 0.05 M HCl, only glucose was detected on the chromatograms. N-acetylated derivatives of the amino sugars were never detected.

Maximum amount of reducing sugar was obtained by hydrolyzing apo-α-emulsan in 5 M HCl at 100° C. for 30 minutes. Even under these conditions significant amounts of emulsifying agent were incompletely hydrolyzed. Longer periods of hydrolysis resulted in further destruction of the sugars. The relative amount of amino sugars to glucose increased with time of hydrolysis due both to the slower release of amino sugars from the polymer and faster destruction of free glucose. Hydrolysis of samples of the ammonium sulfate fractionated apo-α-emulsan-WA showed the same chromatographic pattern as that of apo-α-emulsan; however, when this analysis was repeated on the sugars produced by hydrolysis of apo-α-emulsan-CTAB at 100° C. in 0.05 N and 5 N HCl for the same periods of time, no glucose was detected. Following hydrolysis in 5 M HCl at 100° C. for 30 minutes, apo-α-emulsan-WA released 37.6% reducing sugar and 24.4% total hexosamines (in both cases, using galactosamine as the standard).

7.2.4. IDENTIFICATION OF SUGAR COMPONENTS

Table III summarizes the data that led to the conclusion that the sugars produced by hydrolysis of ammonium sulfate fractionated apo-α-emulsan were D-glucose (minor), D-galactosamine (major) and an aminouronic acid (major). Unknown compound A did not separate from glucose in solvents A or B and yielded a positive D-glucose reaction directly on the paper. Unknown compound B migrated identically to galactosamine in solvent B, gave a positive D-galactose oxidase reaction and was converted to lyxose ($R_{Glc}=1.49$ in solvent B) by ninhydrin degradation. Unknown compound C gave positive reactions for reducing sugar, amino sugar and carboxylate ion. Moreover, it was similar both in chromatographic behavior and in its reaction with the nitrous acid-indole test to 2-amino-2-deoxyhexuronic acids.

TABLE III

Properties of Sugar Products of Hydrolysis of Ammonium Sulfate Fractionated Apo-α-Emulsan

| Component[a] | $R_{Glc}$[b] | Positive reactions[c] |
|---|---|---|
| Standards: | | |
| D-glucose | 1.25 | glucose oxidase |
| D-galactose | 1.22 | galactose oxidase |
| D-glucosamine | 1.00 | ninhydrin (purple), EM, glucose oxidase |
| D-galactosamine | 0.85 | ninhydrin (purple), EM, galactose oxidase |
| D-N—acetylgalactosamine | 1.58 | EM |
| Acid hydrolysis products of apo-α-emulsan: | | |
| A | 1.25 | glucose oxidase |
| B | 0.85 | ninhydrin (purple), EM galactose oxidase |
| C | 0.23 | ninhydrin (greenish-yellow, later blue), EM |

[a]Obtained after 24 hour hydrolysis of apo-α-emulsan in 0.05 M HCl at 100° C.
[b]Rate of movement of each sugar relative to glucosamine in solvent A.
[c]All components gave positive alkaline silver nitrate tests. Spot tests were determined directly on the chromatograms. EM is the modified Elson and Morgan reagent [R.W. Wheat in the monograph edited by E. F. Neufeld et al., "Methods in Enzymology", Vol. VIII, Academic Press Inc., New York, pp. 60-78.

Based on all the evidence, therefore, it is certain that the polymer is poly[D-galactosamine/aminouronic acid]. Any glucose present is probably an impurity.

7.2.5. IDENTIFICATION OF FATTY ACIDS

As a general rule, the esterified fatty acid content of apo-α-emulsans derived from the deproteinization of α-emulsans prepared by aerobically growing Acinetobacter Sp. ATCC 31012 on an ethanol medium is in the range from about 7% to about 15%, corresponding to about 0.3 to about 0.7 micromoles per milligram of fatty acid esters in which the fatty acids have an average equivalent weight from about 200 to about 230. Alkaline hydrolysis, acidification and ether extraction of α-emulsan yields a mixture of fatty acids, the infrared spectrum of which exhibited absorption peaks at 3610 cm$^{-1}$ (nonbonded O-H), 3500 cm$^{-1}$ (bonded O-H), 1705 cm$^{-1}$ (C=O) and 1050 cm$^{-1}$ (C-OH). The NMR spectrum in CDCl$_3$ indicated that the mixture consisted mainly of saturated and hydroxy-substituted fatty acids.

Base hydrolysis of one gram of α-emulsan was performed in 400 ml of 2.5% potassium hydroxide in 90% methanol under reflux for 4 hours. After removal of the methanol in vacuo, 500 ml of water were added. The clear alkaline solution was washed three times with 150 ml of ether, the ether discarded, and the aqueous solution acidified to pH 2 with hydrochloric acid. The acid solution was then extracted five times with 100 ml ether, the interphase in each extraction being set aside. The combined interphase fractions were treated with acetone to precipitate protein and polysaccharide. After removal of the precipitate by filtration and the acetone by distillation in vacuo, the aqueous phase was again extracted with ether. The combined ether extracts were dried over magnesium sulfate. Removal of the ether left 130 mg (13% yield) of a mixture of fatty acids. The methyl esters of the fatty acid mixture was prepared with diazomethane by standard techniques.

Gas liquid chromatography of the methyl esters of the fatty acid mixture led to the separation of eleven peaks, nine of which were identified by comparison of retention volumes of pure samples of known structure. Table IV sets forth the relative retention volumes of the methyl esters of the fatty cids obtained from emulsan.

TABLE IV

Fatty Acid Methyl Esters Obtained from Mild Base Hydrolysis of χ-Emulsan

| Peak No. | Fatty Acid Methyl Ester | Relative Retention Volume |
|---|---|---|
| 1 | Decanoic | 0.17 |
| 2 | Dodecanoic | 0.29 |
| 3 | Dodecenoic | 0.34 |
| 4 | Unidentified | 0.48 |
| 5 | Unidentified | 0.61 |
| 6 | Hexadecanoic | 1.00 |
| 7 | Hexadecenoic | 1.14 |
| 8 | 2-Hydroxydodecanoic | 1.30 |
| 9 | 3-Hydroxydodecanoic | 1.69 |
| 10 | Octadecanoic | 1.94 |
| 11 | Octadecenoic | 2.16 |

Although the relative amounts of fatty acids will vary from sample to sample, in general, the two hydroxydodecanoic acids comprise from about 50% to about 70% of the aggregate fatty acids, with 3-hydroxydodecanoic acid usually predominating over 2-hydroxydodecanoic acid. Table V sets forth the fatty acid composition of the α-emulsan described above.

TABLE V

Typical Fatty Acid Ester Composition of α-Emulsan

| Fatty Acid | Percent of Total Fatty Acids |
|---|---|
| Decanoic | 11.4 |
| Dodecanoic | 23.0 |
| Dodecenoic | 2.4 |
| 2-Hydroxydodecanoic | 10.5 |
| 3-Hydroxydodecanoic | 39.5 |
| Hexadecanoic | 0.7 |
| Hexadecenoic | trace |
| Octadecanoic | 0.3 |
| Octadecenoic | trace |
| Unidentified | 12.0 |

The acetone-precipitated polysaccharide remaining after O-deacylation of the α-emulsan by mild base hydrolysis was redissolved in water, dialyzed extensively against water, lyophilized and then subjected to acid hydrolysis for 6 hours at 98° C. in 5 M HCl. The aqueous hydrolysate was extracted with ether and the ether extract was treated by diazomethane to convert to methyl esters whatever fatty acids remained after such strong acid hydrolysis. Gas chromatographic analysis of this material revealed the presence of methyl 3-hydroxydodecanoate as the only fatty acid. This showed that N-(3-hydroxydodecanoyl) groups were also present in ψ-emulsan.

7.3. PHYSICAL CHARACTERIZATION

Preliminary experiments indicated that the purified α-emulsan was excluded by Sephadex G-100 and G-200 and did not pass an Amicon XM-30 filter. This data, coupled with the fact that apo-α-emulsan contained 1.5 micromoles of carboxylic groups per mg, suggested that the lipopolysaccharide was an anionic polymer. Additional data on physical characterization is set forth below:

7.3.1. INTRINSIC AND REDUCED VISCOSITY

Figure 5:
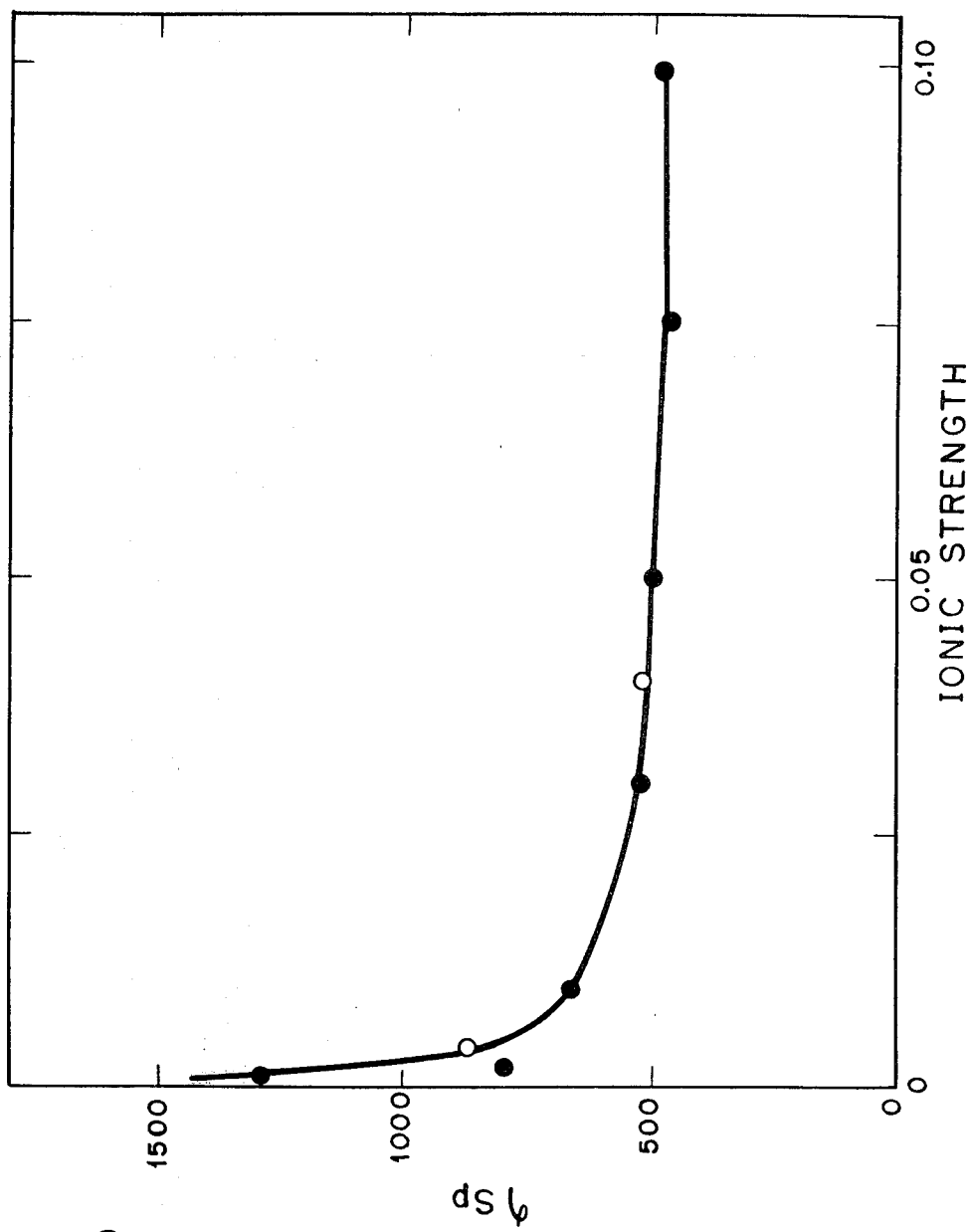
FIG. 5 is a graphical representation of the relationship of the reduced viscosity of apo-α-emulsan as a function of ionic strength.

The intrinsic viscosities of the analytical samples of α-emulsan, apo-α-emulsan and apo-α-emulsan-WA in 0.15 M Tris buffer, pH 7.4, were 470, 505 and 750 cc per gm, respectively. With all three samples, reduced viscosity was independent of concentration between 0.05 and 1.0 mg per ml. Exposure of 0.5 mg per ml apo-α-emulsan to sonic oscillations (Branson B12 sonifier, setting 8, 14 min) reduced the reduced viscosity to 420 cc per gm. Exposure for an additional 20 minutes did not further reduce the viscosity. The viscosity of apo-α-emulsan as a function of ionic strength is shown in FIG. 5. Between 0.03–0.15 M NaCl, reduced viscosity decreased slightly from 515 to 480 cc per gm. The large increase in reduced viscosity at low ionic strengths is characteristic of polyelectrolytes and have been attributed to dilution of counterions. Reduced viscosity was also measured as a function of pH using 0.05 M citrate-phosphate buffer (pH 3–7) and 0.05 M Tris HCl buffer (pH 6.8–8.5). Throughout the entire range (pH 3–8.5) the reduced viscosity of α-emulsan remained at $480 \pm 50$ cc per gm.

7.3.2. SEDIMENTATION VELOCITY ANALYSIS

Sedimentation velocity analysis of 2 mg/ml of apo-α-emulsan-WA in 0.15 M NaCl showed a single broad band corresponding to an $s_{20} = 6.06 \times 10^{-13}$ sec or 6.06 S. The diffusion coefficient, D, also determined in the analytical centrifuge was $5.25 \times 10^{-8}$ cm$^2$ sec$^{-1}$. The partial specific volume of the material, V, was 0.712 cm$^3$ g$^{-1}$.

7.3.3. ESTIMATION OF MOLECULAR WEIGHT

Estimating the molecular weight of apo-α-emulsan-WA from the equation, $M = RTs/D(1-V\rho)$, where R is the gas constant, T is the absolute temperature and $\rho$ is the density of the solution, yields a weight average molecular weight of $9.76 \times 10^5$. Alternatively, the molecular weight can be estimated using the determined values for intrinsic viscosity, η, sedimentation constant, S, and partial molar volume, V, according to the equation of Scheraga and Mandelkern [J. Am. Chem. Soc., 75, 179 (1953)]. The calculated viscosity average molecular weight for apo-α-emulsan-WA was $9.88 \times 10^5$.

7.3.4. SPECTRAL PROPERTIES

The ultraviolet absorption spectrum of apo-α-emulsan-WA (220–350 nm) showed no maxima. The infrared spectrum of apo-α-emulsan incorporated into a KBr pellet or nugol revealed the following groups: 3340 cm$^{-1}$ (O-H), 2900 cm$^{-1}$ (C-H), 1720 cm$^{-1}$, weak (C=O), 1640 cm$^1$ (amide I) and 1545 cm$^{-1}$ (amide II). X-ray diffraction analysis of apo-α-emulsan, which was performed on a film formed by evaporation of a water solution of apoemulsan, showed crystallinity. Table VI summarizes the 2θ angles and d spacings measured for the X-ray diffraction pattern recorded with Ni filtered CuKα radiation.

TABLE VI

X-Ray Diffraction Analysis of Apo-α-emulsan

| 2θ° | d(A) | I(rel.) |
|---|---|---|
| 21.00 | 4.23 | S |
| 16.70 | 5.31 | W |
| 14.80 | 5.99 | VW |
| 13.04 | 6.79 | W |
| 10.66 | 8.30 | W |
| 7.18 | 12.30 | S |

7.4. CONCLUSIONS ON STRUCTURE

The foregoing data show that apo-α-emulsan is a highly acidic lipopolysaccharide with a molecular weight average close to one million. Molecular weight determination from sedimentation and diffusion data closely fit the value obtained from a consideration of sedimentation and viscosity measurements. In both cases the determined value for the partial molar volume of 0.712 cm$^3$ gm$^{-1}$ was used. The relatively high intrinsic viscosity, low diffusion constant and low sedimentation coefficient of the emulsifier indicate that the shape of apo-α-emulsan is highly asymmetrical. Using Simha's factor [C. Tanford, "Physical Chemistry of Macromolecules", John Wiley and Sons, Inc., New York, 1963, pp. 390–411] for the viscosity increment of rod-shaped ellipsoids indicates that apo-α-emulsan has an axial ratio of close to 100. Preliminary examination of the purified apo-α-emulsan by electron microscopy revealed thin fibers with lengths greater than 1000 A.

Apo-α-emulsan is composed of major amounts of two amino sugars (D-galactosamine and an aminouronic acid) and a mixture of fatty acid esters in which the fatty acids (a) contain from 10 to 18 carbon atoms, and (b) possess an average equivalent weight from about 200 to about 230, about 50% or more of such fatty acids being composed of 2-hydroxydodecanoic acid and 3-hydroxydodecanoic acid, with the latter hydroxy fatty acid predominating.

Titration curves and infrared spectrum of the apo-α-emulsan sample indicate that the amino sugars of the biopolymer are N-acylated. The aminouronic acid content of the apo-α-emulsan sample was estimated by acid-base titration of the biopolymer to be 1.5 micromoles/mg. Assuming the aminouronic acid to be an N-acetylhexosamine uronic acid (M.W.=222), it would comprise 33% by weight of the biopolymer. Direct estimation of D-galactosamine content of the apo-α-emulsan sample is not possible at this time, since hydrolysis conditions necessary to release it from apoemulsan cause considerable decomposition of the amino sugar. Rough estimates (from intensities of reducing and ninhydrin positive materials on chromatograms) indicate that the amount of D-galactosamine is similar to the quantity of aminouronic acid. The total fatty acid ester content of the apo-α-emulsan sample was 15% by weight with an average equivalent weight of about 231. Table VII summarizes the chemical composition of apo-α-emulsan-WA on the basis of all the data.

TABLE VII

Chemical Composition of Apo-α-emulsan-WA

| Component | Apo-α-Emulsan-WA |
|---|---|
| D-galactosamine[a] | 20–30[b] |
| Hexosamine uronic acid[a] | 33.3 |
| D-glucose[c] | 5.2 |
| Fatty acid esters[d] | 15.0 |
| Water | 12.7 |
| Ash | 3.5 |

[a]Calculated as N—acetylated amino sugar.
[b]Estimated from intensity of ninhydrin and reducing spots on chromatograms.
[c]Probably present as an impurity in apo-α-emulsan-WA.
[d]See TABLE V for typical fatty acid distribution.

7.5. VARIATIONS IN STRUCTURE

Table VII summarizes the chemical composition of apo-α-emulsan-WA, which is a highly purified sample free of protein and nucleic acid and which appeared to be homogeneous by several criteria, namely (a) only a single band was found by Ouchterlony two-dimensional diffusion; (b) only a single component was observed by sedimentation velocity studies, using several concentrations of material; and (c) attempts to further purify the material by extraction or precipitation with organic solvents did not improve its specific activity or alter its chemical composition.

Growth of Acinetobacter Sp. ATCC 31012 on a utilizable carbon source (such as ethanol, palmitic acid or dodecane) to produce those bioemulsifiers which are characterized as α-emulsans will yield products in which the O-lipoacylated heteropolysaccharide may deviate from the specific chemical composition for apo-α-emulsan-WA shown in Table VII. As a general rule, the N-acyl and partially O-acyl heteropolysaccharides in the emulsan or constituting the apo-α-emulsan will be composed on a dry weight basis of from about 20% to about 35% by weight of D-galactosamine; from about 30% to about 35% by weight of hexosamine uronic acid; and from about 7% to about 19% by weight of fatty acid esters in which the fatty acids contain from about 10 to about 18 carbon atoms and are characterized by an average equivalent weight from about 200 to about 230, from about 50% to about 70% of such fatty acids in the O-lipoacyl portion of the apo-α-emulsan being composed of 2-hydroxydodecanoic acid and 3-hydroxydodecanoic acid. Although the ratio of 2-hydroxydodecanoic acid to 3-hydroxydodecanoic acid in the O-lipoacyl portion of the apo-α-emulsan (or apo-α-emulsan component if the product is an α-emulsan) may vary from about 1:4 to about 1:1, the 3-hydroxydodecanoic acid will predominate in those biopolymers which have a high Specific Emulsification Activity.

7.6. IMMUNOLOGICAL CHARACTERIZATION

To immunologically characterize the Acinetobacter bioemulsifiers produced by Acinetobacter Sp. ATCC 31012, rabbits were injected with 1 mg of β-emulsan in 1 ml complete Freund adjuvant. The rabbits were bled 11 to 14 days later, from which sera a crude immunoglobulin fraction was obtained by ammonium sulfate fractionation.

Antibodies prepared against β-emulsan cross-react in an identical fashion with α-emulsan, apo-α-emulsan, apo-β-emulsan, ψ-emulsan (produced by mild base hydrolysis of α- or β-emulsan) and proemulsan (produced by strong base hydrolysis of any of the foregoing), indicating that both Acinetobacter bioemulsifiers (α-emulsan and β-emulsan) and their various deproteinated and deacylated derivatives have approximately the same polymer backbone, even though these classes of biopolymers are distinguishable by fatty acid ester content as well as by differences in the distributions of fatty acids, the α-emulsans containing a larger amount and greater proportion of 3-hydroxydodecanoic acid ester than the β-emulsans.

8. EMULSIFYING PROPERTIES

Data are presented below with respect to the emulsifying properties of both types of extracellular lipopolysaccharides (α-emulsans and β-emulsans) produced by Acinetobacter Sp. ATCC 31012 so that similarities as well as differences between these biopolymers may be understood. As before, unless the particular type of extracellular lipopolysaccharide produced by the organism is identified by name, the phrase "Acinetobacter bioemulsifier" refers collectively to both classes of emulsans. Unless otherwise indicated, emulsifying activity was assayed in accordance with the standard assay technique described above in Section 6.4.1 using the standard curves shown in FIG. 1.

8.1. KINETICS OF EMULSAN-INDUCED EMULSION FORMATION

Figure 6:
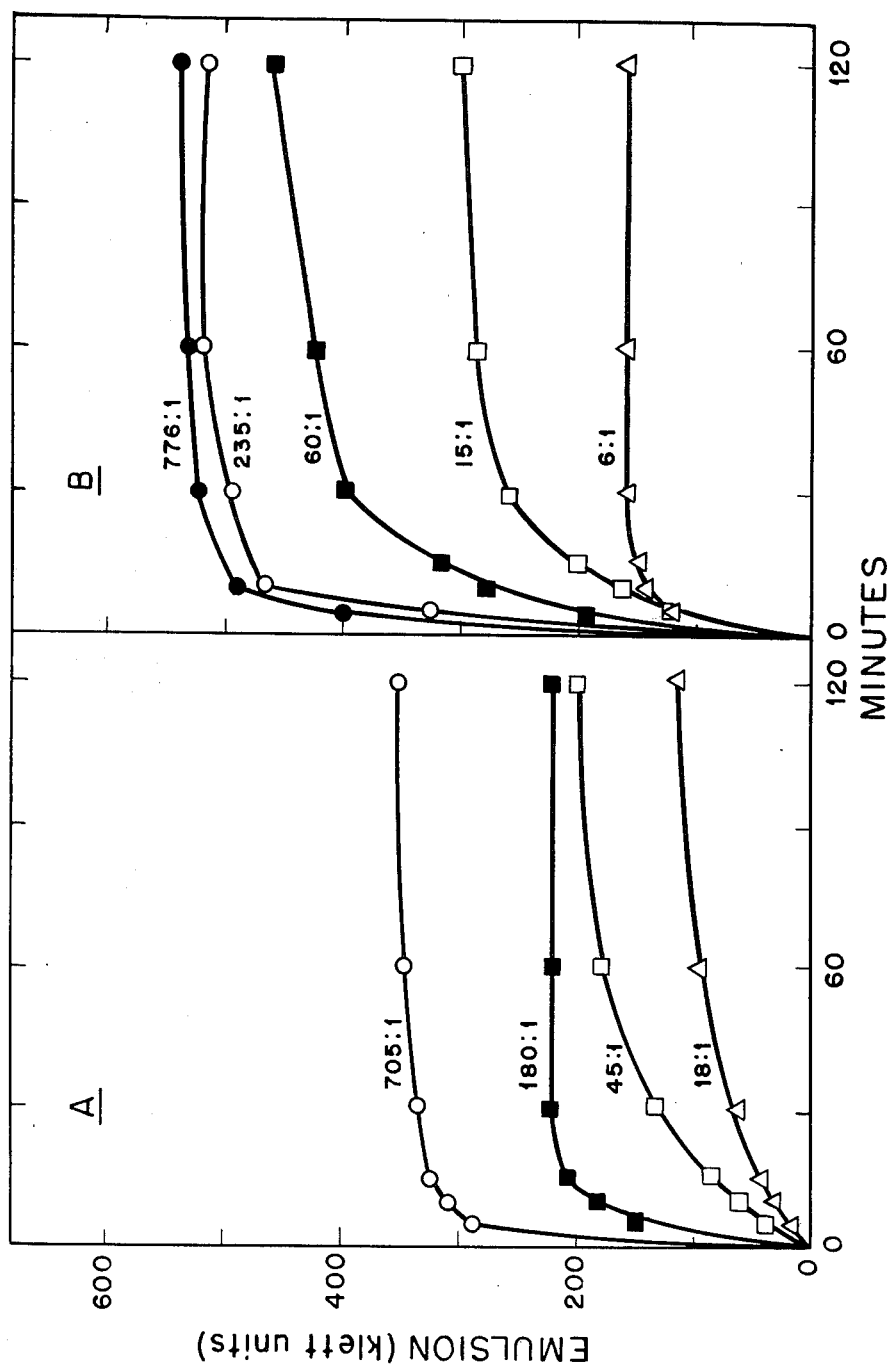
FIG. 6, which is subdivided into

The rate of emulsification of gas-oil by purified Acinetobacter bioemulsifier is summarized in FIG. 6, in which the numbers identifying each curve refer to the weight ratios of gas-oil/bioemulsifier. At fixed concentrations of bioemulsifier (0.25 mg in FIG. 6A and 0.7 mg in FIG. 6B, each in 7.5 ml of filtered sea water), using amounts of gas-oil varying from 4.5 to 582 mg and under the conditions (i.e., reciprocal shaking at 150 strokes per minute for 1 hour at 25° C.) of the standard assay technique, the rate of emulsion formation as well as the final tubidity were proportional to gas-oil concentration between 5 to 100 mg of gas-oil per ml. With 33 or 100 mcg/ml of bioemulsifier and concentrations of gas-oil exceeding 45 mg/ml, half-maximum turbidities were reached in less than 5 minutes. When the bioemulsifier and gas-oil were allowed to interact at 25° C. for 2 hours without shaking, half-maximum turbidities were obtained in less than 2 minutes of shaking. After 60 minutes of shaking, turbidity continued to increase gradually for 4 hours at about 10% per hour.

Figure 7:
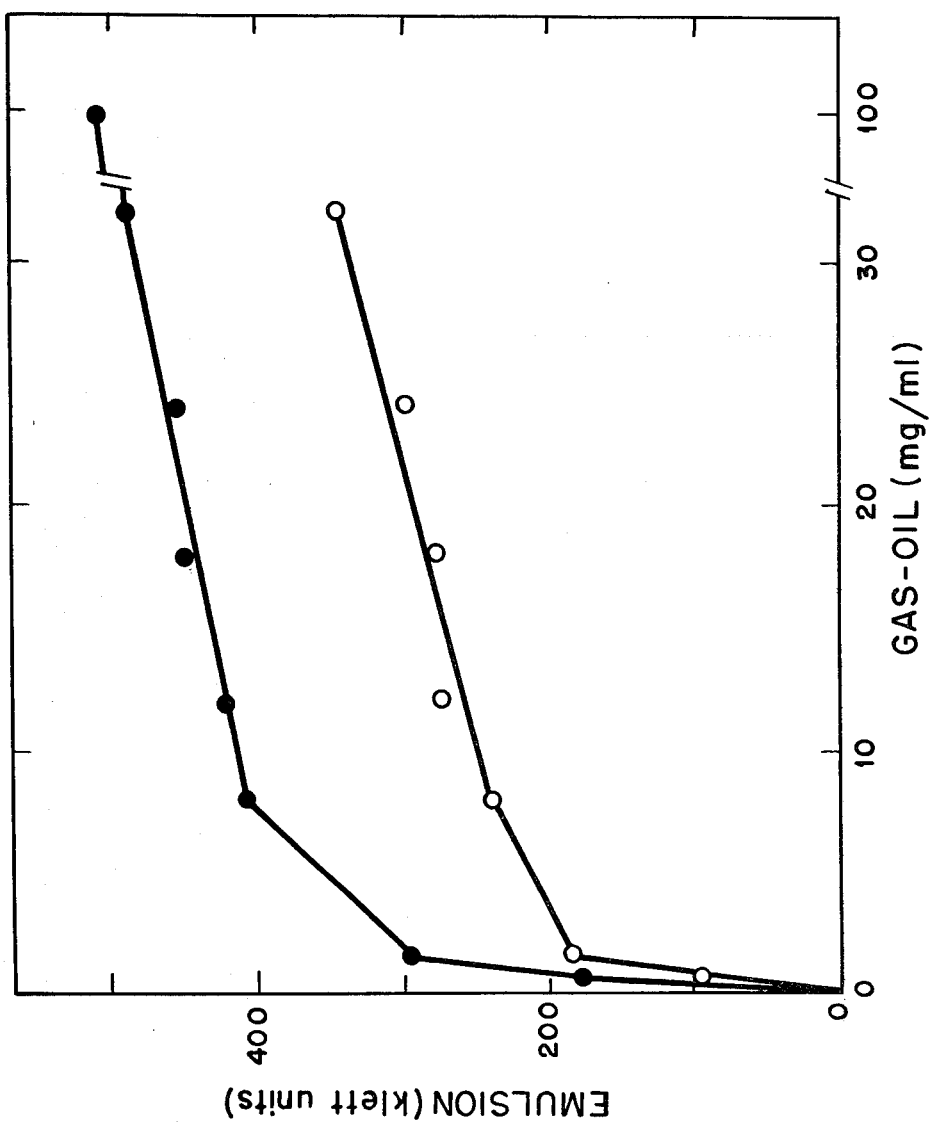
FIG. 7 is a graphical representation of the relationship between the amount of emulsification which is obtained 60 minutes after mixing in the emulsan-induced emulsification of gas-oil as a function of gas-oil concentration for a given concentration of the bioemulsifier.

Emulsion formation as a function of gas-oil concentration is shown in FIG. 7, in which the lower curve represents the data obtained using 33 mcg/ml of bioemulsifier and the upper curve the data obtained using 100 mcg/ml of bioemulsifier, both in filtered sea water, with varying amounts of gas-oil. Each mixture was reciprocally shaken for 60 minutes at 150 strokes per minute, and emulsion formation then measured. Emulsions were formed over the entire gas-oil concentration range studied, 0.5 to 100 mg per ml. Below 1.5 mg gas-oil per ml, turbidities were directly proportional to gas-oil concentration. Between 8 to 30 mg gas-oil per ml, turbidity increased about 5 Klett units per mg gas-oil.

8.2. EFFECT OF pH AND SALT CONCENTRATION ON EMULSION FORMATION

Figure 8:
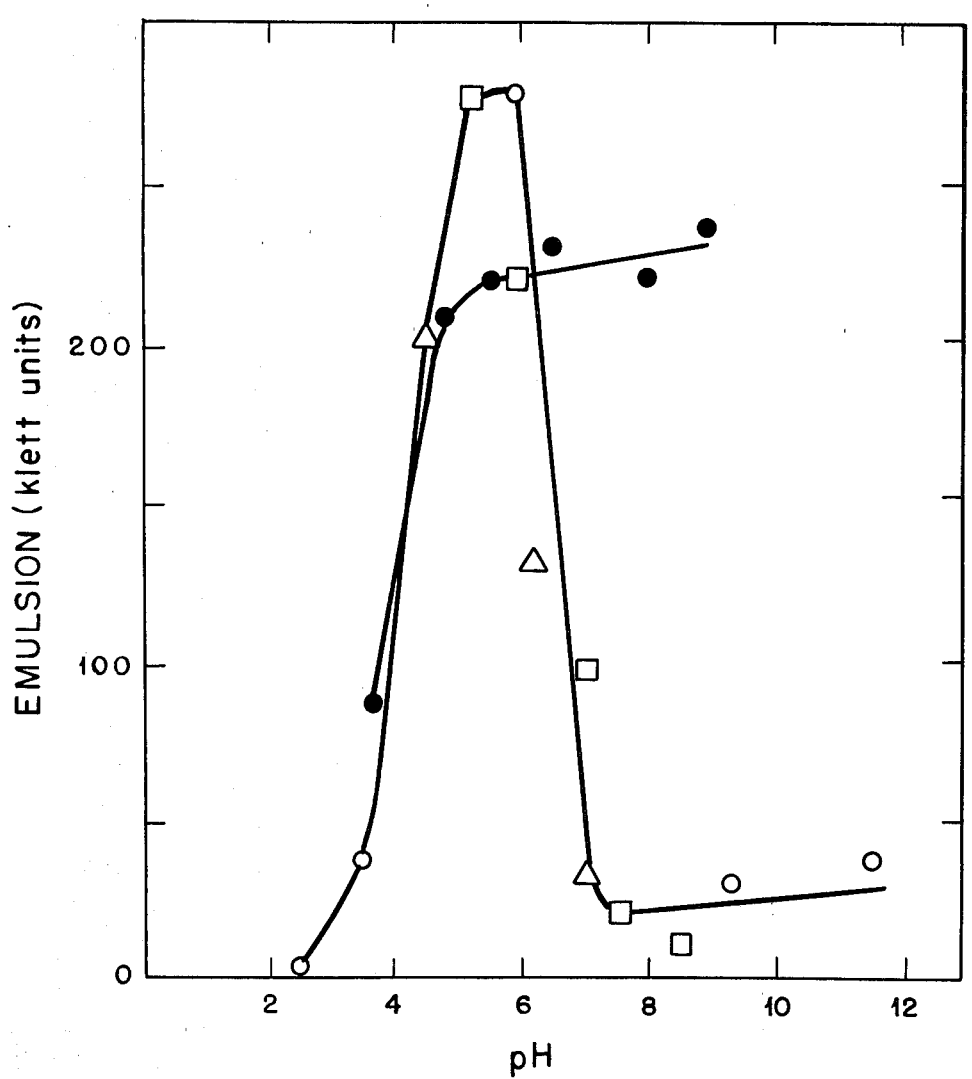
FIG. 8 is a graphical representation of the relationship between the amount of emulsification which is obtained in the emulsan-induced emulsification of gas-oil as a function of pH in fresh water and sea water in the presence and absence of magnesium ions.

Acinetobacter bioemulsifier-induced emulsification of gas-oil as a function of pH is shown in FIG. 8. The data shown in FIG. 8 were based on reciprocally shaking (150 strokes per minute at 25° C. for 60 minutes) flasks which contained 33 mcg/ml of bioemulsifier and 6 mg/ml of Agha-Jari gas-oil in 7.5 ml of either (a) sea water [closed circles]; (b) 10 mM NaCl [open circles]; (c) 100 mM citrate-phosphate buffer [triangles]; or (d) 50 mM Tris-NaOH buffer [squares]. The pH of sa water and 10 mM NaOH were adjusted by addition of HCl or NaOH.

In sea water, near maximum emulsions were obtained from pH 5 to at least pH 9. Above pH 9 precipitation of salts prevented accurate measurements of emulsion. In aqueous solutions containing Tris buffer, citrate-phosphate buffer, or diluted saline, a sharp maximum was obtained between pH 5-6. Above pH 7, activity was completely lost.

Figure 9:
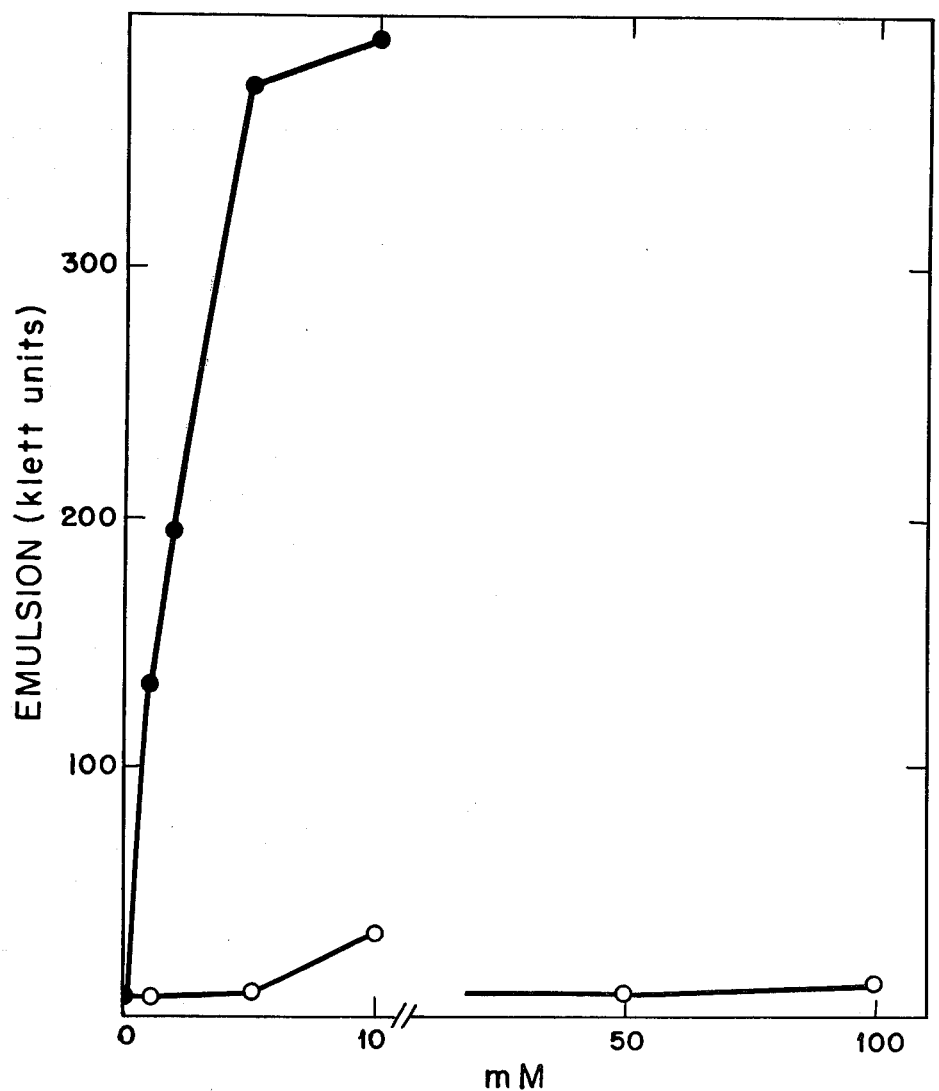
FIG. 9 is a graphical representation of the relationship between the amount of emulsification which is obtained in the emulsan-induced emulsification of gas-oil as a function of salt concentration.

In order better to understand the different results obtained in sea water and fresh water, the effect of salts on bioemulsifier-induced emulsification was measured at pH 7.0 and the data summarized in FIG. 9. The data shown in FIG. 9 was based on the emulsification of gas-oil with the Acinetobacter bioemulsifier in distilled water to which had been added varying concentrations of magnesium chloride (closed circles) or sodium chloride (open circles). Emulsification was measured after reciprocally shaking (150 strokes per minute) the flasks for 60 minutes at 25° C.

Maximum activity was obtained with 5-40 mM magnesium sulfate or magnesium chloride. Half maximum activity was achieved with 1.5 mM magnesium ions ($Mg^{++}$). Calcium chloride (10 mM) and manganese chloride (10 mM) could be substituted for magnesium sulfate. On the other hand, sodium chloride (10–500 mM) had little effect on emulsion formation, either in the presence or absence of magnesium ions. Consequently, the ability of Acinetobacter bioemulsifiers to emulsify hydrocarbons above pH 6 is dependent upon divalent cations and appears to be independent of sodium chloride concentration. Because of this property, these bioemulsifiers are capable of functioning in the presence of high concentrations of sodium chloride found in sea water or connate water.

8.3. STABILITY OF BIOEMULSIFIER-INDUCED EMULSIONS

Figure 10:
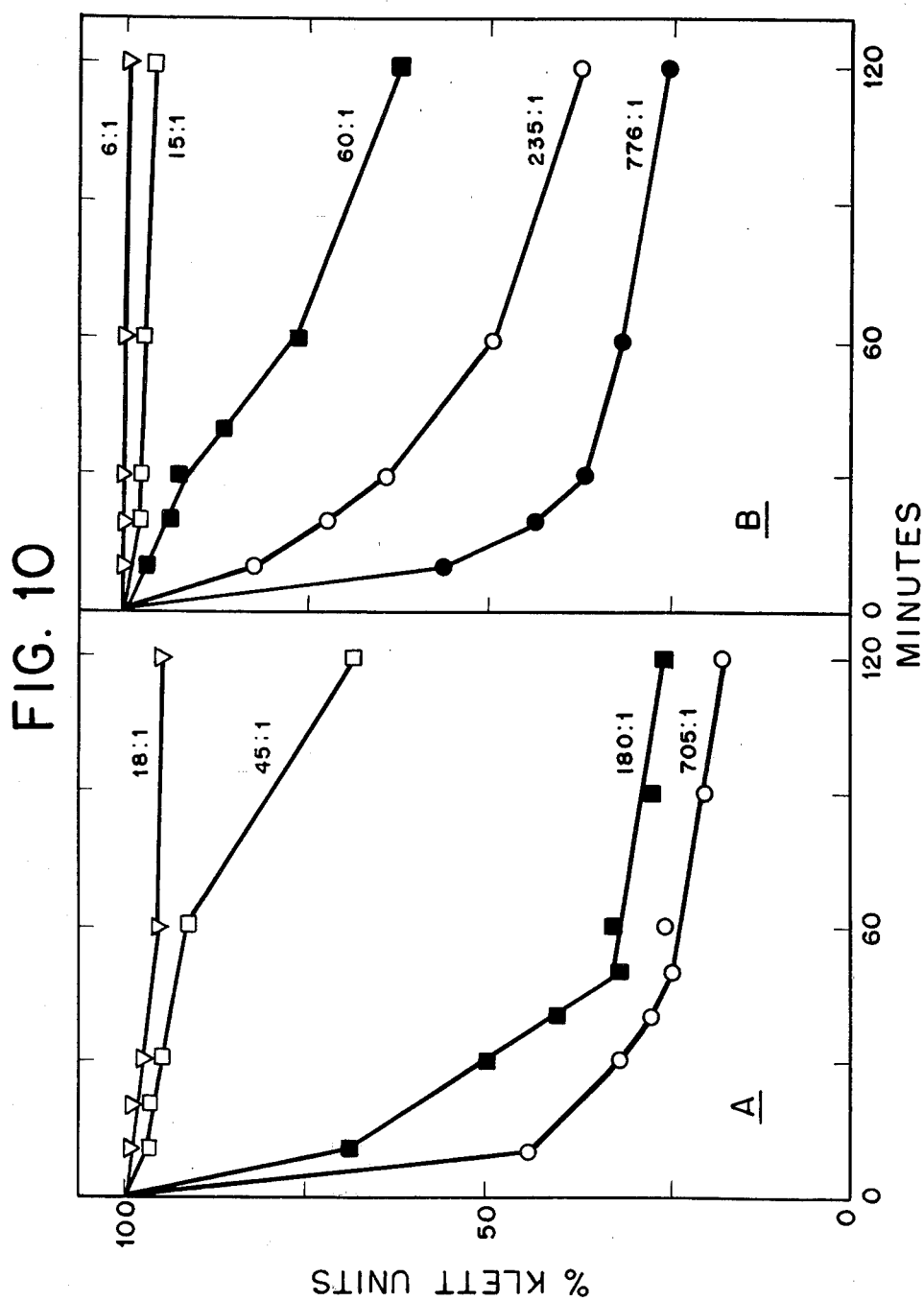
FIG. 10, which is subdivided into

Gas-oil emulsions formed in the presence of Acinetobacter bioemulsifier slowly separate into two phases when allowed to stand undisturbed; namely, a lower clear aqueous phase and a turbid upper phase containing concentrated oil droplets, bound bioemulsifier and water. As observed with a phase microscope, emulsion breakage (demulsification) was a result of "creaming" due to density differences between the two phases and was not accompanied by droplet coalescence or aggregation. The rate of phase separation was followed by turbidity measurements in a Klett tube to determine the stability of the emulsion as a function of the ratio gas-oil/bioemulsifier, the results being summarized in FIG. 10. Emulsions were formed after 120 minutes at 25° C. by reciprocally shaking varying concentrations of gas-oil with either 33 mcg/ml (FIG. 10A) or 100 mcg/ml (FIG. 10B) of Acinetobacter bioemulsifier, and then allowed to stand without shaking from zero time (i.e., immediately after formation of the emulsion) until 120 minutes. In FIGS. 10A and 10B, percent Klett units (Klett units at t=x divided by Klett units at t=0, expressed as percentage) are plotted against standing time. The numbers on each curve refer to the weight ratios of gas-oil/bioemulsifier.

As shown in FIGS. 10A and 10B, emulsion stability depended more upon the ratio of gas-oil/bioemulsifier than on the absolute concentration of bioemulsifier or gas-oil used to form the emulsion. With gas-oil/bioemulsifier ratios of less than 25, over 24 hours standing was required for a 50% decrease in turbidity. With ratios between 25–200 and 200–1000, half-maximum turbidities were reached in 1–24 hours and 10–60 minutes, respectively. In all cases, the upper "cream" immediately dispersed in aqueous media. Emulsion breakage was enhanced by divalent cations.

Figure 11:
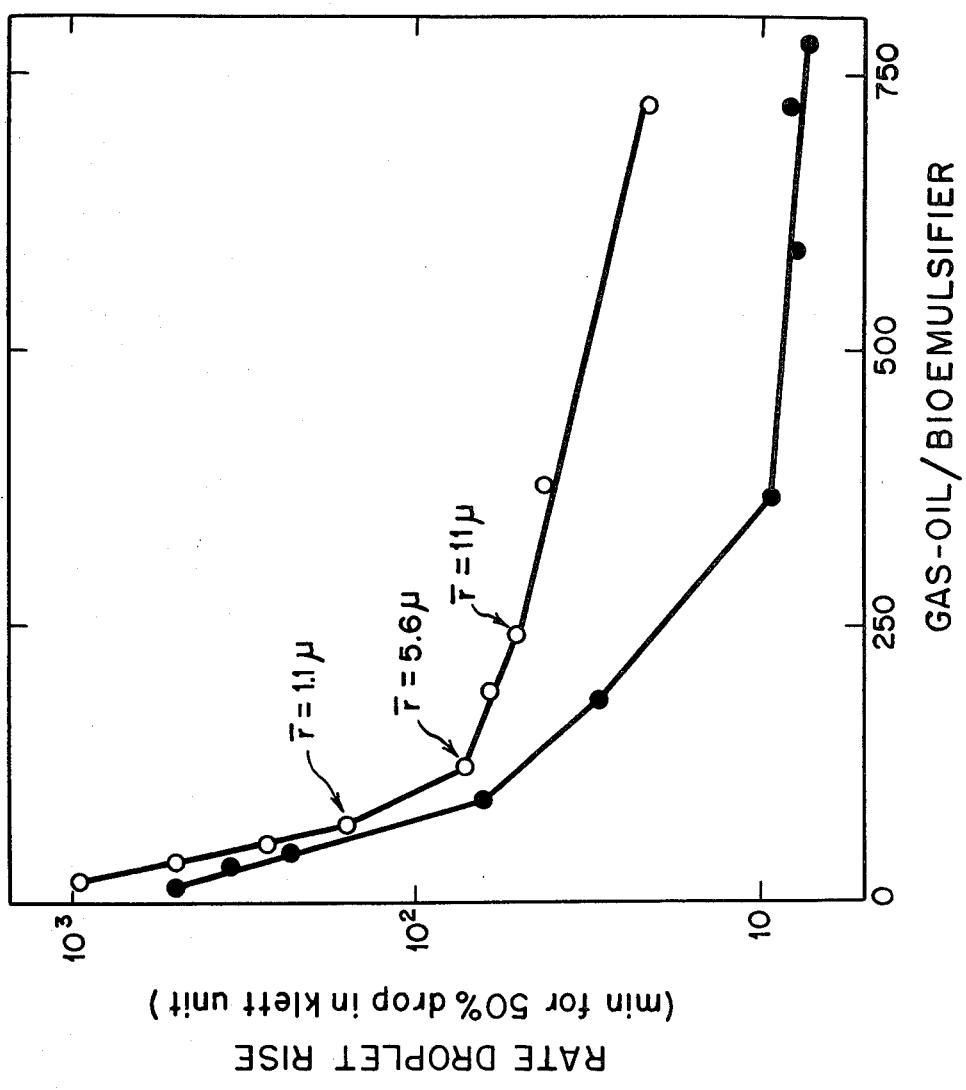
FIG. 11 is a graphical representation of the rate at which emulsified oil droplets rise as a function of the weight ratio of gas-oil to bioemulsifier for given concentrations of the bioemulsifier.

Rate of floatation of oil droplets as a function of gas-oil/bioemulsifier ratio is shown in FIG. 11, in which the upper curve represents data obtained using 100 mcg/ml of bioemulsifier and the lower curve represents data obtained using 33 mcg/ml of bioemulsifier, both with different gas-oil concentrations. The average radii of the droplets, r, were calculated from Stokes equation $V = 21800 \, r^2$, where V is the velocity at which oil droplets rise in cm/sec and r is the radius in cm, using 0.90 g $cm^{-3}$ as the density of gas-oil. The calculated droplet sizes were in good agreement with measurement of droplet size by phase microscopy (using a calibrated eye-piece micrometer). With a ratio of gas-oil/bioemulsifier of 50, the droplets were barely visible by light microscopy.

8.4. LOWERING OF OIL/WATER INTERFACIAL TENSIONS

Figure 12:
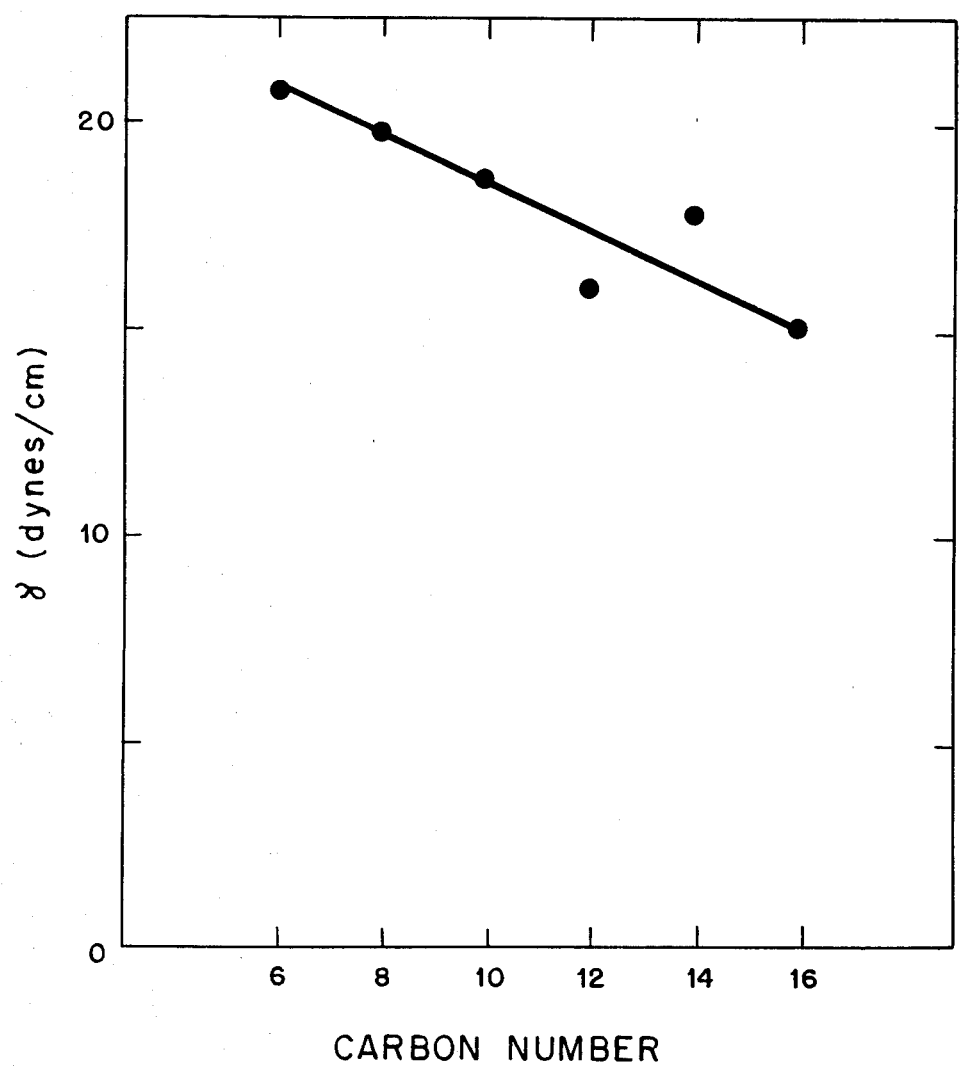
FIG. 12 is a graphical representation showing the relationship between the interfacial tension of n-alkanes in sea water containing a given concentration of emulsan as a function of n-alkane chain length.

The ability of Acinetobacter bioemulsifiers to lower the interfacial tensions between a series of n-alkanes and sea water is shown in FIG. 12, which illustrates the interfacial tensions of n-alkanes from 6 to 16 carbon atoms in sea water containing 0.1% bioemulsifier. Values for interfacial tension were determined at 27° C. using the spinning drop interfacial tensiometer. Using similar techniques, the interfacial tensions between Prudhoe Bay crude oil and sea water were measured using 1 and 10 mg of bioemulsifier per ml, yielding 8.3 and 6.9 dynes per cm, respectively.

9. SPECIFICITY OF THE HYDROCARBON SUBSTRATE

Apart from classification as anionic, cationic or non-ionic, most emulsifiers are described in terms of their HLB numbers, which is a measure of the hydrophile-lipophile balance of the emulsifier. Very often, emulsifiers with similar HLB numbers interact differently with hydrocarbon substrates. Because biologically produced polymers often exhibit specificities not found in chemically synthesized materials, the hydrocarbon substrate specificity for Acinetobacter bioemulsifier-induced emulsion formation was studied using a wide variety of pure hydrocarbons, binary mixtures of hydrocarbons, crude oils, fractions of crude oils and mixtures of crude oil fractions and pure hydrocarbons.

9.1. EMULSIFICATION OF PETROLEUM FRACTIONS

The ability of α-emulsans and β-emulsans to emulsify crude oil and fractions of crude oil is summarized below in Table XIII. All crude oils tested were emulsified by both types of Acinetobacter bioemulsifiers. In addition to the crude oils shown in Table XIII, various crude oils from Alaska, Louisiana and Texas were emulsified by both Acinetobacter bioemulsifiers. Gas-oil was a better substrate for Acinetobacter bioemulsifier-induced emulsification than kerosene or gasoline, both of which formed somewhat unstable emulsions. In general, better emulsions were formed with α-emulsan than with β-emulsan and, in some instances, could only be formed with α-emulsan.

9.2. EMULSIFICATION OF PURE HYDROCARBONS

Figure 13:
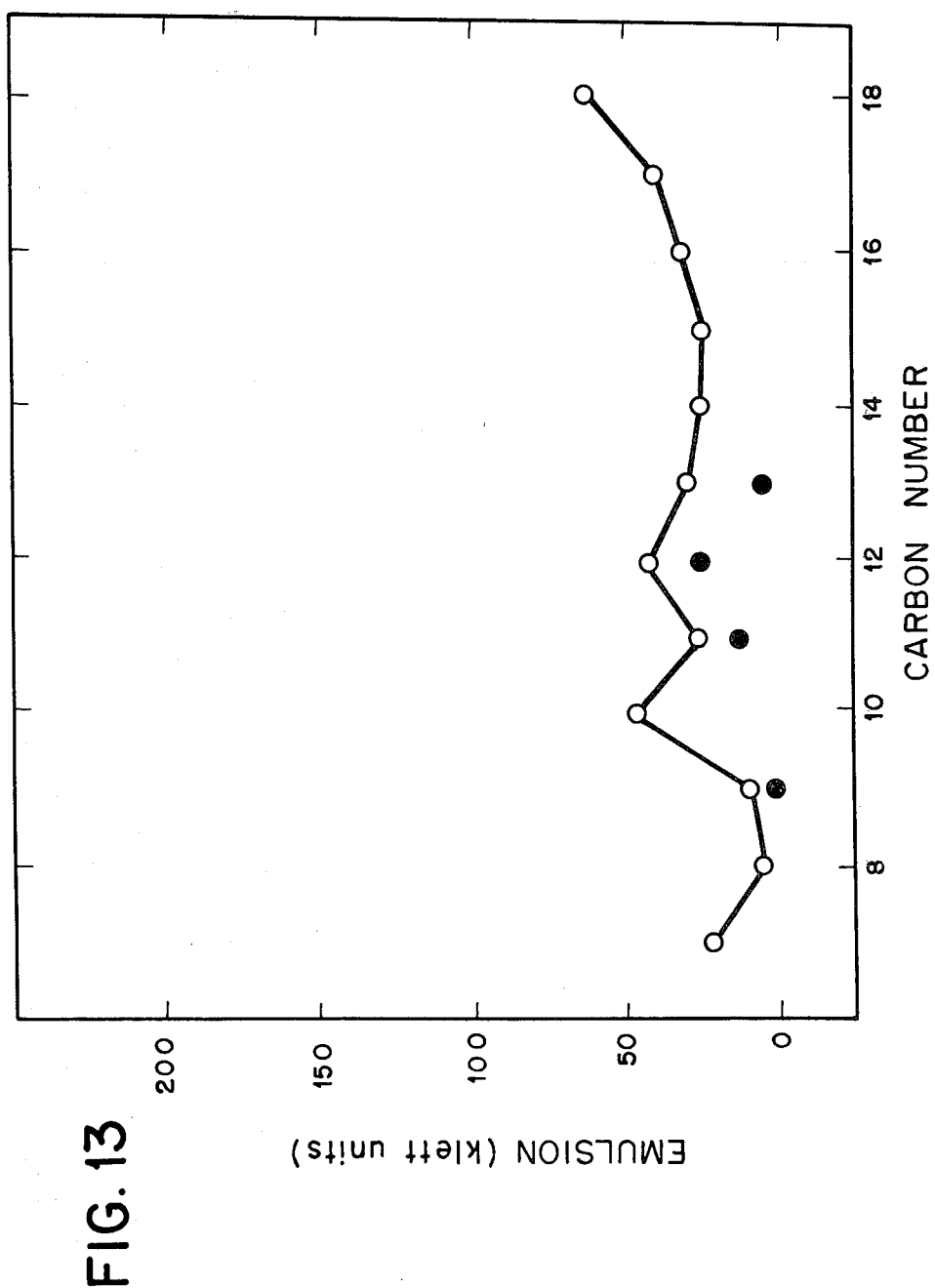
FIG. 13 is a graphical representation showing the relationship of the amount of emulsification which is obtained in the emulsan-induced emulsification of various straight and branch chain alkanes as a function of carbon number of such alkanes.

Straight and branch chain aliphatic hydrocarbons from heptane to octadecane were emulsified only to a slight extent by the Acinetobacter bioemulsifier as illustrated by the data in FIG. 13 which is a graphical representation showing the relationship of the amount of emulsification of various straight and branch chain alkanes as a function of carbon number. The data summarized in FIG. 13 was obtained using 100 mcg/ml of Acinetobacter bioemulsifier and 0.05 ml hydrocarbon, the open circles referring to straight chain alkanes while the closed circles refer to 2,2,5-trimethylhexane, 2-methyldecane, 2,6-dimethyldecane and 2,6-dimethylunidecane. Increasing or decreasing the hydrocarbon concentration by a factor of five did not improve emulsification.

Pentane and hexane were also not emulsified effectively; however, quantitative data for these two paraffins were not obtained because of extensive evaporation during incubation. The solid hydrocarbons, nondecane, n-octacosane and hexatriacontane, were not dispersed by Acinetobacter bioemulsifier.

Figure 14:
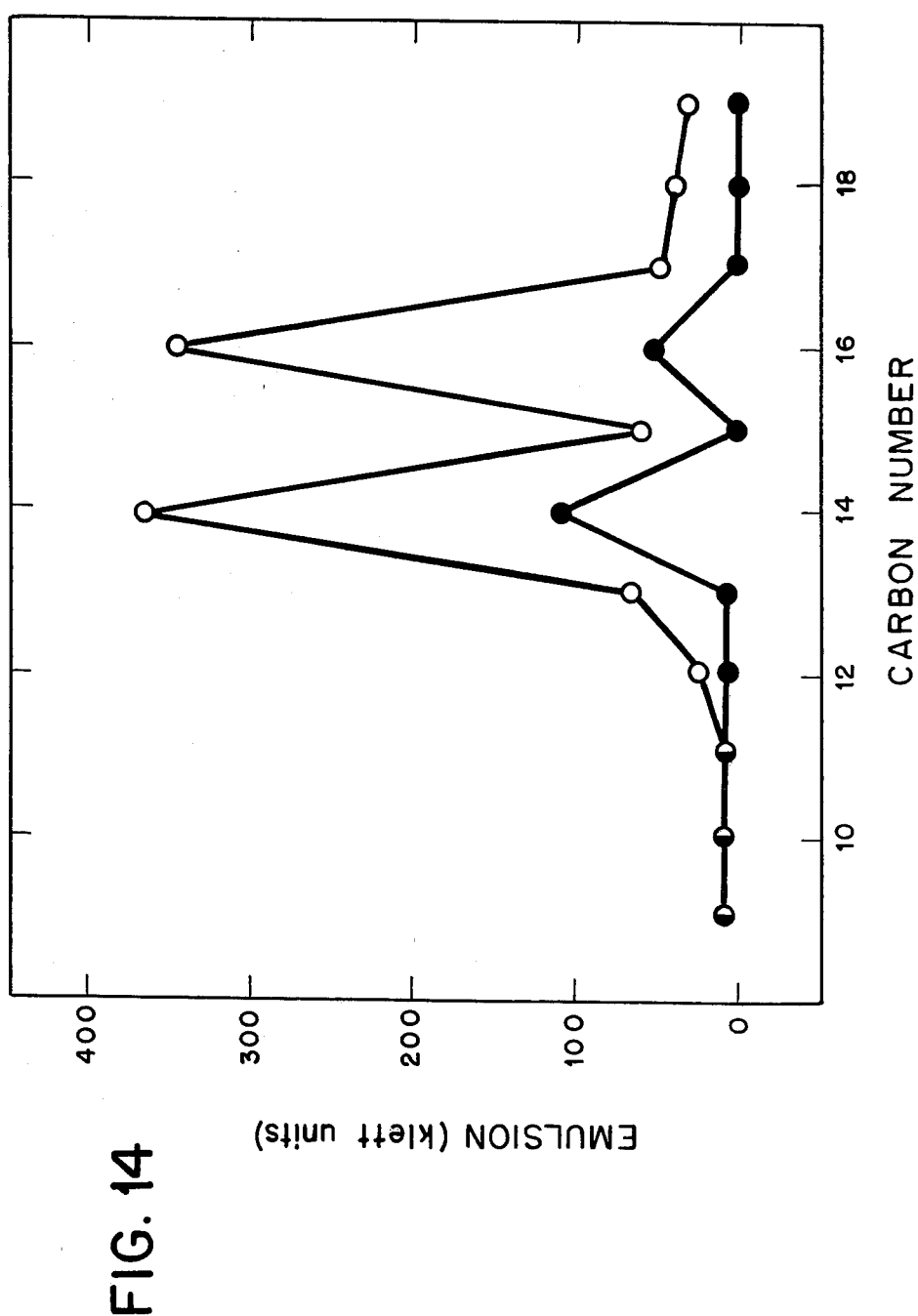
FIG. 14 is a graphical representation showing the relationship of the amount of emulsification which is obtained in the emulsan-induced emulsification of various alkylcyclohexanes as a function of carbon number of such alkylcyclohexanes.

Emulsification of n-alkyl cyclohexane derivatives ranging from propylcyclohexane to tridecylcyclohexane by Acinetobacter bioemulsifier are summarized in FIG. 14, which graphically illustrates emulsification of various alkylcyclohexanes as a function of carbon number. The data shown in FIG. 14 was obtained using 0.2 ml hydrocarbon and either 25 mcg/ml (closed circles) or 100 mcg/ml (open circles) of Acinetobacter bioemulsifier.

As shown in FIG. 14, two peaks of activity were observed, corresponding to octyl cyclohexane and decylcyclohexane. The data for octyl, nonyl and decylcyclohexanes were obtained from redistilled materials which contained no ultraviolet-absorbing impurities. Concentrations of octyl and decylcyclohexane as low as 5 mg per ml were rapidly and completely emulsified by 50 mcg/ml of bioemulsifier. Nonylcyclohexane did not contain any apparent inhibitors of emulsification, since mixtures of octyl and nonylcyclohexane were emulsified to about the same extent as octylcyclohexane alone. Bicyclohexane and decalin were not emulsified significantly.

Figure 15:
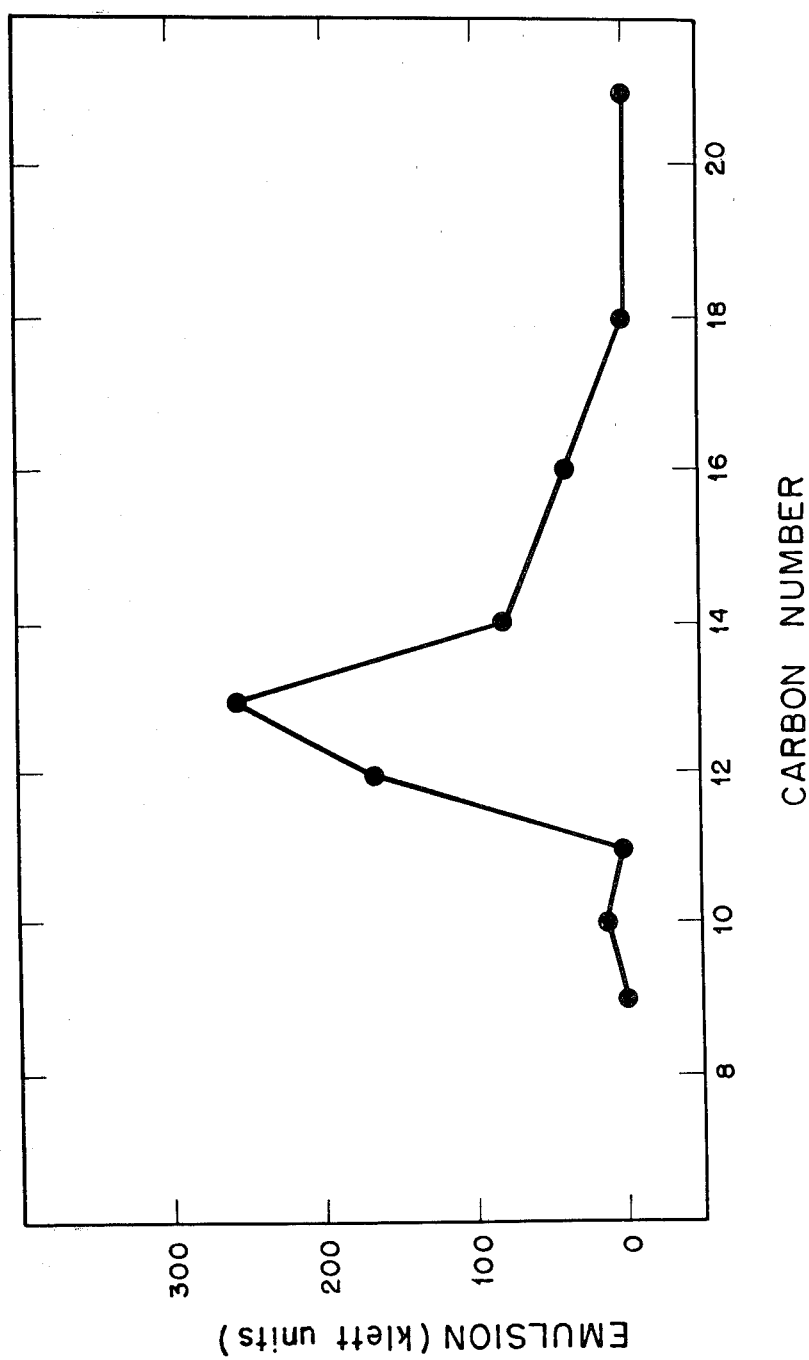
FIG. 15 is a graphical representation showing the relationship of the amount of emulsification which is obtained in the emulsan-induced emulsification of various alkyl-substituted benzenes as a function of carbon number of such alkylbenzenes.

Emulsification of n-alkylbenzene derivatives by Acinetobacter bioemulsifier are summarized in FIG. 15, the data for which was obtained using 0.01 ml hydrocarbon and 50 mcg/ml of bioemulsifier. Maximum activity was obtained with hexyl and heptylbenzenes. The total number of carbon atoms in the side chains may be more crucial than the chain length since p-diisopropylbenzene behaved like hexylbenzene. The low molecular weight benzene derivatives, toluene, p-xylene, m-xylene, ethyl-benzene and 1,2,3,4-tetramethylbenzene, were not emulsified significantly. Aromatic compounds containing more than one ring, naphthalene, biphenyl, phenanthrene, anthracene, 3-phenyltoluene, 1-methylnaphthalene and 2-methylnaphthalene were also not emulsified significantly by the Acinetobacter bioemulsifier.

9.3. EMULSIFICATION OF MIXTURES OF PURE HYDROCARBONS

Table VIII summarizes a number of experiments in which the Acinetobacter bioemulsifier-induced emulsification of aliphatic, aromatic and cyclic hydrocarbons were measured in the presence of hexadecane or 1-methylnaphthalene. Although neither the aliphatic compounds nor 1-methylnaphthalene were emulsified by themselves, all mixtures containing the aromatic compound and one of the aliphatic hydrocarbons were excellent substrates for emulsification by the bioemulsifier. The ability of aromatic compounds to stimulate emulsification of aliphatics was not limited to 1-methylnaphthalene, but occurred with toluene, p-xylene, 3-phenyltoluene and 2-methylnaphthalene. Addition of hexadecane to the aliphatic compounds did not stimulate emulsification, that is, only an additive effect was observed. The minor exception to this finding was nonadecane which became liquid when mixed with hexadecane.

As mentioned above, the only aromatic compounds that served as substrates for emulsification by Acinetobacter bioemulsifier were alkylbenzene derivatives containing six or seven carbon atoms on the side chain(s). Aromatic compounds containing less than six carbon atoms on the side chain were converted into good substrates for emulsification by addition of hexadecane. Hexylbenzene and diisopropylbenzene were converted into even better substrates for emulsification by addition of hexadecane. On the other hand, heptyl, decyl and pentadecylbenzene were emulsified more poorly in the presence of hexadecane than by themselves. Only alkylbenzene derivatives containing side chains of five or more carbon atoms were activated by 1-methylnaphthalene. 1,2,3,4-tetramethylbenzene was poorly emulsified by the bioemulsifier even in the presence of hexadecane or 1-methylnaphthalene. With few exceptions, cycloparaffin derivatives were converted into better substrates for Acinetobacter bioemulsifier-mediated emulsification by addition of either hexadecane or 1-methylnaphthalene. In general, cyclohexane derivatives with short side chains (e.g., ethylcyclohexane) were activated more efficiently with aliphatic than aromatic compounds, while derivatives with long side chains (e.g., duodecylcyclohexane) formed better emulsions in the presence of 1-methylnaphthalene than hexadecane. Dicyclohexane behaved like an aromatic compound in that it was emulsified by the bioemulsifier in the presence of hexadecane but not 1-methylnaphthalene. The fused dicyclic compound decalin could not be emulsified by the bioemulsifier even by addition of hexadecane or 1-methylnaphthalene.

Figure 16:
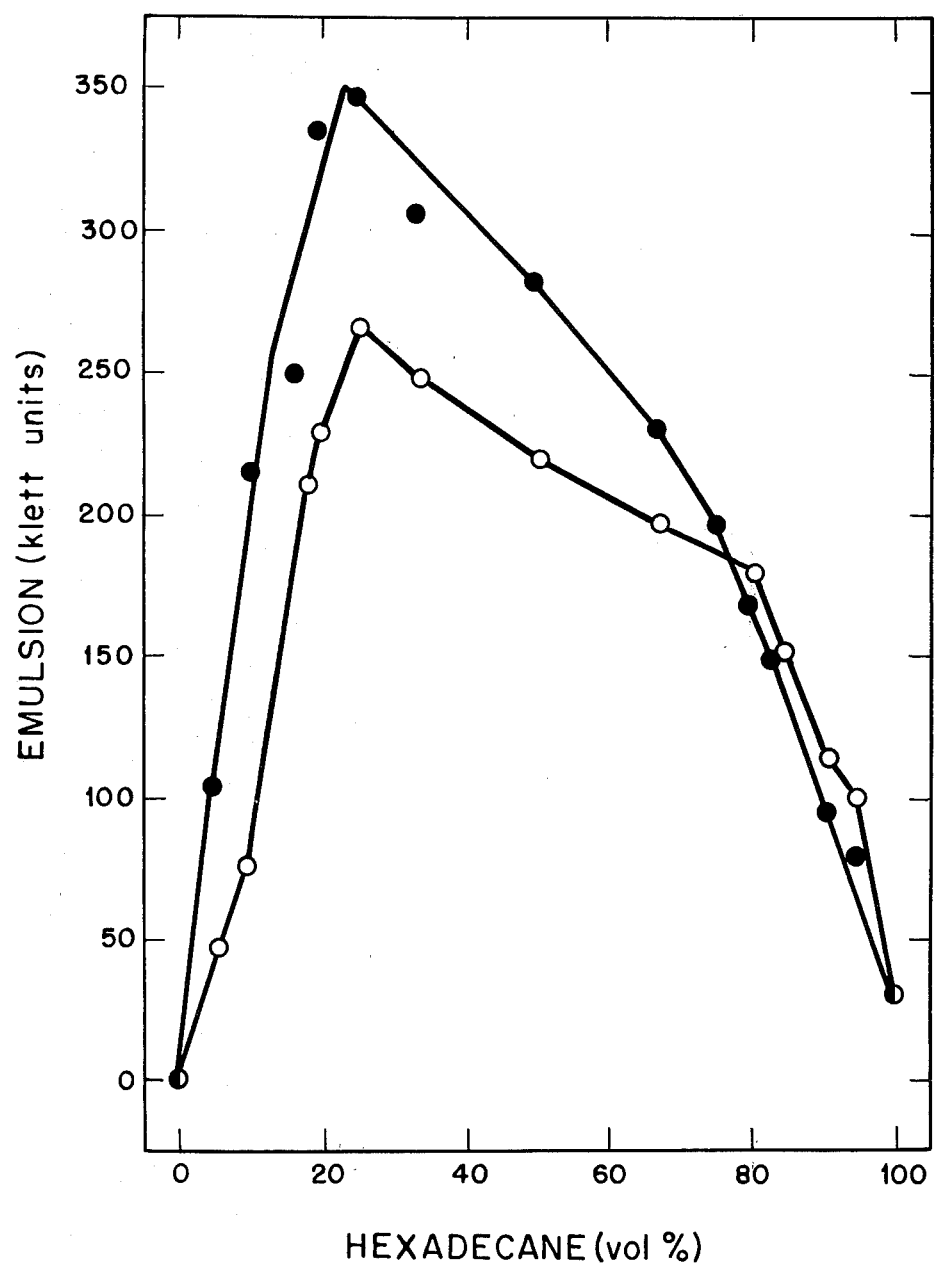
FIG. 16 is a graphical representation showing the relationship of the amount of emulsification which is obtained in the emulsan-induced emulsification of mixtures of hexadecane and a particular methylnaphthalene as a function of the volume percent of hexadecane in such mixtures.

Acinetobacter bioemulsifier-induced emulsion formation as a function of the relative concentrations of aliphatic (hexadecane) and aromatic (methylnaphthalene) compounds is shown in FIG. 16, the data for which was obtained using 50 mcg/ml of bioemulsifier and 0.05 ml of various mixtures of hexadecane and 1-methylnaphthalene (closed circles) or hexadecane and 2-methylnaphthalene (open circles). Using either 1-methylnaphthalene or 2-methylnaphthalene, maximum emulsion was obtained with 25 vol. % hexadecane. Over fifty percent maximum emulsion was obtained with ratios of hexadecane/methylnaphthalene from 4:1 to 1:6. An identical experiment using decane in place of hexadecane yielded similar curves except that the peak of emulsion activity was obtained with 33 vol. % decane.

TABLE VIII

Emulsification of Mixtures of Aliphatic, Aromatic and Cyclic Hydrocarbons by Acinetobacter Bioemulsifier

| Hydrocarbon[a] | Emulsion (Klett units) | | |
|---|---|---|---|
| | no addition | plus hexadecane | plus 1-methylnaphthalene |
| Aliphatics | | | |
| decane | 15 | 41 | 185 |
| tetradecane | 13 | 50 | 216 |
| hexadecane | 20 | 31 | 284 |
| nonadecane | 0 (solid) | 79 | 285 |
| 2,2,5-trimethylhexane | 0 | 34 | 89 |
| 2,6-dimethylunidecane | 0 | 2 | 105 |
| Aromatics | | | |
| biphenyl | 0 (solid) | 123[b] | 19[b] |
| naphthalene | 0 (solid) | 96[b] | 26[b] |
| phenanthrene | 0 (solid) | 61[b] | 36[b] |
| toluene | 22 | 97 | 4 |
| 3-phenyltoluene | 0 | 157 | 0 |
| 1-methylnaphthalene | 0 | 284 | 0 |
| 2-methylnaphthalene | 0 | 244 | 0 |
| p-xylene | 22 | 75 | 15 |
| ethylbenzene | 9 | 117 | 21 |
| propylbenzene | 9 | 90 | 23 |
| pentylbenzene | 4 | 197 | 85 |
| hexylbenzene | 98 | 188 | 165 |
| p-diisopropylbenzene | 96 | 299 | 192 |
| heptylbenzene | 105 | 82 | 186 |
| decylbenzene | 38 | 31 | 49 |
| pentadecylbenzene | 21 | 0 | 5 |
| 1,2,3,4-tetramethylbenzene | 28 | 35 | 9 |
| Cycloparaffins | | | |
| ethylcyclohexane | 8 | 81 | 43 |
| propylcyclohexane | 3 | 81 | 64 |
| butylcyclohexane | 0 | 111 | 57 |
| hexylcyclohexane | 5 | 9 | 116 |
| heptylcyclohexane | 1 | 32 | 131 |
| octylcyclohexane | 109 | 151 | 175 |
| nonylcyclohexane | 0 | 0 | 249 |
| decylcyclohexane | 79 | 192 | 171 |
| duodedecylcyclohexane | 5 | 0 | 72 |
| decalin | 0 | 15 | 17 |
| dicyclohexane | 14 | 201 | 39 |

[a]Experiments were performed using 50 mcg/ml of β-emulsan and 0.025 ml of each hydrocarbon (20 mg for solids).
[b]For solubility reasons, 0.05 ml solutions containing 10% biphenyl, 10% naphthalene and 5% phenanthrene in hexadecane or 1-methylnaphthalene were used.

9.4. EFFECT OF ADDITION OF ALIPHATIC AND AROMATIC COMPOUNDS ON EMULSIFICATION OF PETROLEUM FRACTIONS

The results shown in Table VIII and summarized in FIG. 16 lead to the conclusion that the ability of the Acinetobacter bioemulsifiers to emulsify hydrocarbons depends on the relative concentrations of aliphatic, cyclic and aromatic components in the hydrocarbon substrate. To verify this conclusion, experiments were designed to determine whether or not addition of hexadecane or methylnaphthalene could enhance Acinetobacter bioemulsifier-induced emulsification of petroleum fractions which had been fractionated to separate a fraction rich in aliphatics (Fraction 1) from two fractions (Fractions 2 and 3) rich in aromatics. These experiments, which are more fully described below in Section 13.14, show that the ability of α-emulsan to emulsify both kerosene and gasoline was enhanced greatly by 2-methylnaphthalene but not by hexadecane. Addition of even one part of the aromatic compound to ten parts of gasoline or kerosene resulted in a much improved substrate for emulsification. The requirement for both aliphatic and aromatic constituents was further supported by studying emulsification of column fractionated crude oil. Although crude oil itself is emulsified by the Acinetobacter bioemulsifier, none of the fractions were good substrates by themselves. However, mixtures containing one fraction (Fraction 1) rich in aliphatics and the other (Fractions 2 or 3) rich in aromatics were efficiently emulsified.

10. SUMMARY OF DIFFERENCES BETWEEN α-EMULSANS AND β-EMULSANS

The major differences between α-emulsans and β-emulsans, the two classes of bioemulsifiers produced by Acinetobacter Sp. ATCC 31012, may be subdivided into (a) differences in yield; (b) differences in structure; and (c) differences in emulsifying activity. Table IX summarizes several of such differences between α-emulsans, β-emulsans and their respective deproteinized derivatives. The particular α-emulsans referred to in Table IX were prepared by growing Acinetobacter Sp. ATCC 31012 on ethanol media, while the β-emulsans were prepared from an identical fermentation media using identical growth conditions except that hexadecane was substituted for ethanol. Both bioemulsifiers were purified by ammonium sulfate fractionation, and the deproteinized derivative of each bioemulsifier was prepared by hot phenol extraction and further purified prior to analysis. Total fatty acids content was determined using the hydroxamic acid test, taking the average equivalent weight of the fatty acid esters to be 230.

TABLE IX
Differences Between α-Emulsans and β-Emulsans and Their Respective Deproteinized Derivatives

| Bioemulsifier[a] | Yield (mg/ml) | Specific Activity[b] (units/mg) | % Esters[b] | A/B Ratio[c] |
|---|---|---|---|---|
| 'Emulsans | 1–5 | 200–350 | — | — |
| Apo-α-emulsans | — | 100–200 | 8–14 | 0.2–0.5 |
| β-Emulsans | 0.1–0.75 | 50–200 | — | — |
| Apo-β-emulsans | — | 25–75 | 3–3 | >0.8 |

[a]αEmulsan was prepared from an ethanol medium and proto-emulsan from a hexadecane medium. Both bioemulsifiers were purified by ammonium sulfate fractionation. The deproteinized derivatives of each bioemulsifier were prepared by hot phenol extraction and further purified prior to analysis.
[b]Total fatty ester content was determined using the hydroxamic acid test, taking the average equivalent weight of the fatty acid esters to be 230.
[c]A and B refer to 2-hydroxydodecanoic acid and 3-hydroxydodecanoic acid, respectively.

10.1. DIFFERENCES IN YIELD

As shown by Table IX and as further illustrated in the data summarized in FIGS. 2 and 3, the yield of α-emulsan is invariably greater than the yield of β-emulsan even when identical cultures of Acinetobacter Sp. ATCC 31012 are used as innocula on ethanol and hexadecane media, respectively. Moreover, when the organism is grown on other carbon sources which produce α-emulsans, such as palmitic acid and dodecane, the yields of the high-ester α-emulsan are higher than the β-emulsans obtained when the organism is grown on such carbon sources as pentadecane or hexadecane.

10.2. DIFFERENCES IN STRUCTURE

Purified α-emulsans have a higher specific activity than purified β-emulsans, which is probably due to the higher fatty acid ester content of α-emulsans and may also be due to the generally higher amount of 3-hydroxydodecanoic acid in α-emulsans compared to β-emulsans. As shown in Table IX, the apo-α-emulsan component of the α-emulsans contained from 8 to 14% by weight of total esters, while the apo-β-emulsan component of the β-emulsans contained appreciably less (2–3%) fatty acid esters. Moreover, the apo-α-emulsan content of α-emulsans generally possess a lower ratio of 2-hydroxydodecanoic acid to 3-hydroxydodecanoic acid (usually about 1:4 to about 1:2) than in the apo-β-emulsan component of β-emulsans.

Table X summarizes the different ester compositions of an apo-α-emulsan derived from deproteinization of an α-emulsan formed when Acinetobacter Sp. ATCC 31012 was grown on an ethanol medium when compared to the apo-β-emulsan derived from a β-emulsan formed when the organism was grown on hexadecane. Each of the deproteinized Acinetobacter bioemulsifiers was hydrolyzed in KOH/methanol for 4 days at room temperature, the corresponding mixture of methyl esters were formed with diazomethane and the methyl esters of each mixture were then fractionated by chromatography.

TABLE X
Ester Composition of Apo-α-emulsan and Apo-β-emulsan

| Fatty Acid | Apo-α-emulsan (% Wgt) | Apo-β-emulsan (% Wgt) |
|---|---|---|
| Decanoic | 0.84 | 0.39 |
| Dodecanoic | 1.70 | 0.41 |
| Dodecenoic | 0.18 | 0.08 |
| 2-Hydroxydodecanoic | 0.78 | 0.44 |
| 3-Hydroxydodecanoic | 2.92 | 0.54 |
| Hexadecanoic | 0.05 | trace |
| Hexadecenoic | trace | trace |
| Octadecanoic | 0.02 | trace |
| Octadecenoic | trace | trace |
| Unidentified | 0.89 | 0.53 |
| TOTAL ESTERS | 7.4 | 2.4 |

The data shown in Table X confirm the general rule that in the apo-α-emulsan content of α-emulsans, the aggregate amount of 2hydroxydodecanoic acid and 3-hydroxydedecanoic acid is usually about 50% of the total fatty acid esters and may be as high as 70% of the fatty acid esters in the lipopolysaccharide.

10.3. DIFFERENCES IN EMULSIFYING ACTIVITY

The data contained in Table XIII below show that although α-emulsan and β-emulsan are both excellent emulsifiers for crude oils and are both only fair emulsifiers for kerosenes, α-emulsan is much more effective than β-emulsan in the emulsification of gas-oils. Moreover, Bunker C fuel oil is emulsified by α-emulsan but not by β-emulsan. In general, experience has shown that α-emulsans give better emulsions than β-emulsans with hydrocarbon substrates which contain both aliphatic and aromatic (or cyclic) components.

11. SORPTIVE PROPERTIES OF EMULSANS AND THEIR DERIVATIVES ON SOLID SUBSTRATES

The adsorption or non-adsorption of emulsans and apoemulsans on various types of solid substrates, such as sand, limestone or clay minerals, were measured to determine whether these anionic lipopolysaccharides could function as bioemulsifiers in the presence of such solid substrates.

11.1. NON-ADSORPTION ON SAND AND LIMESTONE

Neither emulsans nor apoemulsans are adsorbed to any significant extent on sand or on limestone over the pH range in which these bioemulsifiers will be used to form oil-in-water emulsions. When oil is present on the sand or limestone, such as in sand or sandstone reservoir formations or in limestone reservoir formations, the oil may be recovered by enhanced oil recovery using chemical flooding with dilute concentrations of emulsan, since bench scale experiments have shown that when oil-saturated sand or oil-saturated limestone are treated with dilute solutions (i.e., from 0.1 to 0.5 mg/ml) of α-emulsan containing magnesium ions (10 mM), over 90% of the oil can be removed from the oil-saturated sand and over 98% of the oil can be removed from the oil-saturated limestone. Comparable results may be obtained using sea water solutions of emulsans, since the presence of sodium chloride in the concentrations found in sea water or in connate water do not affect the ability of emulsans to emulsify crude oils, including crude oils which are quite viscous or tarry, which are found in sand (or sandstone) formations or in limestone formations or which remain in such formations after secondary recovery techniques (such as steam stripping) are employed.

11.2. ADSORPTION ON ALUMINOSILICATE CLAYS

Emulsans and their deproteinized derivatives, the apoemulsans, both of which are strongly anionic, are adsorbed on aluminosilicate ion-exchangers, such as kaolin, bentonite and other clay minerals which have ion-exchange capacity.

Figure 17:
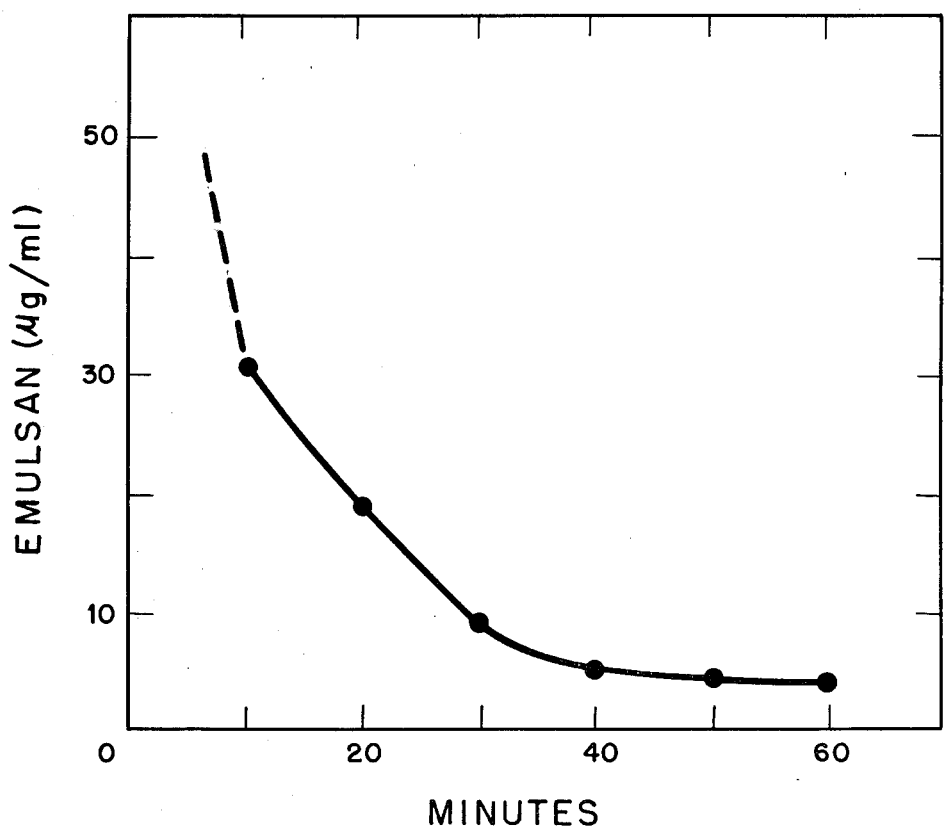
FIG. 17 is a graphical representation of the kinetics of adsorption of emulsan on bentonite, showing the relationship between the amount of emulsan remaining in solution as a function of time after a given concentration of emulsan is shaken with a given amount of bentonite.

The kinetics of adsorption of α-emulsan on bentonite are shown in FIG. 17, which summarizes the rate of adsorption of α-emulsan onto 0.5 g bentonite in a 20 ml solution of 20 mM Tris-Mg buffer [20 mM tris(hydroxymethyl)aminomethane hydrochloride and 10 mM magnesium sulfate] containing 100 mcg/ml of α-emulsan. The mixture was shaken at 20° C. at 110 strokes per minute in 100 ml flasks, with samples being removed every 10 minutes for assay of α-emulsan not bound to the bentonite. Under these conditions, over 95% of the α-emulsan was adsorbed and equilibrium reached in 40 minutes. The amount of α-emulsan adsorbed by the aluminosilicate clay was a function of the amount of clay, about 70% of the α-emulsan being adsorbed at a bentonite/emulsan ratio of 100:1 and over 95% of the α-emulsan at ratios over 400:1.

11.3. FLOCCULATION OF CLAYS

Adsorption of emulsans (as well as the apoemulsans, ψ-emulsans and proemulsans) onto suspended particles of aluminosilicate clays, such as kaolin and bentonite, results in rapid flocculation of such particles. By way of illustration, mixing 1 g of bentonite with 20 ml water containing only 100 mcg/ml of α-emulsan causes the bentonite to sediment from five to ten times faster than in the absense of emulsan. Moreover, the supernatant fluid obtained using emulsan-mediated flocculation was clear, while the sedimentation of bentonite without the emulsan yielded an upper layer which remained opalescent even after prolonged standing. Similar results may be obtained with other clay materials with ion-exchange capacity.

The flocculating properties of emulsans (which apply equally to the corresponding apoemulsans, as well as to their deacylated derivatives, ψ-emulsans and proemulsans, all of which are also anionic) prevent the packing of aluminosilicate clays into a dense precipitate in such manner that the volume occupied by the flocculated clays is several times greater (three times in the case of bentonite) than in the absence of the lipopolysaccharide. The flocculated aluminosilicate clays now have certain fluid and flow properties which suggest an enormous number of uses for emulsans and apoemulsans and their derivatives in flocculation, including (a) the use of emulsans and apoemulsans as a clay particle flocculent in drilling muds; (b) the prevention of clogging in sewage treatment systems; (c) enhancing the porosity of clay solids to structure poor soils for uses in agriculture; (d) the inclusion of emulsans in coatings and aerosol sprays containing such clays; and (e) the use of emulsans and apoemulsans as a general flocculating agent for recovery and settling processes.

11.4. RELATIONSHIP OF FLOCCULATION TO BREAKING OIL/WATER EMULSIONS

Adsorption of emulsans onto aluminosilicate clays creates an oleophilic clay which, in turn, is capable of breaking a stable oil/water emulsion formed with the bioemulsifier. By way of illustration, emulsification of 1 ml Agha Jari crude oil in 10 ml sea water containing about 0.1 mg/ml of α-emulsan forms an oil-in-water emulsion which is stable after standing two days. The addition of 1 g of preswelled bentonite to this stable emulsion, followed by intense shaking for about 20 seconds, resulted in breakage of the emulsion in 15 minutes. After 20 hours, there were two separated layers, namely an upper clear liquid and a lower gel-like sediment which occupied about one-half of the prior volume of the emulsion.

These sorptive properties of emulsans and apoemulsans with respect to aluminosilicate clay ion-exchangers may also be utilized to remove oil and hydrocarbonaceous sludge from oily ballast water or other oily water, either by filtering such oily waters through an aluminosilicate clay (such as kaolin or bentonite) on which an emulsan or apoemulsan had been adsorbed or, alternatively, by adding the emulsan or apoemulsan to the oily water and then filtering the mixture through an aluminosilicate clay. In both cases, the filtrate will be clear and the oily residue will remain in the clay filter.

12. ENVIRONMENTAL AND ENERGY-RELATED USES

The emulsifying agents of the invention, which comprise an aqueous solution in sea water or fresh water containing (1) from about 10 mcg/ml to about 20 mg/ml of α-emulsans, and (2) from about 1 to about 100 mM of at least one divalent cation, such as magnesium, calcium or manganese, possess the combination of characteristics that permit these emulsifying agents to be widely employed for several important environmental and energy-related uses, namely cleaning oil-contaminated vessels, oil spill management, and enhanced oil recovery by chemical flooding.

By way of illustration, hydrocarbonaceous residues (including residual petroleum) may be cleaned from tankers, barges, storage tanks, tank cars and trucks, pipelines, and other containers used to transport or to store crude oil or petroleum fractions, by washing the oil-contaminated surfaces of such vessels with the emulsifying agent, using an amount of α-emulsan in the solution which can be predetermined based on the composition of the particular hydrocarbon to be removed. As a general rule, complete cleaning can be accomplished with hydrocarbon/emulsan weight ratios of about 1000:1 to 10000:1, the higher the ratio the less stable the emulsion. Moreover, the resultant oil-in-water emulsions can be broken by physical or chemical techniques, and the oil recovered for fuel values or for refining.

Oil spill management is another environmentally important use for the emulsifying agents of the invention. In most processes for cleaning oil spills, an aqueous solution of a detergent or surfactant is brought into contact with the oil slick, which is floating on the sea or which has been washed ashore or deposited on land to emulsify the oil so that it may be dispersed and either removed or biodegraded. Most of the detergents or surfactants commonly used are somewhat toxic to marine life and are not biodegradable. By using the emulsifying agents of the invention, namely the aqueous solution in sea water or fresh water containing from about 10 mcg/ml to about 20 mg/ml of α-emulsans and an effective concentration of at least one divalent cation, not only is it possible to emulsify the oil with less emulsifier which is itself biodegradable but also to avoid toxological problems since emulsans are non-toxic in the concentrations in which they are used as bioemulsifiers. This technique is especially useful in cleaning beaches contaminated with oil.

Enhanced oil recovery by chemical flooding represents a particularly important energy-related use for α-emulsans. All processes in the enhanced recovery of oil by chemical flooding involve the injection of a chemically-augmented "slug" comprising water and one or more added chemicals into a petroleum reservoir followed by displacement of the "slug" through the reservoir to recover crude oil from the injected reservoir. Because of the unique combination of properties of emulsans and particularly for α-emulsans—namely (a) that emulsans on a weight-for-weight basis are probably the most efficient oil-in-water emulsifiers discovered; (b) that emulsans exhibit a high degree of specificity in emulsifying hydrocarbon substrates that contain aliphatic and aromatic or cyclic fractions, which are present in all crude oils including the viscous and tarry crudes remaining in the reservoir after primary and secondary recovery; (c) that emulsans function effectively even in the presence of high concentrations of salts, such as brine; and (d) that emulsans are not adsorbed to any significant extent by sand or sandstone or limestone—using a chemically-augmented slug which contains effective concentrations of α-emulsans and the necessary divalent cation will appreciably increase the recovery of oil from sand or sandstone or limestone formations. Moreover, these anionic lipopolysaccharides may be used as the sole emulsifier or in conjunction with other emulsifying agents (such as the anionic surfactants used for tertiary oil recovery), as well as in conjunction with the mobility control polymers used in such processes.

13. EXAMPLES

The following examples are illustrative of the preparation, purification and some of the uses of the α-emulsans and apo-α-emulsans derived from Acinetobacter Sp. ATCC 31012 when compared to the β-emulsans and apo-β-emulsans which, in turn, are derived from growing the same organism on a different substrate. Except when otherwise indicated, the α-emulsans described in such examples were obtained by growing the organism on an ethanol medium. Where used, the β-emulsans were obtained by growing the organism on a hexadecane medium.

13.1. PREPARATION OF α-EMULSAN FROM ETHANOL IN FRESH WATER MEDIA

To a 60-liter fermenter fitted with four baffles and a variable-speed agitator were added 733.6 g of dibasic potassium phosphate [$K_2HPO_4.3H_2O$], 240 g of monobasic potassium phosphate, 8 g of magnesium sulfate [$MgSO_4.7H_2O$], 160 g of ammonium sulfate and a sufficient amount of deionized water to make 40 liters. The medium was sterilized for 40 minutes at 121° C., after which 800 ml of absolute ethanol (2% by volume) was added. The final pH of the medium was 6.9.

Growth was initiated with 2 liters (5%) of a late exponential culture of Acinetobacter Sp. ATCC 31012 grown under similar fermentation conditions. The fermentation was conducted at 30° C., with aeration maintained at 15 liters of air per minute and agitation at 250 rpm. The pH of the fermentation broth was maintained between pH 6.2 and 6.7 by the dropwise addition of concentrated ammonium hydroxide, which required approximately 185 ml of concentrated ammonium hydroxide during the first 30 hours.

Throughout the fermentation, foam was controlled by automatic pulse additions of a silicone defoamer (Dow Corning 525, sterlizable, diluted 1:8), in connection with which an aggregate of 50 ml was added during the first 30 hours. Commencing at the 11th hour of fermentation, ethanol was continuously added to the fermentation broth at the rate of 40 ml per hour. Ammonium sulfate was periodically added to the fermentation broth at the rate of 2 g per hour for the first 30 hours.

Maximum growth was obtained between 24 to 30 hours after inoculation. The yield of α-emulsan was 4 g per liter, with a cell mass of approximately 8 g (dry weight basis) per liter. Analysis of the crude α-emulsan, which was performed on the crude extracellular fluid following extensive dialysis against water, showed that it contained a total ester content of 10% using the hydroxamic acid test and assuming that the average molecular weight of the fatty acid esters was 230. Using substantially identical conditions, as much as 5.3 g per liter of α-emulsan were obtained with a cell mass of about 9 g (dry weight basis) per liter.

13.2. PREPARATION OF α-EMULSAN FROM ETHANOL IN SEA WATER

Acinetobacter Sp. ATCC 31012 was grown in a 250 ml flask containing 40 ml filtered sea water, 0.73 g dibasic potassium phosphate [$K_2HPO_4.3H_2O$], 0.24 g monobasic potassium phosphate, 0.8 g urea, and 0.8 ml absolute ethanol (2% by volume). The medium was inoculated with 2 ml of a late exponential culture of Acinetobacter Sp. ATCC 31012 grown under similar conditions. Incubation was for 96 hours at 30° C., with gyratory shaking at 250 rpm. After removal of the cells by centrifugation at 10,000×g for 15 minutes and dialysis against water, analysis showed that the yield of crude α-emulsan was 120 units per ml with a specific activity of 270 units per mg. The crude α-emulsan contained 13% total ester content when measured by the hydroxamic acid test, assuming the average molecular weight of the fatty acid esters to be 230.

13.3. PREPARATION OF α-EMULSAN FROM SODIUM PALMITATE

Acinetobacter Sp. ATCC 31012 was grown in an aqueous medium containing 18.34 mg/ml of dibasic potassium phosphate [$K_2HPO_4.3H_2O$], 6 mg/ml of mono sic potassium phosphate, 0.2 mg/ml of magnesium sulfate [MgSO$_4$.7H$_2$O], 4 mg/ml of ammonium sulfate and 1.2 mg/ml of sodium palmitate. Growth was initiated by inoculating 0.1 ml of a washed cell suspension into 40 ml of the medium in a 250 ml flask. Incubation was for 72 hours at 30° C., with gyrotary shaking at 250 rpm. After removal of the cells and extensive dialysis of the crude extracellular fluid against water, analysis showed that the yield of the α-emulsan was 111 units per ml with a specific activity of 116 units per mg determined by the standard assay technique. The crude α-emulsan contained 9% total ester content when measured by the hydroxamic acid test, assuming the average molecular weight of the fatty acid esters to be 230.

13.4. PREPARATION OF α-EMULSAN FROM DODECANE

Acinetobacter Sp. ATCC 31012 was grown in an aqueous medium containing 18.34 mg/ml of dibasic potassium phosphate [K$_2$HPO$_4$.3H$_2$O], 6 mg/ml of monobasic potassium phosphate, 0.2 mg/ml of magnesium sulfate [MgSO$_4$.7H$_2$O], 4 mg/ml of ammonium sulfate and 0.8 mg/ml of dodecane. Growth was initiated by inoculating 0.1 ml of a washed cell suspension into 40 ml of the medium in a 250 ml flask. Incubation was for 72 hours at 30° C., with gyrotary shaking at 250 rpm. After removal of the cells and extensive dialysis of the crude extracellular fluid against water, analysis showed that the yield of the emulsan was 76 units per ml with a specific activity of 81 units per mg determined by the standard assay technique. The crude emulsan contained 9% total ester content when measured by the hydroxamic acid test, assuming the average molecular weight of the fatty acid esters to be 230.

13.5. PREPARATION OF β-EMULSAN FROM HEXADECANE

Using the medium described above in Section 13.4 with 0.2 mg/ml of hexadecane being substituted as the primary assimilable carbon source in place of dodecane, Acinetobacter Sp. ATCC 31012 was grown at 30° C. for 72 hours, with gyrotary shaking at 250 rpm. As before, growth was initiated by inoculating 0.1 ml of a washed cell suspension into 40 ml of the medium in a 250 ml flask.

After removal of the cells and extensive dialysis of the crude extracellular fluid against water, analysis showed that the yield of the β-emulsan was 16 units per ml with a specific activity of 50 units per mg determined by the standard assay technique. The crude protoemulsan contained almost 5% total ester content when measured by the hydroxamic acid test, assuming the average molecular weight of the fatty acid esters to be 230. The corresponding apo-β-emulsan, obtained by hot phenol extraction in accordance with the deproteinization technique described below in Section 13.7, contained an ester content between 2 to 3% when measured by the hydroxamic acid test.

13.6. PREPARATION OF APO-α-EMULSAN

Various samples of emulsan contain between 5% to 15% protein by weight, which reflects the degree of purity of the bioemulsifier. In order to ascertain whether or not the protein moiety was essential for emulsifying activity, α-emulsan which had been prepared by growing Acinetobacter Sp. ATCC 31012 on an ethanol medium was deproteinized by the hot phenol method described by O. Westphal et al. in the monograph edited by R. L. Whistler, "Carbohydrate Chemistry", Academic Press, Inc., New York, 1965, pp. 83-91.

One gram of such α-emulsan, dissolved in 200 ml water with the aid of a few drops of concentrated ammonium hydroxide, was brought to 65°-68° C., and then added to an equal volume of 90% phenol which had been preheated to 65° C. The mixture was stirred vigorously for 15 minutes at 65° C. and then cooled to 10° C. in an ice bath. The resulting emulsion was centrifuged at 5,000×g for 30 minutes. After transferring the viscous aqueous phase to a flask, the remaining phenol layer and interface were extracted three more times with 200 ml water. The combined water extracts were dialyzed extensively against several changes of distilled water and then freeze-dried to obtain 850 mg (85% yield) of apo-α-emulsan as a white fluffy solid.

The remaining phenol fraction and interphase were suspended in water, dialyzed extensively against distilled water and freeze-dried, yielding 100 mg (10% yield) of a yellowish proteinaceous material which represents the denatured protein derived from such α-emulsan.

The ability of each of these fractions to emulsify gas-oil was then determined using the standard assay technique. Emulsion formation was measured in 125 ml flasks containing 7.5 ml Tris-Mg buffer [200 mM tris-(hydroxymethyl)aminomethane hydrochloride, pH 7.4; 10 mM magnesium sulfate] 0.05 ml Gach-Saran gas-oil and either 75 mcg of α-emulsan, 75 mcg of apo-α-emulsan or 15 mcg of the denatured protein obtained by phenol extraction of such emulsan. Flasks were agitated by reciprocal shaking (150 strokes per minute) for one hour at 26° C. Contents of the flasks were then transferred to Klett tubes for measurement of turbidity in a Klett-Summerson colorimeter fitted with a green filter. The results of these tests are summarized in Table XI, the specific activity (reported in units per mg dry weight) having been determined from the standard curve (Curve 1-B) shown in FIG. 1.

TABLE XI

| Fraction | Emulsification of Gas-Oil | |
|---|---|---|
|  | Amount (mcg) | Specific Activity (units per mg) |
| α-Emulsan | 75 | 276 |
| Denatured protein | 15 | 0 |
| Apo-α-emulsan | 75 | 146 |

The data contained in Table XI show that all of the emulsifying activity is in the O-lipoacyl heteropolysaccharide and that none of the activity is associated with the denatured protein fraction.

From additional experimental work on apo-α-emulsan, it was found that addition of 0.2 and 2.0 mcg/ml of this denatured protein to 10 mcg/ml of apo-α-emulsan resulted in 25% and 66% "stimulations" of emulsifying activity, respectively, which actually is a measure in the amount of turbidity obtained in the standard emulsifier assay which, in turn, is believed to be related to emulsifying activity. This increase in turbidity of hydrocarbon substrate when protein was added to apo-α-emulsan was not specific to the denatured protein derived by phenol extraction of α-emulsan, since different proteins, such as bovine serum albumin, lysozyme, hexokinase and denatured alcohol dehydrogenase, also result in increased turbidities in the emulsification of gas-oil when such proteins are added to apo-α-emulsan.

13.7. PREPARATION OF APO-β-EMULSAN

The hot phenol method of O. Westphal et al., supra, may also be used to extract the associated protein contained in β-emulsan and thereby form the corresponding apo-β-emulsan. Using the experimental method described above in Section 13.5, the β-emulsan which had been prepared by growing Acinetobacter Sp. ATCC 31012 on a hexadecane medium was deproteinized to form the corresponding apo-β-emulsan. All of the emulsifying activity was found to be in the O-lipoacyl heteropolysaccharide and none of such activity was found to be associated with the denatured protein fraction.

13.8. PREPARATION OF ψ-EMULSAN

Mild base hydrolysis of emulsans will O-deacylate the lipopolysaccharide without affecting the N-acyl groups, which technique may be used to prepare the ψ-emulsans. Ten milliliters of an aqueous solution containing 2.5. mg/ml of α-emulsan were treated with an equal volume of 0.2 M NaOH at 98° C. for 2 hours. The solution was then cooled in an ice bath and carefully neutralized to pH 7.0. The neutralized solution was extensively dialyzed against water and lyophilized, yielding 20 mg (80%) of ψ-emulsan having a Specific Emulsifying Activity of 76 units per mg. The total ester content of the ψ-emulsan was 1% by the hydroxamic acid test. The reduced viscosity of this ψ-emulsan was 317 cc/gram.

13.9. PREPARATION OF PROEMULSAN

Base hydrolysis of the emulsans, apoemulsans or ψ-emulsan will completely O-deacylate and partially N-deacylate the biopolymer, hydrolyzing any associated protein at the same time. The resultant products are the proemulsans. Fifty mg of pro-α-emulsan in 30 ml of 2% KOH in methanol solution were left at room temperature for 96 hours. After removal of the methanol at low ressure, 15 ml of water were added and the pH adjusted to ph 2.0. The free acids were removed by ether extraction, and the aqueous solution was dialyzed and lyophilized, yielding 37 mg (74%) of proemulsan. The ester content of the proemulsan, as assayed by the hydroxyamic acid test, was zero. Moreover, the product has no emulsification activity when assayed by the standard emulsification test. Elemental analysis: C 36.5%, H 7.0%, N 6.5%.

13.10. PURIFICATION OF α-EMULSAN BY PRECIPITATION WITH AMMONIUM SULFATE

A late exponential culture (1:1000 dilution) of Acinetobacter Sp. ATCC 31012 was grown at 30° C. in a New Brunswick 14-liter fermenter using an aqueous medium containing 14 g per liter of dibasic acid potassium phosphate [$K_2HPO_4.3H_2O$], 6 g per liter of monobasic potassium phosphate, 0.2 g per liter of magnesium sulfate [$MgSO_4.7H_2O$], 4 g per liter of ammonium sulfate and 20 ml per liter of absolute ethanol. The fermentation was conducted using aeration at about 15 liters per minute and agitation at 100 rpm without baffles, adding ethanol as required.

When the fermentation had proceeded about 3 days, the medium was allowed to cool and 1760 g of ammonium sulfate were added slowly, with stirring, directly to 10-liters of cooled fermentation broth without prior removal of the cells (30% ammonium sulfate saturation). After standing overnight, the supernatant fluid was collected by decantation. The precipitate was suspended in 30% saturated ammonium sulfate and centrifuged at 10,000×g for 15 minutes. The combined supernatant fluids were further clarified by passage through a thin layer of Kieselgel. To the cell-free supernatant fluid was added an additional portion (62 g per liter) of ammonium sulfate to reach a final concentration of 40% saturation.

The resulting precipitate collected by centrifugation at 10,000×g for 15 minutes, was dissolved in 200 ml of water, extracted with ether, dialyzed against distilled water and lypophilized. The yield of α-emulsan was 2.1 g from 10-liters of fermentation broth, with a Specific Emulsification Activity of 330 units per mg.

13.11. PURIFICATION OF α-EMULSAN BY PRECIPITATION WITH QUATERNARY AMMONIUM SALTS

One gram of crude α-emulsan was dissolved in 100 ml of water to yield a clear viscous solution. Twenty milliliters of a 5% w/v aqueous solution of cetyltrimethyl ammonium bromide was added with mixing at room temperature. After allowing the precipitate to aggregate a few minutes, the mixture was centrifuged at 5,000×g for 10 minutes. The pellet fraction, which contained all the emulsifying activity, was washed once with distilled water. The washed cetyltrimethyl ammonium bromide precipitate was dissolved in 100 ml of 0.1 M sodium sulfate. A small amount of precipitate remaining was removed by centrifugation at 10,000×g for 30 minutes. One gram of potassium iodide was then added to the clear solution with mixing. The cetyltrimethyl ammonium iodide precipitate that formed was removed by centrifugation at 10,000×g for 15 minutes. The remaining supernatant fluid was dialyzed extensively against distilled water and lyophilized to yield a white solid. This material had a Specific Emulsification Activity of 350 units per mg.

A sample of the CTAB-purified α-emulsan was subjected to acid hydrolysis at 98° C. in 5 M HCl for 6 hours to liberate any glucose that may have been present in the biopolymer. The hydrolyzed material was then analyzed by thin layer chromatography on a cellulose-F plate; silver nitrate staining showed only a trace of glucose, probably as an impurity.

13.12. PURIFICATION OF β-EMULSAN BY HEPTANE PARTITIONING

Using the medium described above in Section 13.10 with 0.2% (v/v) hexadecane being substituted as the primary assimilable carbon source in place of ethanol, Acinetobacter Sp. ATCC 31012 was grown at 30° C. in New Brunswick 14-liter fermenters for 4 days.

Twenty-seven liters of the hexadecane-grown culture were cooled and the cells removed by centrifugation in a Sorvall KSB continuous flow centrifuge. The supernatant fluid was then extracted twice with ⅓ volume of ether. Residual ether in the aqueous phase was removed by bubbling with filtered nitrogen gas. The ether phase contained no measurable emulsifying activity and was discarded.

The aqueous phase was filtered successively through 3, 1.2, 0.8 and 0.45 micron Millipore filters, and the clear filtrate was then extracted four times with 0.15 volume heptane. Approximately 10% of the emulsifying activity which remained in the aqueous phase was discarded.

The heptane fractions were combined and evaporated to a yellow syrup in vacuo. After extraction with ether, the syrup was dissolved in 100 ml of 50% aqueous methanol. The resulting viscous solution was dialyzed against several changes of distilled water and lyophilized. The yield of lyophilized β-emulsan was 1.5 g, with an extraordinarily high specific activity of 205 units per mg.

A sample of this material was subjected to base hydrolysis for 72 hours at room temperature, using an aqueous solution of 90% methanol containing 2.5% KOH. After removal of the methanol in vacuo, addition of water and acidification to pH 1, the fatty acids were extracted with ether, methylated with diazomethane and were then subjected to gas chromatographic analysis. The chromatograph revealed the presence of 2-hydroxydodecanoic acid (A) and 3-hydroxydodecanoic (B) acid in a weight ratio of A/B equal to 0.83.

13.13. AMMONIUM SULFATE FRACTIONATION OF APO-α-EMULSAN

The phenol extraction method described above in Section 13.6 was repeated on 820 mg of α-emulsan. After three phenol extractions, the combined water extracts were extracted four times with an equal volume of ether to remove residual phenol. Following evaporation of ether, the viscous aqueous phase was cooled to 5° C. and brought to 32.5% ammonium sulfate saturation, no precipitation having formed at 30% saturation. After standing for one hour at 5° C., the clear translucent precipitate was collected by centrifugation at 5,000×g for 30 minutes at 5° C.

The procedure was repeated to obtain a slightly turbid second precipitate between 32.5% and 35% saturation and another small precipitation between 35% and 40% saturation. No additional precipitate formed between 40% and 60% saturation. Each of the precipitates was dissolved and was dialyzed at 2°–5° C. successively against distilled water, 0.05 N hydrochloric acid (24 hours) and double distilled water. The same procedure was also followed with the remaining 60% saturated solution. Each of the resulting solutions remaining after such purification was freeze-dried and analyzed. The results of such analyses are set forth in Table XII.

The analytical data contained in Table XII show that over 99% of the emulsifying activity of apo-α-emulsan precipitated in the two fractions between 30% and 35% ammonium sulfate saturation. These two apo-α-emulsan fractions were characterized by similar Specific Emulsification Activities and had the same proportions of O-ester, carboxylic acid and hexose. Moreover, both of the active fractions had high specific viscosities. None of the fractions contained significant quantities of protein.

TABLE XII

Analyses of Ammonium Sulfate-Precipitated Fractions of Apo-α-emulsan

| Ammonium Sulfate Concentration (%) at which Precipitation Occurred | Weight of Precipitate (mg) | Emulsifying Activity Klett Units | Emulsifying Activity Specific Activity | Reduced Viscosity (cc/g) | Protein (%) | O—Ester (μ moles per mg) | Carboxylic Acid (μ moles per mg) | Hexose[a] (μ moles per mg) |
|---|---|---|---|---|---|---|---|---|
| 30–32.5 | 379 | 66,500 | 175 | 810 | 0.3 | 0.66 | 1.5 | 0.27 |
| 32.5–35 | 194 | 34,500 | 178 | 570 | 0.15 | 0.63 | 1.5 | 0.33 |
| 35–40 | 25 | 780 | 31 | 400 | 0.5 | 0.81 | — | 0.20 |
| 40–60 | 82 | 0 | 0 | — | 0.7 | — | — | 0.08 |

[a]The small amounts of hexose (glucose equivalents) which were detected are due to the presence of a small amount of a contaminating material which coprecipitated with the apo-α-emulsan, but which could be removed following fractionation of the apo- -emulsan with cetyltrimethyl ammonium bromide. This contaminating material was a lipopolysaccharide which contained glucose. It had no emulsifying activity when assayed by the standard emulsification technique.

13.14. EMULSIFICATION OF PETROLEUM FRACTIONS BY α-EMULSANS AND β-EMULSANS

The presence of a higher O-lipoester content in α-emulsans compared to β-emulsans results in significant differences in the emulsification activity of these Acinetobacter bioemulsifiers. This conclusion was demonstrated by a series of tests which were conducted to determine the effect of both bioemulsifiers on various types of petroleum fractions which are widely used within and sold by the oil industry.

In each of these tests, emulsion formation was measured in 125 ml rubber-stoppered flasks containing 5 ml of filtered sea water, 8 mg/ml of hydrocarbon and 50 mcg/ml of the particular Acinetobacter bioemulsifier, the α-emulsan having been prepared by growing Acinetobacter Sp. ATCC 31012 on an ethanol medium while the β-emulsan was prepared by growing the organism on a hexadecane medium. The α-emulsans were purified by the ammonium sulfate fractionation technique described above in Section 13.10 while the β-emulsans were purified by the heptane partitioning technique described above in Section 13.12.

Flasks were agitated by gyratory shaking (280 rpm) or by reciprocal shaking (150 strokes per minute) for 2 hours at 25° C. Contents of the flask were then transferred to Klett tubes for measurement of turbidity in a Klett-Summerson colorimeter fitted with a green filter. Readings were taken after standing undisturbed for 10 minutes. Controls lacking either the particular Acinetobacter emulsifier or hydrocarbon yielded readings of less than 5 Klett units. The results of these tests are summarized in Table XIII.

TABLE XIII

Emulsification of Petroleum Fractions by α-Emulsans and β-Emulsans

| Petroleum Fraction (8 mg/ml) | Emulsifier (50 mcg/ml) | Emulsion Gyratory | (K.U.) Reciprocal |
|---|---|---|---|
| Crude Oils | | | |
| Darius | α-Emulsan | 650 | 1090 |
| Agha Jari | α-Emulsan | 720 | 950 |
| Agha Jari | β-Emulsan | 780 | — |
| Rostam | β-Emulsan | 758 | — |
| Gas-Oils | | | |
| Darius | α-Emulsan | 300 | 800 |
| Gach Saran | α-Emulsan | — | 500 |
| Belayim Marine | α-Emulsan | 100 | — |
| Agha Jari | α-Emulsan | 195 | 840 |

TABLE XIII-continued

Emulsification of Petroleum Fractions by
α-Emulsans and β-Emulsans

| Petroleum Fraction (8 mg/ml) | Emulsifier (50 mcg/ml) | Emulsion Gyratory | (K.U.) Reciprocal |
|---|---|---|---|
| Agha Jari Kerosenes | β-Emulsan | — | 420 |
| Darius | α-Emulsan | 42 | 160 |
| Belayim Marine | α-Emulsan | 35 | — |
| Agha Jari | α-Emulsan | 41 | 110 |
| Agha Jari Miscellaneous | β-Emulsan | — | 125 |
| Diesel Oil | α-Emulsan | 290 | — |
| Diesel Oil | β-Emulsan | — | 490 |
| Bunker C Fuel Oil | α-Emulsan | — | 680 |
| Bunker C Fuel Oil | β-Emulsan | — | 35 |
| Light Petroleum Oil | β-Emulsan | — | 218 |
| Gasoline (83 Octane) | α-Emulsan | — | 89 |

Analysis of the data contained in Table XIII show that although α-emulsan and β-emulsan are both excellent emulsifiers for crude oils and are both only fair emulsifiers for kerosenes, α-emulsan is much more effective than β-emulsan in the emulsification of gas-oils. In fact, emulsions of gas-oils were as stable as crude oil emulsions, the major reason for the higher Klett readings of crude oil emulsions than those for gas-oil emulsions being the dark color of crude oil compared to gas-oil. Bunker C fuel oil was emulsified by α-emulsan but not by β-emulsan. Considering that the darker color of crude oil may have obscured the relative emulsification activities of both bioemulsifiers, the data show that in general better emulsions were obtained with α-emulsan than with β-emulsan and with reciprocal rather than with gyratory shaking.

13.15. EMULSIFICATION OF MIXTURES OF PETROLEUM FRACTIONS AND PURE HYDROCARBONS BY α-EMULSAN

To determine whether emulsans exhibit any specificity in the emulsification of different types of hydrocarbons, a series of tests were conducted to measure the effect of α-emulsan in the emulsification of mixtures of various petroleum fractions and pure hydrocarbons.

In each of these tests, emulsion formation was measured in 125 ml rubber-stoppered flasks containing 5 ml of filtered sea water, 8 mg/ml of total substrate (petroleum fraction plus additive) and 50 mcg of α-emulsan. All mixtures of hydrocarbons were 1:1 (v/v). In some of the tests, fractions of Agha Jari crude oil were used, the fractions having been prepared by the procedure of A. Jobson et al., App. Microbiol., 23, 1082–1089 (1972), under which procedure Fractions 1, 2 and 3 correspond to the aliphatic (saturates), aromatic and polar aromatic fractions, respectively. As before, the α-emulsan was prepared by growing Acinetobacter Sp. ATCC 31012 on an ethanol medium and was purified by the ammonium sulfate fractionation technique.

Flasks were agitated by reciprocal shaking (150 strokes per minute) for 2 hours at 25° C. Contents of the flask were then transferred to Klett tubes for measurement of turbidity in a Klett-Summerson colorimeter fitted with a green filter. Readings were taken after standing undisturbed for 10 minutes. The results of these tests are summarized in Table XIV.

TABLE XIV

Emulsification of Mixtures of Petroleum
Fractions and Pure Hydrocarbons by α-Emulsan

| Petroleum Fraction | Additive | Emulsion (K.U.) |
|---|---|---|
| Kerosene | none | 190 |
| Kerosene | hexadecane | 68 |
| Kerosene | 2-methylnaphthalene | 1050 |
| Gasoline | none | 115 |
| Gasoline | hexadecane | 230 |
| Gasoline | 2-methylnaphthalene | 1100 |
| Agha Jari | | |
| Fraction 1 | none | 130 |
| Fraction 2 | none | 60 |
| Fraction 3 | none | 105 |
| Fraction 1 | Fraction 3 | 1050 |
| Fraction 2 | Fraction 3 | 1500 |
| Fraction 3 | Fraction 3 | 80 |

The data contained in Table XIV show that the efficacy of α-emulsan in the emulsification of hydrocarbons is dependent on the relative concentrations of aliphatic and aromatic (or cyclic) compounds in the hydrocarbon substrate. For example, the ability of emulsan to emulsify kerosene and gasoline was enhanced greatly by 2-methylnaphthalene but not by hexadecane. The requirement that the hydrocarbon substrate contain both aliphatic and aromatic (or cyclic) components was further supported by the results obtained in the emulsification of mixtures of column fractionated crude oil. Although crude oil itself is emulsified by emulsan, none of the fractions were good substrates by themselves. Mixtures containing one fraction rich in aliphatics (Fraction 1) and the other rich in aromatics (Fractions 2 or 3) were efficiently emulsified.

13.16. CLEANING OIL-CONTAMINATED VESSELS

Aqueous solutions in sea water or fresh water (the latter containing a suitable divalent cation, such as magnesium) of α-emulsans are excellent emulsifying agents for cleaning and recovering hydrocarbonaceous residues, including residual crude oil, from oil-contaminated tankers, barges, storage tanks, tank cars and trucks, pipelines and other containers used to transport or store crude oil or petroleum fractions. Washing the oil-contaminated surfaces of such vessels with an aqueous solution containing from about 10 mcg/ml to about 20 mg/ml of α-emulsan readily forms an oil-in-water emulsion of such hydrocarbonaceous residues provided that the solution contains from about 1 to about 100 mM, and preferably from about 5 to about 40 mM, of at least one suitable divalent cation, which are normally present in sea water and "hard" tap water. Moreover, the α-emulsan need not be purified, since a cell-free fermentation broth containing α-emulsans resulting from growing Acinetobacter Sp. ATCC 31012 on a suitable medium can be used directly or after suitable dilution.

Using the data which is set forth above in Sections 8 and 9, processes can be designed to clean any oil-contaminated vessel and to recover the hydrocarbonaceous residue from the resultant oil-in-water emulsions, either by breaking the emulsion physically or chemically. Depending upon the amount and composition of the oil or hydrocarbonaceous residue to be cleaned, the aggregate amount of α-emulsan may be as low as 1 part by weight (dry weight basis) per 1,000 to 10,000 parts by weight of hydrocarbon, the higher concentrations of α-emulsan yielding more stable emulsions.

To show the use of the cell-free fermentation broth as an emulsifying agent for such cleaning, Acinetobacter Sp. ATCC 31012 was cultivated in a 15 liter glass fermenter containing 122 g of dibasic potassium phosphate [$K_2HPO_4.3H_2O$], 40 g of monobasic potassium phosphate, 1.33 g of magnesium sulfate [$MgSO_4.7H_3O$], 13.3 g of urea and deionized water to a final volume of 10 liters. The medium was sterilized for 30 minutes at 121° C., after which 200 ml of absolute ethanol (2% by volume) was added. The final pH of the ethanol-salts medium was 7.0. After the medium had cooled to 30° C., 500 ml of a late exponential culture of Acinetobacter Sp. ATCC 31012 grown in the same medium was added to the glass fermenter and the culture maintained at 30° C., with an air flow of 3.5 liters per minute and an agitation speed of 200 rpm (no baffles). During the course of fermentation the pH dropped to 6.0. Throughout the fermentation, foam was controlled by periodic addition of silicone defoamer (in the form of a spray).

Under these conditions, the fermentation broth contained 260 units per ml of α-emulsan after 72 hours and 7.4 g per liter of biomass (dried at 90° C. for 16 hours). After removal of the cells by centrifugation or filtration, the resultant cell-free fermentation broth could be used to wash crude oil from the oil-contaminated surface of a steel container which simulated the inner wall of a tank which had been emptied of crude oil.

13.17. EFFECT OF MOBILITY CONTROL POLYSACCHARIDES ON EMULSION FORMATION WITH EMULSANS

The bacterial exocellular heteropolysaccharide (XANFLO SFL 14630) produced by the Kelco Division of Merck & Co., Inc., which has been recommended as a mobility control polymer for enhanced oil recovery, was tested in varying concentrations in conjunction with 20 mcg/ml of α-emulsan to determine the effect of such material on the emulsification of gas-oil. In each of these tests, 0.1 ml of Gach-Saran gas-oil was added to 125 ml Ehrlenmeyer flasks containing 7.5 ml of Tris-Mg buffer [50 mM tris-(hydroxymethyl)aminomethane hydrochloride, pH 7.2; 10 mM magnesium chloride], 20 mcg/ml of α-emulsan and varying concentrations of the mobility control polysaccharide. Several tests were also run without the α-emulsan to determine whether the mobility control polymer emulsified the hydrocarbon.

The flasks were agitated by gyratory shaking (280 rpm) in a New Brunswick G24 incubator shaker for one hour at 30° C. Contents of the flasks were then transferred to Klett tubes for measurement of turbidity in a Klett-Summerson colorimeter fitted with a green filter. Readings were taken after standing undisturbed for 10 minutes. The results of these tests, which are summarized in Table XV, are expressed as the percentage increase (+) or decrease (−) in the turbidity of the emulsion resulting from the addition of varying concentrations of the mobility control polymer.

TABLE XV

| Effect of Mobility Control Polysaccharide on Emulsion Formation | | |
|---|---|---|
| Mobility Control Polysaccharide (mcg/ml) | α-Emulsan (mcg/ml) | Relative Emulsifying Ability (%) |
| 1 | 20 | −17.0 |
| 2 | 20 | +3.1 |
| 5 | 20 | −7.3 |
| 10 | 20 | +41.7 |
| 20 | 20 | +27.2 |

TABLE XV-continued

| Effect of Mobility Control Polysaccharide on Emulsion Formation | | |
|---|---|---|
| Mobility Control Polysaccharide (mcg/ml) | α-Emulsan (mcg/ml) | Relative Emulsifying Ability (%) |
| 40 | 20 | +20.6 |
| 10–150 | None | No Activity |

As shown in Table XV, it appears that the use of the mobility control polysaccharide in conjunction with the emulsan is capable of stimulating emulsifying activity by about 40% at a concentration of 10 mcg/ml, which suggests the potential advantages for using both additives in a chemically-augmented "slug" to be injected into a petroleum reservoir for enhanced oil recovery. By itself, however, this mobility control polymer had no ability to emulsify the hydrocarbon.

13.18. ADSORPTION OF EMULSANS ON CLAYS

Because of the importance of aluminosilicate clays, such as kaolin and bentonite, in many industrial and petroleum production and refining processes, a series of tests was conducted to determine whether emulsans adsorped onto the surface of such aluminosilicate clays. Bentonite was selected for these tests, since it contains up to 90% by weight of montmorillonite, the structure of which corresponds to the theoretical formula $(OH)_4Si_8Al_4O_{20}.xH_2O$ and is responsible for its high sorptive power and ion-exchange capacity.

The theoretical treatment of adsorption from a mixed solution is somewhat complicated, since it involves competition between solutes and solvents for the solid surface. In these tests, adsorption from solution was analyzed by the Freundlich equation:

$$x/m = a \cdot C^{1/n}$$

where x represents the amount of solute adsorped by the mass m of solid, C represents the solute concentration and a and n are experimentally-determined constants. Experimentally, $x = (C_o - C)V$, where $C_o$ and C are the initial and equilibrium solute concentrations, respectively, and V is the volume of solution in contact with the sorbent. in this case, an apparent adsorption isotherm can be expressed if x/m is plotted against equilibrium solute concentration.

In each of these tests, the emulsan used was an α-emulsan purified in accordance with the ammonium sulfate fractionation technique described above in Section 13.10. Prior to drying, the α-emulsan contained about 7% by weight of protein, about 16% by weight of ash and about 38% by weight of moisture. Aqueous solutions of this α-emulsan were prepared by dissolving the dry emulsan in 0.02 M solutions of Tris-Mg buffer [20 mM tris-(hydroxymethyl)aminomethane HCl containing 10 mM magnesium sulfate]. Nonactivated, technical grade bentonite was used as the sorbent.

Adsorption of α-emulsan from a given volume of solution on a given mass of bentonite was carried out in 100 ml or 50 ml Ehrlenmeyer flasks, with shaking for 1 hour at 100 strokes per minute. The equilibrium solutions were separated from the bentonite by centrifugation or filtration. Emulsan assays were performed by the standard assay technique. The results of the tests are summarized in Table XVI.

TABLE XVI

Adsorption of α-Emulsan on Bentonite

| Bentonite (mg) | α-Emulsan $C_o$ | (mg/ml) C | % Bound |
|---|---|---|---|
| 10 | 0.11 | 0.032 | 71 |
| 20 | 0.11 | 0.028 | 75 |
| 25 | 0.10 | 0.006 | 94 |
| 40 | 0.11 | 0.004 | 96 |
| 60 | 0.11 | <0.001 | >99 |

The data contained in Table XVI show that the adsorption of α-emulsan to bentonite is a function of bentonite concentration. About 70% of the emulsan is adsorbed when the ratio of bentonite to emulsan is 100:1, while more than 95% of the emulsan is adsorbed at ratios of 400:1 or higher.

13.19. FLOCCULATION OF CLAYS BY EMULSANS

Adsorption of emulsan on bentonite results in flocculation of suspended particles of the clay, with sedimentation occurring about 5 to 10 times faster than in the absence of emulsan. To a solution of 50 ml sea water and 50 ml Tris buffer containing 100 mcg/ml of α-emulsan was added 1.6 g of non-activated, technical-grade bentonite with mixing, and the resultant dispersion was then poured into a calibrated glass cylinder and allowed to settle at room temperature. As a control, a parallel experiment was conducted without using the α-emulsan.

Figure 18:
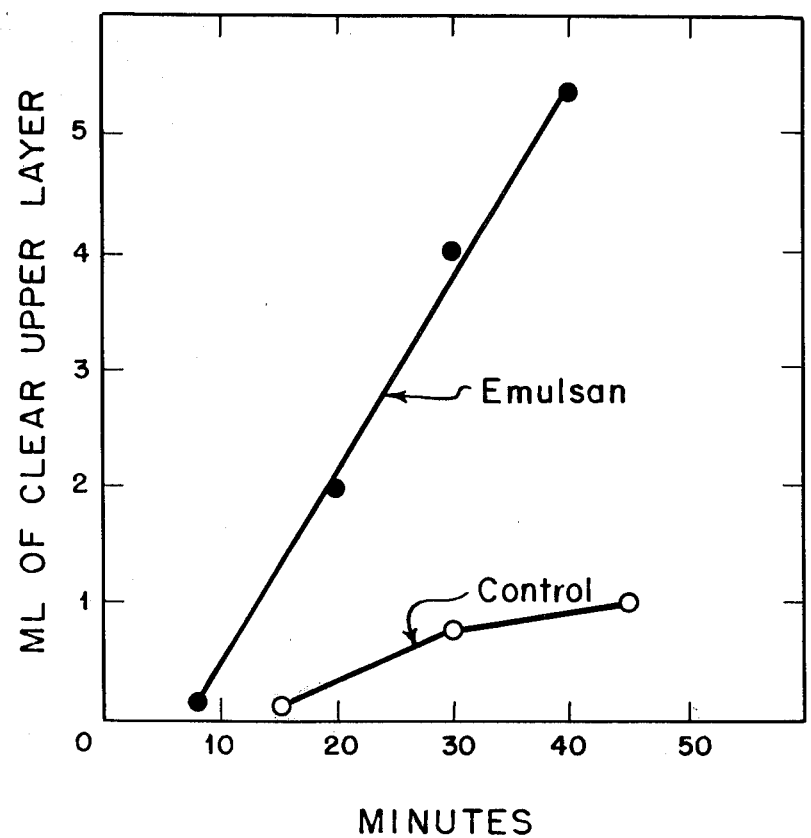
FIG. 18 is a graphical representation of the kinetics of bentonite flocculation by emulsan, showing the relationship between the amount of clear upper layer which appears during sedimentation as a function of time when a given amount of bentonite is dispersed in a standardized control solution containing no added bioemulsifier and in the same solution containing a given concentration of emulsan and both dispersions are allowed to settle.

The results of these tests, which are graphically illustrated in FIG. 18, show that the dilute (100 ppm) solution of α-emulsan enhanced the rate of sedimentation by a factor of five over that obtained in the control. More importantly, the supernatant fluid obtained following the emulsan-mediated flocculation was clear, while the supernatant fluid obtained in the control remained opalescent even after prolonged standing.

13.20. FLOCCULATION OF CLAYS BY PROEMULSANS

Proemulsans are even more effective than emulsans in the flocculation of suspended particles of bentonite. Table XVII summarizes an experiment in which the flocculating of 0.4 g bentonite in 14 ml of either Tris buffer, pH 7.26, or phosphate buffer, pH 6.5, was measured in the presence of α-emulsan, proemulsan and no addition. The final concentration of α-emulsan was 0.05 mg per ml, whereas the final concentration of proemulsan was 0.045 mg/ml. After vigorous shaking for 2 minutes, the suspension was centrifuged at 25,000 rpm for 60 minutes. The data presented in Table XVIII were obtained by measuring the clarified upper layer in the centrifuge tube. Similar results were obtained with ψ-emulsan as with proemulsan.

TABLE XVII

Flocculation of Bentonite by α-Emulsan and Proemulsan

| Sample | Volume of Clear Upper Layer (ml) | |
|---|---|---|
| | PH 6.5 | pH 7.26 |
| 1. No addition | 1.1[a] | 1.1 |
| 2. α-Emulsan | 1.8[a] | 2.0 |
| 3. Proemulsan | 3.0 | 4.6 |

[a]The upper layer was opalescent.

13.21. BREAKING EMULSAN-INDUCED EMULSIONS

Since emulsans form stable oil-in-water emulsions and, moreover, since emulsans are adsorbed onto bentonite, a series of tests were conducted to determine the behavior of such emulsan-induced emulsions in the presence of bentonite. In one test, an emulsion of Agha Jari crude oil (1 ml in 10 ml sea water) containing about 0.1 mg/ml of α-emulsan was prepared by the standard technique of adding the oil to the solution of α-emulsan in a flask and agitating the flask by gyratory shaking for one hour at room temperature. After 2 days, 1 g of preswelled bentonite was added to the stable emulsion and the dispersion was shaken intensively for about 20 seconds, after which it was transferred to a tube and allowed to settle. After 15 minutes, a breakage of the emulsion was observed. After 20 hours, two layers had separated, the upper layer being clear while the lower layer was a gel-like sediment which occupied about one-half the prior volume of the emulsion.

In another test, an emulsion of Agha Jari crude oil (0.1 ml) in 7.5 ml Tris-Mg buffer solution [50 mM tris-(hydroxymethyl)aminomethane hydrochloride, pH 7.2; 10 mM magnesium chloride] containing 0.08 mg/ml of α-emulsan was prepared by the standard technique as before. As a control, 0.1 ml of the crude oil in 7.5 ml of buffer solution was shaken under the same conditions. Both samples were transferred to tubes containing 0.5 g of bentonite, shaken for 30 seconds and the contents allowed to settle. After 15 hours, there was a complete breakage of the emulsan-induced emulsion. Moreover, the flocculated sediment formed in the presence of α-emulsan was two times larger by volume than the sediment from the control test.

13.22. REMOVAL OF OIL FROM SAND BY EMULSAN

One gram of white sand was preadsorbed with either 0.1 ml, 0.2 ml, or 0.3 ml (saturated) Darius crude oil (light weight Persian crude) in duplicate. The sand samples were then transferred to 100 ml Ehrlenmeyer flasks containing 10 ml Tris-mg buffer [50 mM tris-(hydroxymethyl)aminomethane hydrochloride, pH 7.2; 10 mM magnesium sulfate]. To one each of the samples containing 0.1 ml, 0.2 ml, or 0.3 ml of the crude oil was added α-emulsan at a final concentration of 0.1 mg/ml. The remaining three samples (without the emulsan) served as controls. The samples were shaken at 140 strokes per minute for 30 minutes at 30° C. in a shaking water bath.

Following the shaking, the samples were allowed to settle for one hour, and the aqueous phase was separated from the sand by decantation. Each of the sand samples was washed twice with 10 ml Tris-Mg buffer, and the decanted washed fluids combined. The sand samples and the aqueous phase (together with the wash fluids) were each separately extracted with diethyl ether and the ether extract dried under nitrogen in tared flasks. Table XVIII summarizes the results of these tests, where the amount of oils removed by α-emulsan is measured as the amount of ether-extracted material in the water phase and the amount of oil remaining on the sand is measured as the amount of ether-soluble material extracted from the washed sand.

TABLE XVIII

Effect of α-Emulsan on Removal of Crude Oil from Sand

| Crude Oil on Sand (ml) | Emulsan (mg/ml) | Oil Removed from Sand (mg) | Oil Remaining on Sand (mg) | Removal (%) |
|---|---|---|---|---|
| 0.1 | — | <5 | 65 | <10 |
| 0.1 | 0.1 | 57 | <5 | >90 |
| 0.2 | — | 15 | 108 | 12 |
| 0.2 | 0.1 | 96 | 12 | 89 |
| 0.3 | — | 33 | 172 | 16 |
| 0.3 | 0.1 | 165 | 14 | 92 |

The effect of α-emulsan in removing oil from sand is clearly demonstrated in Table XVIII. In the presence of 0.1 mg/ml, over 90% of the crude oil is removed. This is probably a lower estimate since ether extraction of sand particles which had not settled before the initial separation of the phases would contribute to the overall amount of material extracted from the aqueous phase in the control. Very little (<10%) of the oil was removed without shaking. During these tests, it was observed that the solubilized oil emulsified in those samples to which α-emulsan was added. Moreover, the addition of the α-emulsan to a flask containing sand and buffer prior to preadsorption of the oil prevented the subsequent adsorption of oil to the sand during the shaking.

From the data contained in Table XVIII, it is clear that emulsans may be used in enhanced recovery processes for recovering oil which is contained in sand or sandstone formations, in which processes a chemically-augmented "slug" comprising water or brine and one or more added chemicals is injected into a petroleum reservoir located in a sand or sandstone formation and is displaced through the reservoir to recover crude oil. In addition, dilute solutions of emulsans (which are biodegradable) may be used in oil spill management to emulsify oil spills deposited on beach sand so that the oil may be dispersed and subsequently microbiologically degraded.

13.23. REMOVAL OF OIL FROM LIMESTONE BY EMULSAN

A series of tests was conducted to determine the ability of emulsan to remove oil from limestone, since enhanced oil recovery processes based on chemical flooding of petroleum reservoirs located in reservoir formations (in which processes a chemically-augmented "slug" of water or brine and one or more added chemicals is injected into a petroleum reservoir in a limestone formation and is displaced through the reservoir to recover crude oil) will require efficient emulsifiers capable of removing oil from limestone, which chemically is calcium carbonate.

Four 4-gram samples of calcium carbonate (crushed limestone) were each preadsorbed with 0.8 g Aghi Jari crude oil. The oil-impregnated limestone samples were then transferred to 100 ml Ehrlenmeyer flasks containing 20 ml Tris-Mg buffer [50 mM tris-(hydroxymethyl)aminomethane hydrochloride, pH 7.2; 10 mM magnesium sulfate]. To each of three of the samples was added varying amounts of α-emulsan (2, 5 and 10 mg, respectively) while the remaining sample (without the emulsan) served as a control. The samples were shaken at 140 strokes per minute for 30 minutes at 30° C. in a shaking water bath.

Following the shaking, the samples were allowed to settle for 1 hour, and the aqueous phase was separated from the limestone by decantation. Each of the limestone samples was washed twice with 10 ml Tris-Mg buffer, and the decanted washed fluid combined. The limestone samples and the aqueous phase (together with the wash fluids) were each separately extracted with diethyl ether and the ether extract dried under nitrogen in tared flasks. Table XIX summarizes the results of these tests, where the amount of oils removed by α-emulsan is measured as the amount of ether-extracted material in the water phase and the amount of oil remaining on the limestone was calculated by difference.

TABLE XIX

Effect of α-Emulsan on Removal of Crude Oil from Limestone

| Sample | Emulsan (mg/ml) | Oil Removed (g) | Oil Remaining (g) | Removal (%) |
|---|---|---|---|---|
| A | — | 0.06 | 0.74 | 14 |
| B | 0.1 | 0.71 | 0.09 | 89 |
| C | 0.25 | 0.75 | 0.06 | 93 |
| D | 0.5 | 0.78 | 0.02 | 98 |

The effect of α-emulsan in removing oil from limestone is clearly demonstrated in Table XIX. In the presence of 0.1 mg/ml, over 89% of the crude oil was removed; at α-emulsan concentrations of 0.5 mg/ml, over 98% of the crude oil was removed. As in the case of the tests described above in Section 13.22, this is probably a lower estimate since ether extraction of limestone particles which has not settled before the initial separation of the phases would contribute to the overall amount of material extracted from the aqueous phase in the control.

Because emulsans and particularly the α-emulsans (on a weight-for-weight basis) are probably the most efficient oil-in-water emulsifiers in existence and because these extracellular lipopolysaccharides tolerate relatively high concentrations of sodium chloride without losing their emulsification activity, it is expected that emulsans will be widely used in all enhanced oil recovery techniques for freeing oil from limestone formations.

We claim:

1. Extracellular microbial protein-associated lipopolysaccharides (herein collectively called "α-emulsans") produced by Acinetobacter Sp. ATCC 31012 and its mutants, in which the lipopolysaccharide components (herein collectively called "apo-α-emulsans") are completely N-acylated and partially O-acylated heteropolysaccharides made up of major amounts of D-galactosamine and an aminouronic acid, such apo-α-emulsans containing at least 5 percent by weight of fatty acid esters (1) in which the fatty acids contain from about 10 to about 18 carbon atoms; and (2) about 50 percent by weight or more of such fatty acids are composed of 2-hydroxydodecanoic acid and 3-hydroxydodecanoic acid, the α-emulsans being characterized by a Specific Emulsification Activity of about 200 units per milligram or higher, where one unit per milligram of Specific Emulsification Activity is defined as that amount of emulsifying activity per milligram of bioemulsifier which yields 100 Klett absorption units using a standard hydrocarbon mixture consisting of 0.1 ml of 1:1 (v/v) hexadecane/2-methylnaphthalene and 7.5 ml of Tris-Mg buffer.

2. α-Emulsans according to claim 1, in which the aggregate fatty acids contained in the O-lipoacyl portion of the apo-α-emulsan components have an average equivalent weight from about 200 to about 230.

3. α-Emulsans according to claim 1, in which the apo-α-emulsan components contain from at least 5 to about 7 percent by weight of fatty acid esters in which the aggregate fatty acids have an average equivalent weight from about 200 to about 230.

4. α-Emulsans according to claim 1, in which the apo-α-emulsan components contain from about 7 to about 14 percent by weight of fatty acid esters in which the aggregate fatty acids have an average equivalent weight from about 200 to about 230.

5. α-Emulsans according to claim 1, in which the apo-α-emulsan components contain from about 14 to about 19 percent by weight of fatty acid esters in which the aggregate fatty acids have an average equivalent weight from about 200 to about 230.

6. α-Emulsans according to claim 1, in which the apo-α-emulsan components contain from about 0.5 to about 0.7 micromoles per milligram of fatty acid esters in which from about 50 to about 70 percent by weight of such fatty acids are composed of 2-hydroxydodecancic acid and 3-hydroxydodecanoic acid.

7. α-Emulsans according to claim 1, in which the apo-α-emulsan components are composed of from about 20 to about 35 percent by weight of D-galactosamine; from about 30 to about 35 percent by weight of hexosamineuronic acid; and from about 7 to about 19 percent by weight of fatty acid esters in which the fatty acids contain from about 10 to about 18 carbon atoms and are characterized by an average equivalent weight from about 200 to about 230, from about 50 to about 70 percent by weight of such fatty acids in the O-lipoacyl portion of the apo-α-emulsan components being composed of 2-hydroxydodecanoic acid and 3-hydroxydodecanoic acid.

8. α-Emulsans according to claim 1, in which the reduced viscosity of the α-emulsan is 480±50 cc/g between pH 3 to pH 8.5.

9. α-Emulsans according to claim 1, in which the weight average molecular weight of the apo-α-emulsan components is about one million.

10. α-Emulsans according to any of claims 1, 2, 3, 4, 5, 6, 7, 8, or 9, in which the α-emulsans are characterized by a Specific Emulsification Activity of about 350 units per milligram or higher, where one unit per milligram of Specific Emulsification Activity is defined as that amount of emulsifying activity per milligram of bioemulsifier which yields 100 Klett absorption units using a standard hydrocarbon mixture consisting of 0.1 ml of 1:1 (v/v) hexadecane/2-methylnaphthalene and 7.5 ml of Tris-Mg buffer.

11. α-Emulsans according to any of claims 1, 2, 3, 4, 5, 6, 7, 8 or 9, in which the ratio of 2-hydroxydodecanoic acid to 3-hydroxydodecanoic acid in the O-lipoacyl portion of the apo-α-emulsan components is in the range from about 1:4 to about 1:1.

12. α-Emulsans according to any of claims 1, 2, 3, 4, 5, 6, 7, 8 or 9, in which the ratio of 2-hydroxydodecanoic acid to 3-hydroxydodecanoic acid in the O-lipoacyl portion of the apo-α-emulsan components is in the range from about 1:4 to about 1:2.

13. α-Emulsans according to any of claims 1, 2, 3, 4, 5, 6, 7, 8 or 9, in which such α-emulsans are in the form of their respective divalent metal, ammonium or quaternary ammonium salts.

14. An emulsifying agent comprising an aqueous solution in sea water or fresh water containing (A) from about 10 mcg/ml to about 20 mg/ml of the extracellular microbial protein-associated lipopolysaccharides (herein collectively called "α-emulsans") produced by Acinetobacter Sp. ATCC 31012 and its mutants, in which the lipopolysaccharide components (herein collectively called "apo-α-emulsans") are completely N-acylated and partially O-acylated heteropolysaccharides made up of major amounts of D-galactosamine and an aminouronic acid, such apo-α-emulsans containing at least 5 percent by weight of fatty acid esters (1) in which the fatty acids contain from about 10 to about 18 carbon atoms; and (2) about 50 percent by weight or more of such fatty acids are composed of 2-hydroxydodecanoic acid and 3-hydroxydodecanoic acid, the α-emulsans being characterized by a Specific Emulsification Activity of about 200 units per milligram or higher, where one unit per milligram of Specific Emulsification Activity is defined as that amount of emulsifying activity per milligram of bioemulsifier which yields 100 Klett absorption units using a standard hydrocarbon mixture consisting of 0.1 ml of 1:1 (v/v) hexadecane/2-methylnaphthalene and 7.5 ml of Tris-Mg buffer; and (B) from about 1 to about 100 mM of at least one divalent cation.

15. An emulsifying agent according to claim 14, in which the aggregate fatty acids contained in the the apo-α-emulsan components of the α-emulsans have an average equivalent weight from about 200 to about 230.

16. An emulsifying agent according to claim 14, the apo-α-emulsan components of the α-emulsans contain from at least 5 to about 7 percent by weight of fatty acid esters in which the aggregate fatty acids have an average equivalent weight from about 200 to about 230.

17. An emulsifying agent according to claim 14, in which the apo-α-emulsan components of the α-emulsans contain from about 7 to about 14 percent by weight of fatty acid esters in which the aggregate fatty acids have an average equivalent weight from about 200 to about 230.

18. An emulsifying agent according to claim 14, in which the apo-α-emulsan components of the α-emulsans contain from about 14 to about 19 percent by weight of acid esters in which the aggregate fatty acids have an average equivalent weight from about 200 to about 230.

19. An emulsifying agent according to claim 14, in which the apo-α-emulsan components of the α-emulsans contain from about 0.5 to about 0.7 micromoles per milligram of fatty acid esters in which from about 50 to about 70 percent by weight of such fatty acids are composed of 2-hydroxydodecanoic acid and 3-hydroxydodecanoic acid.

20. An emulsifying agent according to claim 14, in which the apo-α-emulsan components are composed of from about 20 to about 35 percent by weight of D-galactosamine; from about 30 to about 35 percent by weight of hexosamine-uronic acid; and from not less than 5 to about 19 percent by weight of fatty acid esters in which the fatty acids contain from about 10 to about 18 carbon atoms and are characterized by an average equivalent weight from about 200 to about 230, from about 50 to about 70 percent by weight of such fatty acids in the O-lipoacyl portion of the apo-α-emulsan components being composed of 2-hydroxydodecanoic acid and 3-hydroxydodecanoic acid.

21. An emulsifying agent according to claim 14, in which the reduced viscosity of the α-emulsans in 480±50 cc/g between pH 3 to pH 8.5.

22. An emulsifying agent according to claim 14, in which the weight average molecular weight of the apo-α-emulsan components of the α-emulsans is about one million.

23. An emulsifying agent according to claim 14, in which the concentration of the α-emulsans is in the range from about 50 mcg/ml to about 10 mg/ml.

24. An emulsifying agent according to claim 14, in which the divalent cation is magnesium ($Mg^{++}$) in concentrations in the range from about 5 to about 40 mM.

25. An emulsifying agent according to any of claims 14, 15, 16, 17, 18, 19, 20, 21, 22, 23, or 24, in which the α-emulsans in such aqueous solution are characterized by a Specific Emulsification Activity of about 350 units per milligram or higher, where one unit per milligram of Specific Emulsification Activity is defined as that amount of emulsifying activity per milligram of bioemulsifier which yields 100 Klett absorption units using a standard hydrocarbon mixture consisting of 0.1 ml of 1:1 (v/v) hexadecane/2-methylnaphthalene and 7.5 ml of Tris-Mg buffer.

26. An emulsifying agent according to any of claims 14, 15, 16, 17, 18, 19, 20, 21, 22, 23, or 24, in which the ratio of 2-hydroxydodecanoic acid to 3-hydroxydodecanoic acid in the O-lipoacyl portion of the apo-α-emulsan components of the α-emulsans is in the range from about 1:4 to about 1:1.

27. An emulsifying agent according to any of claims 14, 15, 16, 17, 18, 19, 20, 21, 22, 23 or 24, in which the ratio of 2-hydroxydodecanoic acid to 3-hydroxydodecanoic acid is in the range from about 1:4 to about 1:2 in the O-lipoacyl portion of the apo-α-emulsan components of the α-emulsans.

28. An emulsifying agent according to any of claims 14, 15, 16, 17, 18, 19, 20, 21, 22, 23, or 24, in which the α-emulsans in such aqueous solution are in the form of their respective divalent metal, ammonium or quaternary ammonium salts.

* * * * *

UNITED STATES PATENT AND TRADEMARK OFFICE
CERTIFICATE OF CORRECTION

PATENT NO. : 4,395,354

DATED : July 26, 1983

INVENTOR(S) : David L. Gutnick, Eugene Rosenberg, Igal Belsky and Zinaida Zosim

It is certified that error appears in the above—identified patent and that said Letters Patent is hereby corrected as shown below:

In the Title, "EMULSANS" should read -- α-EMULSANS --.
In the Abstract, line 3, "microbiol" should read -- microbial --.
Column 3, line 40, "associated" should read -- associates --.
Column 4, line 53, "course" should read -- source --.
Column 6, line 45, "(i)" should read -- (1) --.
Column 7, line 43, "hydroxydodecanoid" should read
   -- hydroxydodecanoic --.
Column 11, line 2, "lipoheterpolysaccharide" should read
   -- lipoheteropolysaccharide --.
Column 17, line 1, "of" should read -- for --.
Column 20, line 45, "hydrochloride" should read -- hydrochloric--.
Column 23, line 16, in Table IV, "χ-Emulsan" should read
   -- α-Emulsan --.
Column 24, line 24, "have" should read -- has --.
Column 24, line 39, "V" should read -- $\bar{V}$ --.
Column 25, line 3, in Table VI, "(A)" should read --(Å)--.
Column 25, line 31, "A" should read -- Å --.
Column 28, line 1, "sa" should read -- $\underline{sea}$ --.
Column 29, line 13, "r" should read -- $\bar{r}$ --.
Column 33, line 39, in Table IX, "3-3" should read -- 2-3 --.
Column 38, line 25, "sterlizable" should read -- sterilizable --.
Column 39, line 6, "gyrotary" should read -- gyratory --.
Column 39, line 26, "gyrotary" should read -- gyratory --.
Column 39, line 42, "gyrotary" should read -- gyratory --.
Column 41, line 40, "ressure" should read -- pressure --.
Column 41, lines 44-45, "hydroxyamic" should read
   -- hydroxamic --.
Columns 43-44, line 19, in Table XII, "apo- -emulsan" should
   read -- apo-α-emulsan --.
Column 45, line 20, "show" should read -- shows --.
Column 46, line 14, in Table XIV, Column 2, "Fraction 3"
   should read -- Fraction 2 --.

UNITED STATES PATENT AND TRADEMARK OFFICE
CERTIFICATE OF CORRECTION

PATENT NO. : 4,395,354
DATED : July 26, 1983
INVENTOR(S) : David L. Gutnick, Eugene Rosenberg, Igal Belsky, and Zinaida Zosim It is certified that error appears in the above-identified patent and that said Letters Patent is hereby corrected as shown below:

Column 46, line 15, in Table XIV, Column 1, "Fraction 2" should read -- Fraction 1 --.
Column 46, line 16, in Table XIV, Column 1, "Fraction 3" should read -- Fraction 2 --.
Column 47, line 33, "XANFLO" should read -- XANFLD --.
Column 49, line 63, in Table XVII, "PH" should read -- pH --.
Column 51, line 56, "Aghi Jari" should read -- Agha Jari --.
Column 53, line 22, "2-hydroxydodecancic" should read -- 2-hydroxydodecanoic --.

Signed and Sealed this

Twelfth Day of June 1984

[SEAL]

Attest:

Attesting Officer

GERALD J. MOSSINGHOFF

Commissioner of Patents and Trademarks